United States Patent
Gordon et al.

(10) Patent No.: US 12,342,825 B2
(45) Date of Patent: Jul. 1, 2025

(54) MICROBIAL CONSORTIA PRODUCING DIPICOLINIC ACID AND METHODS FOR SELECTING MICROBES FOR CO-FORMULATION WITH CARRIERS

(71) Applicant: AMVAC Chemical Corporation, Newport Beach, CA (US)

(72) Inventors: Benjamin Gordon, Davis, CA (US); **Frederic

(56) References Cited

OTHER PUBLICATIONS

Ahemad et al., "Mechanisms and applications of plant growth promoting rhizobacteria: Current perspective," *Journal of King Saud University—Science*, vol. 26, pp. 1-20, 2014.
Berninger et al., "Maintenance and assessment of cell viability in formulation of non-sporulating bacterial inoculants," *Microbial Biotechnology*, vol. 11, pp. 277-301, 2018.
Erkovan et al., "Effects of Phosphorus Fertilizer and Phosphorus Solubilizing Bacteria Application on Clover Dominant Meadow: I. Hay Yield and Botanical Composition," *Turkish Journal of Field Crops*, vol. 15, No. 1, pp. 12-17, 2010.
Latha et al., "Effect of Microbial and Chemical Fertilizer on Egg Plant (*Solanum melongena* LINN.) C.Var CO-2," *Int. J. Pure App. Biosci.*, vol. 2, No. 4, pp. 119-124, 2014.
Lee et al., "*Fontibacillus panacisegetis* sp. nov., isolated from soil of a ginseng field," *International Journal of Systematic and Evolutionary Microbiology*, vol. 61, pp. 369-374, 2011.
Lee et al., "Transfer of *Bacillus ehimensis* and *Bacillus chitinolyticus* to the genus *Paenibacillus* with emended descriptions of *Paenibacillus ehimensis* comb. nov. and *Paenibacillus chitinolyticus* comb. nov.," *International Journal of Systematic and Evolutionary Microbiology*, vol. 54, pp. 929-933, 2004.
Malusá et al., "Technologies for Beneficial Microorganisms Inocula Used as Biofertilizers," *The Scientific World Journal*, vol. 2012, Article ID 491206, 2012 (12 pages).
Orsburn et al., "EtfA catalyses the formation of dipicolinic acid in *Clostridium perfringens*," *Molecular Microbiology*, vol. 75, No. 1, pp. 178-186, 2010.
Paulsrud et al., "Seed Treatment, Oregon Pesticide Applicator Training Manual," 2001 (33 pages).
Pathway Biologic, "PowerBlend Microbial Inoculant," 2017 (8 pages).
Setlow, P., "Spores of *Bacillus subtilis*: their resistance to and killing by radiation, heat and chemicals," *Journal of Applied Microbiology*, vol. 101, pp. 514-525, 2006.
Shaheen et al., "The Integrated Use of Bio-inoculants and Chemical Nitrogen Fertilizer on Growth, Yield and Nutritive Value of Two Okra (*Abelmoschus esculentus*, L.).Cultivars," *Australian Journal of Basic and Applied Sciences*, vol. 1, No. 3, pp. 307-312, 2007.
Tamez-Hidalgo, "Dynamics of bacterial endospores, and microbial activities in soils and sediments," PhD Dissertation, 2014 (139 pages).
Partial Supplementary European Search Report and Provisional Opinion, dated Feb. 28, 2022, for EP Application No. 19815883.4 (13 pages).
Slieman et al., "Role of Dipicolinic Acid in Survival of *Bacillus subtilis* Spores Exposed to Artificial and Solar UV Radiation," *Applied and Environmental Microbiology*, vol. 67, No. 3, pp. 1274-1279, 2001.

* cited by examiner

FIG. 1A

```
                                    1
Bacillus megaterium              -MLTDLHIAV IGGDARQLEV IRKLI-QLDA KTSLIGFDQL DHGFTGATKY QIEELDFSQV
Bacillus subtilis                -MLTGLKIAV IGGDARQLEI IRKLT-EQQA DIYLVGFDQL DHGFTGAVKC NIDEIPFQQI
Paenibacillus cookii             -MLTGLTIAI IGGDARQLEI IRKLT-EQHA DIYLAGFDQL DDGFTGTVKC KIDEIPFQKI
Bacillus licheniformis           -MLTGLTIAI IGGDARQLEI IRKLT-EQDA KVFLIGFDQL DHGFTGATKL KLNELDFGTI
Paenibacillus lautus             -MLTGVRTVF VGGDARQIEV IRKCA-EMDA SVMIAGFEKL QDSFQGVTRE PLTPELLSDA
Oceanobacillus oncorhynchi       ---MSRRIAV IGGDARYLEL IKILKSNHDN EVILCGFDKL EQGFTGLNES ALDELDQSKL
Bacillus amyloliquefaciens       -MLTGVQIVF LGGDARQIEV IRKCS-EMDA TVSVVGFDNL KEKLQGVTRD HLTAELLAAA
Bacillus sp.                     -MLTGLQIAV IGGDARQLEV IRKLT-ELDA KLYLVGFEQL DHAFSGAVKE KLDEVDFTCI
Paenibacillus chibensis          -MLTGVQIVF LGGDARQVEV IRKCS-EMDA TVSVVGFDNL KQKLQGVTRD HLTAELLAAA
Bacillus flexus                  -MLTDLHIAV IGGDARQLEV IRKLI-QLDA KTSLIGFDQL DHGFTGATKY QIDELNFSDV
Bacillus firmus                  -MLTGTQIAV IGGDARQLEI IRKLT-ELDA KLSLIGFEQL DHAFSGAVKE KIDEVDFSHI
Virgibacillus halophilus copy 1  MNLKDKKILL IGGDERYLEV VKKLD-DLGA SVVLAGYDKA GLSSGRVQIS KLEDVNFSNL
Virgibacillus halophilus copy 2  ---------- ---------- ---------M KTIVTGFNKL DQGFTGVQHV EFAEMEHEDI
Paenibacillus azoreducens        -MLTGVQIVF LGGDARQIEV IRKCS-EMDA TVSVVGFDNL KEKLQGVTRD QLTGELLAGA
Consensus60                      NMLTGXXIAX IGGDARQLEV IRKLXSEXDA XXXLXGFDXL XXXFXGXXXX XXXEXXXXXX
PRK08306                         ---TGKHIAV IGGDARQLEL IRKLV-ELGA KVSLVGFDQL DHGFTGATKS SSLEEALSDV 61
Bacillus megaterium              DAIILPVPGT NHEGQVD-TI FSNEKVVLTE EILKKTPEHC IIYSGISNGY LNELVKTTNR
Bacillus subtilis                DSIILPVSAT TGEGVVS-TV FSNEEVVLKQ DHLQRTPAHC VIFSGISNAY LENIAAQAKR
Paenibacillus cookii             DSIILPVSAT TGEGVVS-TV FSNEEVVLKQ SYLERTPEHC VIYSGISNAY LEGIASEAGR
Bacillus licheniformis           DSIILPVSGT SMEGTVA-TV FSNEKVVLKQ EHLEKTKPHC AIYSGISNQY LDGMAKGANR
Paenibacillus lautus             DALILPVVGC DDEGRVS-AL FSEGPLRLQE EHIAANPGHG VIYTGMAKPY LRSLCDKYKI
Oceanobacillus oncorhynchi       DVVVLPITGT DSKGNVE-TV FTDKKIHLDE AWFQELHAEC MIFTGMTNAY LTSMAEKAGV
Bacillus amyloliquefaciens       DVLVLPVVGC DDNGIIH-TQ FSNESLKLQD EHMAALRRGC KVYTGMAKPY LRSLCAHHEI
Bacillus sp.                     DAIILPVPGA GVDGQID-TI FSNEKITINE EILKKTPQHC KIYSGINPPY LQEISTKADR
Paenibacillus chibensis          DVLVLPVVGC DDNGNIH-TQ FSNEPLKLQD EHMASLRKGC KVYTGMAKPY LRSLCAQHEI
Bacillus flexus                  DAIILPVPGT NHEGQVD-TI FSNEKVILTE EILASTPAHC TIYSGISNDY LNSLVQKTNR
Bacillus firmus                  DAIILPVPGT GLEGQIE-TI FSNEKVTLEE EILSQTPAHC TVYSGITNSY LTGVTKSADR
Virgibacillus halophilus copy 1  YAILLPVSGT DGEGNITMSS FTDQQLCLTE QMISQLPPSC KIYTGVSGSF LKRMGSKFQK
Virgibacillus halophilus copy 2  DVVVLPITGT QKGGKVE-TV FSDEEIVLTK DWFEKFQRPT PVFTGISNQD LDGMVKNSKA
Paenibacillus azoreducens        DVLVLPVVGC DDNGIIH-TQ FSNESLKLRGC EHMASLRRGC KVYTGMAKPY LRSLCAHHEI
Consensus60                      DXXXLPVXGT XXXGXXXNTX FSNEXXXLXX EXXXXXXXXC XIYXGXXXXY LXXXXXXXXX
PRK08306                         DVIILPVPGT NDEGNVD-TV FSNEKLVLTE ELLELTPEHC TIFSGIANPY LKELAKETNR 121
Bacillus megaterium              KLVQLFERDD VAIYNSIPTV EGTIMLVIQH TDFTIHGSNI SVLGLGRVGM SVARSFAALG
Bacillus subtilis                KLVKLFERDD IAIYNSIPTV EGTIMLAIQH TDYTIHGSQV AVLGLGRTGM TIARTFAALG
Paenibacillus cookii             KLVKLFERDD IAIFNSIPTV EGTIMMAIQH TDYTIHGSNV AVLGMGRTGM TIARTFAALG
Bacillus licheniformis           RLIKLFERDD IAIYNSIPTV EGAIMMAIQH TDFTIHGSNV MVLGLGRTGM SISRTFSALG
Paenibacillus lautus             KLVEILERDD VAIYNSIPTA EGALMMAIQN TDFTIHGSTS MVLGMGRTGF TMARSLQGLG
Oceanobacillus oncorhynchi       TLVPLLDRDD VAIYNSIPTA EGAIMMAFEH TDQTVHSSRV MVVGFGRVGN TVANKFSALG
Bacillus amyloliquefaciens       KLIELLDRDE VAISNSIPTS EGALVMAIQN TDFTIHGSNC MVLGLGRTGF TMAKSLQGLG
Bacillus sp.                     EVVQLFNRDD VAIYNSIPTV EGALMMAIQH TDFTIHGSNV TVLGLGRTGM SIARAFHALG
Paenibacillus chibensis          KLVELLDRDE VAISNSIPTA EGALVMAIQN TDFTIHGSRC MVLGLGRTGF TMAKSLQGLG
Bacillus flexus                  TLIQLFERDD VAIYNSIPTV EGTIMLVIQH TDFTIHGANI SVLGLGRVGM SVARSFAALG
Bacillus firmus                  RLVQLFERDD VAIYNSIPTV EGTIMMAIQH TDFTIHGSNI AVIGLGRVGM SVARTFRALG
Virgibacillus halophilus copy 1  EIISILARED IAIYNSIPTA EGALQLAMEQ TDYTMHSASV MVLGFGKVGN TTARLFSAVG
Virgibacillus halophilus copy 2  QIIPLLDRDD VAIYNSIPTA EGTIMMAMEH TDYTIHSSRV IVAGFGRVGH TVANKFSALG
Paenibacillus azoreducens        RLVELLDRDE VAISNSIPTA EGALVMAIQN TDFTIHGSDC MVLGLGRTGF TMAKSLQGLG
Consensus60                      XLVXLXXRDD VAIYNSIPTX EGXXMMAIQH TDFTIHGSXX XVLGLGRXGX TXARXFXALG
PRK08306                         KLVELFERDD VAILNSIPTA EGAIMMAIEH TPITIHGSNV LVLGFGRTGM TLARTLKALG
```

FIG. 1B

```
                                     181
Bacillus megaterium             ANVKVGARKS EHLARIAEMG LQPFYLSELD KEIADSDICI NTIPYPILTA KTLSNVPTHA
Bacillus subtilis               ANVKVGARSS AHLARITEMG LVPFHTDELK EHVKDIDICI NTIPSMILNQ TVLSSMTPKT
Paenibacillus cookii            AKVKVGARSS AHLARITEMG LSPFQLEELT EHVNDIDICI NTVPSLILNQ SVLSRMTPKT
Bacillus licheniformis          ARVKVGARDS AHLARIMEMG LTPFHTNELA EHVENIDICI NTIPSLILDK HVLSRMTPRT
Paenibacillus lautus            AKIRNGVRKS EHYARAEEMG WKPFLVRDLG SYVSDIDLLF NTIPTMIVTA QIISKMPREA
Oceanobacillus oncorhynchi      AKVSVCARSI RDLARITEMG LQAVPLHELS NHTENCDILI NTIPSLVVTK EAIQNLPTNA
Bacillus amyloliquefaciens      AKVKVGVRSE KDVARAEVMG NEPFLTRDLA DHVRNIDLIF NTIPTMIVTA QILSRMPQSA
Bacillus sp.                    AKVKVGARKS EHIARITEMG LTPFHLSDIE EAVVDTDICI NTIPVQVVVA SVIAKMPVHT
Paenibacillus chibensis         AKVKVGVRSE KDVARAEVMG NEPFLTRDLG DHVSNIDLIF NTIPTMIVTA QILSKMPLSS
Bacillus flexus                 ANVKVGARKS EHLARISEMG LTPFHLNDLA QEITDSDICI NTIPYPVLTS SVLANIPTHA
Bacillus firmus                 AKVKVGARKS EHIARITEMG LTPFNLKEIE DAVKDVDICI NTAPHLVVTA SVISKMPTHT
Virgibacillus halophilus copy 1 CNVSVAIRKD SAAARVREMG LKPLYTHHLS EEIGQYQIII NTVPDLVLDE SLLNIVSSKA
Virgibacillus halophilus copy 2 AKVSVAASSI HDIARINEMG LFAITMKELA KAAADCDILI NTIPAPVINK EAISQLPHHA
Paenibacillus azoreducens      ARVKVGVRSE RDFARAEVMG NEPFLTRDLA DYVRSIDLIF NTIPTMIVTA QILSRMPQNT
Consensus60                     AXVKVGARXX XXXARIXEMG LXPFXXXXLX XXVXXXDIXI NTIPXXXXXX XXLSKMPXXX
PRK08306                        ANVTVGARKS AHLARITEMG LSPFHLSELA EEVGKIDIIF NTIPALVLTK EVLSKMPPEA 241
Bacillus megaterium             LIIDLASKPG GTDFRYAEKR GIKAILAPGL PGIVAPKTAG QIVANVLVNL LKDAADAREE
Bacillus subtilis               LILDLASRPG GTDFKYAEKQ GIKALLAPGL PGIVAPKTAG QILANVLSKL LAEIQAEEGK
Paenibacillus cookii            LILDLASRPG GTDFKYAEKQ GIKALLAPGL PGIVAPKTAG QIIANVLSKL LADLKKEGK-
Bacillus licheniformis          LILDLATRPG GTDFDFAEKQ GIKALLAPGL PGIVAPKTAG QIIANVLCNL LSELTTDRKG
Paenibacillus lautus            VIIDLASAPG GCDFRYAEKR GIKAMLAPGL PGIVAPKTAG IIMANTLVEL ISEEIKIRED
Oceanobacillus oncorhynchi      VIIDLASKPG GTDFDFAKKR GIQAILARSL PGIVAPRTAG KILANVMEQI LEEERASE--
Bacillus amyloliquefaciens      VIIDLASAPG GCDFRYAEKR GIKALLAPGL PGIVAPKTAG SIIANTLVQL ISDEFKTRGD
Bacillus sp.                    LIIDLASKPG GTDFRYAEKR GVKALLAPGL PGIVAPKTAG RILANVLSQL ILANFDERED
Paenibacillus chibensis         VIIDLASAPG GCDFRYAEKR GIKALLAPGL PGIVAPKTAG LIIAGSLVQL ISDEFKTRGD
Bacillus flexus                 LVVDLASKPG GTDFRYAEKR GIKAILAPGL PGIVAPKTAG QIVANIVIVTL LKEAADQREE
Bacillus firmus                 LIIDLASKPG GTDFRYAEKR GVKALLAPGL PGIVAPKTAG QILANVLSQL IMEDLQKRKG
Virgibacillus halophilus copy 1 LIIDLASSPG GVDFSVADEL GIRTIHALGL PGKVAPKTAG SIIADTFVSL LS--------
Virgibacillus halophilus copy 2 LIFDLASKPG GTDFDYAKRR GIKAILSESL PGVVAPKTAG KILADVIIQI LSQRKGFEQ-
Paenibacillus azoreducens       VIIDLASAPG GCDFRYAEKR GIKALLAPGL PGIVAPKTAG SIIANSLVQN ISDEFKTRGD
Consensus60                     LIIDLASXPG GTDFXYAEKR GIKAXLAPGL PGIVAPKTAG XIXANVLXXL XXXXXXXRXX
PRK08306                        LIIDLASKPG GTDFEYAEKR GIKALLAPGL PGKVAPKTAG QILANVLSQL LAEDLIARKE 301
Bacillus megaterium             KK-
Bacillus subtilis               ---
Paenibacillus cookii            ---
Bacillus licheniformis          LS-
Paenibacillus lautus            A--
Oceanobacillus oncorhynchi      ---
Bacillus amyloliquefaciens      GQ-
Bacillus sp.                    KQS
Paenibacillus chibensis         GE-
Bacillus flexus                 KQ-
Bacillus firmus                 NTK
Virgibacillus halophilus copy 1 ---
Virgibacillus halophilus copy 2 ---
Paenibacillus azoreducens       GE-
Consensus60                     XXX
PRK08306                        N--
```

FIG. 2

```
                              1
Bacillus megaterium           -MSLKGKRIG FGLTGSHCTY DAVMPEIEKL VNLGAEVLPV VSYTVQSTNT RFGDGEDWVK KIEELTGHAV
Bacillus subtilis             MSSLKGKRIG FGLTGSHCTY EAVFPQIEAL VNEGAEVRPV VTFNVKSTNT RFGEGAEWVK KIEELTGYEA
Paenibacillus cookii          -MSIKGKRIG FGLTGSHCTY EEVFPQIEAL ISQGAEVRPV VTSTVQSTDT RFGEGGDWVR KIEEATGFEA
Bacillus licheniformis        -MSIKGKRIG FGLTGSHCTY DAVFPQIEAL INKGAEVRPV VTHTVKSTDT RFGEGEEWVR RIEELTGFEV
Paenibacillus lautus          -MNWNGITVG YALTGSHCTL EEVMPQIQRF KDGGANVVPI VSSTIMTTDT RFGTSENWQK QLKDITGNDI
Oceanobacillus oncorhynchi    -MTFKNKRIG FGLTGSHHTL PHIFPIIEEL IEQGAEVIPF ITEMVQYTDT KHGKAADNVK RLEKAANHPI
Bacillus amyloliquefaciens    -MNWQGKTVG YAVTGSHCTL EEIMPQVKRF VEAGANVVPI ASGSVQVTDT RFGTAQNWLQ QLKDITGNDI
Bacillus sp.                  -MNLKGKKIG FGLTGSHCTY DAVFPEIEKL VGAGAEVIPV VTFTVQNTVT RFGDGEDWIK RIEEVTGNKV
Paenibacillus chibensis       -MNWQGKTVG YAITGSHCTL EEIMPQVKRF VDEGAKVVPI VSNSVQVTDT RFGTAQNWLQ QLKDITGNDI
Bacillus flexus               -MSLKGKRIG FGLTGSHCTY DAVMPEIEKL VNLGAEVMPV VSYTVQSTNT RFGDGEDWIR KIEEVTGNSV
Bacillus firmus               -MSLKGKRIG FGLTGSHCTY DAVFPEIERL VLAGAEVLPV VTFTVKSTET RFGKGEDWVQ RIEDLTGNKV
Virgibacillus halophilus      -MSLDGKRIG FGLTASHCTY EAVFPEMERL INMGAEVYPV VTYNVKNYDT KFGKASDHEK RLEEITNKEV
Paenibacillus azoreducens     -MNWQGKTVG YAITGSHCTL EEIMPQVKRF VDEGAKVVPI VSNTVQVTDT RFGTAHNWLQ RLKDITGSEL
Consensus60                   MNXKKGKRIG FGLTGSHCTY XXVXPXIEXL VXXGAEVXPV VXXTVQXTDT RFGXXXXWXX XXEXXTGXXX
PRK08305                      -MSLKGKRIG FGLTGSHCTY DEVMPEIEKL VDEGAEVTPI VSYTVQTTDT RFGKAEEWIK KIEEITGNKV 71
Bacillus megaterium           INTIVKAEPL GPKIPLDCNV VAPITGNTMS KFANANTESP VLMAAKATLR NNKPVVLGIS TNDALGLNGV
Bacillus subtilis             IDSIVKAEPL GPKLPLDCNV IAPLTGNSMS KLANANTDSP VLMAAKATIR MNRPVVLGIS TNDALGLNGT
Paenibacillus cookii          IDSIVKAEPL GPKLPLDCNV IAPLTGNSMS KLANANTDSP VLMAAKATIR NGRPVVLGIS TNDGLGLNGT
Bacillus licheniformis        IDSIPKAEPL GPKTPLDCNV VAPLTGNSMS KLANAQTDSP VLMAAKATMR NSRPVVLGIS TNDALGLNGV
Paenibacillus lautus          ISTIVEAEPL GPSKLLDVLV IAPCTGNTTS KLANANTDSP VLMAAKAQMR NCRPLVLAIS TNDGLGLNAA
Oceanobacillus oncorhynchi    ITSIPDAEPY GPDKPLDVNV IAPLTGNSMS KLANAHTDNP VLMAAKSTLR NEHPLLLALT TNDALGLNAK
Bacillus amyloliquefaciens    ITTIVEAEPL GPSKLLDVLV IAPCTGNTTS KLANANTDSP VLMAAKAQMR NQRPLVLAIS TNDGLGLNAS
Bacillus sp.                  IDSIVKAEPL GPKLPLDCNV VAPLTGNSMS KFANANTDSP VLMAAKATLR NEKPVVLGIS TNDALGLNGT
Paenibacillus chibensis       ISSIVDAEPL GPSKLLDVLV IAPCTGNTTS KLANANTDTP VLMAAKAQMR NLRPLVLAIS TNDGLGLNAA
Bacillus flexus               INTIVKAEPL GPKIPLDCNV VAPITGNTMS KFANANTESP VLMAAKATLR NNKPVVLGIS TNDALGLNGV
Bacillus firmus               IDSIVKAEPL GPKIPLDCNV IAPLTGNTMS KFANANTDSP VLMAAKATLR NGKPVVLGIS TNDALGLNGV
Virgibacillus halophilus      VATIPDAEPL GPITPLDCNV IAPLTGNSMS RLANAITDSP PLMAAKATMR NQNPVVLGIS TNDALGLNGV
Paenibacillus azoreducens     ISTIVEAEPL GPSKLLDVLV IAPCTGNTTS KLANAITDSP VLMAAKAQMR NLRPLVLAIS TNDGLGLNAA
Consensus60                   IXXIVXAEPL GPXXPLDCNV IAPXTGNXMS KLANANTDSP VLMAAKATXR NXKPVVLGIS TNDALGLNGX
PRK08305                      INTIVEAEPL GPKKLLDCNV IAPCTGNTNA KLANAITDSP VLMAAKATLR NQRPVVLAIS TNDALGLNAK 141
Bacillus megaterium           NLMRLMATKN IYFIPFGQDD PVLKPNSMVA RMTMLSDTVY AALEDKQIQP VIVERFRDGQ ES
Bacillus subtilis             NLMRLMSTKN IFFIPFGQDD PFKKPNSMVA KMDLLPQTIE KALLHQGLQP ILVENYQGND --
Paenibacillus cookii          NLMRLMSAKN IYFIPFGQDD HVKKPTSLVA RMDLLPITVE KALLHQQVQP VLVHHHE--- --
Bacillus licheniformis        NLMRLMAAKN VVFIPFGQDD PYKKPNSLVA KMDLLVPAVE EALSHKQIQP ILVHNDQ--- --
Paenibacillus lautus          NIAKLLVTKN IYFVPYGQDN PQQKPNSLVA KMNLIPEACY AALEGKQLQP MIVEYSR--- --
Oceanobacillus oncorhynchi    NLAVLLNAKH IYFVPFGQDN PHQKPSSLSA NLDQLIPAAE AALKGKQIQP IIVPYSTKNV LK
Bacillus amyloliquefaciens    NIAKLLITKN IYFVPFGQDN PFQKPNSLVA QMDLIPEACY AALEGKQLQP MILQRVFSA- --
Bacillus sp.                  NLMRLMSTKN IYFIPFGQDD PVKKPNSMVA RMTALSDTIV KAINGEQIQP VIVERYKDGN --
Paenibacillus chibensis       NIAKLLVTKN IYFVPFGQDN PLQKPNSLVA QMDLIPEACY AALEGROLQP MILQRIFSA- --
Bacillus flexus               NLMRLMATKN IYFIPFGQDD PVSKPNSMVA RMPMLSDTVY AALEGKQIQP VVVERFRD-- --
Bacillus firmus               NLMRLMATKN IYFIPYGQDD PVKKPNSMVA RMTALYDTVI HAMEGKQLQP VLVERYKDES --
Virgibacillus halophilus      NLMKLMASKM IYFIPFGQDD PVKKPNSLVS DMTLLPETIE SALNKGNQLQP VLIPFQS--- --
Paenibacillus azoreducens     NIAKLLVAKN IYFVPFGQDN PHQKPNSLVA QMDLIPEACY AALEGRQLQP MLLQRIFSA- --
Consensus60                   NLMXLMXTKN IYFIPFGQDD PXKKPNSLVA XMXLLXXXXX XALXGXQXQP XXVXXXXXXX XX
PRK08305                      NLGRLLNTKN IYFVPFGQDD PVKKPNSLVA RMDLLIDTVE EALEGKQLQP VLIEYFR--- --
```

FIG. 3

```
                          1
C.beijerinckii_00833     -MKIYGINGS PRKNKNTATL LQKALDGVKK AAKD--KKIK TKIINLYDLN YTGCISCPAC
C.beijerinckii_01198     MSKVVIKNGS PRKNKYTTKL LEQVAKGA-- ---KS--KQAK IIKFDLNDSG IRGQQGCFYC
C.beijerinckii_01309     MSKVVIFKGS PRKNKYTARL LEQVAKGA-- ---KS--KGAK VIKFDLNDSG IRGQQGCMYC
C.beijerinckii_03378     MSKVVIFKGS PRKNGYTTKL LDQVAKGA-- ---KS--KGAK VIKFDLNDTG IRGQQGCFYC
C.beijerinckii_01530     -MNIIGISGS SRKKKNTANI VKKILKGA-- ---KK--QQAK TQYFDPNNLD IKPQGCWKC
C.beijerinckii_02440     -MKVLLINGS PRAKKXCTYTT LCKVADKL-- ---KK--KNIK TKIFQIGNKP ISGCIDCQGC
A. fulgidus              -MKLLAINGS PNKKNT-LFL LKVIAKKV-- ---SK--LGHK AKIIHLKDYK IKKCKGCDAC
M. jannaschii            -MKVIGISGS PRPKGNFTLL VREALNAI-- ---AK--KGIK TKFISLADKK LNPCIGGNMC
P. difficile             -MIITVINGS PKKKQATSKV LTYLYKDI-- ---KRLIPIVK INYFDLSKVN PSYCIGCLNC
M. thermophila           -MKITGISGS PRKQGNCKKI IGAALKVA-- ---KK--RGFK TDIVFISNKK VAPCKACGAC
Consensus60              -MXKXXXIKGS PKKXGXTXKL LXXXXXXXKK AAKXLIKGXK XXXFKLXDKK IXXCXGCKXC 61
C.beijerinckii_00833     KRLGSNCYGK CAVKKDLQK- VLKKVSQSKG LIFSSPVYFS NVTGKFLSFL KRLLFPYLV-
C.beijerinckii_01198     RT-N----DG CAVKDYLQF- MYKAITKADA IVPGSPIYYY QITGQAKIWL KRTFPMVG--
C.beijerinckii_01309     RT-N----DG CAVNKYLQF- MYAAIKKADA IVPGSPIYYY TITGQSKVWP KRTFPMIG--
C.beijerinckii_03378     RT-N----DG CAVNKYLQF- MYKALAKADA IVPGSPIYMF QITSQAKTCL KRTFPMVSKL
C.beijerinckii_01530     HKKD----QG CVIKIKNMQK- LNDAIDKANV IVPGSPIYMM QNSAQKKIII KRMPASFSFR
C.beijerinckii_02440     YKSG----KGK CVPKKDIVNI ALKKAKKADG FIFGSPVHYA APSGSITSFL DRFFYAG---
A. fulgidus              LK------CD CSQKKDIYK- VLKKQKADA IVIGTFTYFG NVTGIVKNLI DKSRMARNDN
M. jannaschii            KKK-----GK CPIIDMVDK- ILKKKKADG IILGSPVYFG GVSAQLKMLN DRSRKLR-IG
P. difficile             YKNG----KC INQKKVEY- IHDIITASKG VIFGSPTYG SVTGLFKVFT DKAHNKLRKL
M. thermophila           RDQ-----DF CVIKDIXMDK- IYKKMFAADG IIVAAPVYMG NYPAQLKALF DRSVLLRRKN
Consensus60              XXXXSNGXXX CXXXXDXXXI XXXXXXKADX IXFGSPXYXK XKTGQXKXXX DRXXXAXMXX 121
C.beijerinckii_00833     ----YKNKGT SLAPKRMPTA FIYTMNVKKK VMKQIGYLKT FKRMKSNIGH IPTKPLVMYS
C.beijerinckii_01198     -DNFA--PKH S--GKKLITI ---------- -PTQGSQNPK NGAK----GI KFVNNMLAAY
C.beijerinckii_01309     -NDYK--AKY P--GKKLITI ---------- -PTQGNPDPK IGAK----GV KPANNMLKKL
C.beijerinckii_03378     PNKPI--PRH P--GKKLITV ---------- -FAQGSLDPK KGAK----AI KYVNNIFDWF
C.beijerinckii_01530     YSPYFKKESA A--KKRLVLT ---------- -FNQGNPDPK LFKS----YI DYTKKMFKLL
C.beijerinckii_02440     -NCPANKPGA A---VVS--- ---------- -CRRKDAKSA FDQLKK-YFT ISN--MPVYS
A. fulgidus              -YRLRNRVFA PVVTSG---- ---------- -LKKQQAKYA AMSLIV-YAL GQA--MLPVS
M. jannaschii            -FQLRNKVGG AVAVGA---- ---------- -SKKKQQKTT IQQIKK-FFL IKS--MIVVG
P. difficile             LYR----KPC------ IAV ---------- -T----TYKNA RGSK----AI SFIKKMVLDS
M. thermophila           -FALKNKVKA ALSVGG---- ---------- -SKKKQQKKT IQSIKD-MMK IHG--MIVVG
Consensus60              XXXXXXXXXX XXXXXXLITX FIYTMNVKKK VXXXGXXXXX XXXXXXMXXX XXXXXKXXXX 181
C.beijerinckii_00833     NNTYQ--FD- -----DYSKY KVKSFSKKKK AAKKKI---- ---------- ----------
C.beijerinckii_01198     G--------- WKLKDSILCC GTTNFHSKKL ---------- ---------- -----GKYDS
C.beijerinckii_01309     G--------- WKLKKSIHYC GTNK------ ---------- ---------- ---------NP
C.beijerinckii_03378     G--------- WKLKKCIKYC GTDS------ ---------- ---------- ----------
C.beijerinckii_01530     K--------- PDVTKNPVVT GLKKGPANKR ---------- ---------- ----------
C.beijerinckii_02440     SQYW------ --NM VKGNTFPKVK QDL------- ---------- ----------
A. fulgidus              IVKKPITTGT FPVGVIQKDA GWRS----VK KDK------- ---------- ----------
M. jannaschii            DNDPT----- ----AHYGGT GVGKAPGDCK NKD------- ---------- ----------
P. difficile             G--------G YVCGSLSIKT GFNQNPITKK VKSKIQKVSK KPIYCIKKKK NPPVLSQIYN
M. thermophila           DNS------- ------NPGGI TWNP----AK KDT------- ---------- ----------
Consensus60              XNXXXITXXX KKXXXXXXXX GXXXXPXXXX XDKXXXXKVSK KPIYCIKKKK NPPVLXXXXX 241
C.beijerinckii_00833     ---QFPLDCQ KAFKLGANLI KH-------- ---------- ----------
C.beijerinckii_01198     NLKQFKKLSL RAFKIKGKNLV ---------R ---------- ----------
C.beijerinckii_01309     DLKMPDRLSL RAFKKGKNLA ---------- ---------- ----------
C.beijerinckii_03378     --KVFNKRLSL RAFKKGKNLA ---------- ---------- ----------
C.beijerinckii_01530     -----KDLNI NLKIDVGKTIV ------SKKIGSK--- ---------- ----------
C.beijerinckii_02440     ------RKMQ TNRNLGKKMA WLLKKSIDAGK KACISLPKSK PRVATNFIR
A. fulgidus              ------IAIN SAKALAKKIV KVAKATKKLR KS-------- ----------
M. jannaschii            ------IGLK TARNLGKKVA KVVKLIKK--- ---------- ----------
P. difficile             FIAIKKVLFQ MAFKDIKQYK G---TIDRKK KQIII----- ----------
M. thermophila           ------VKMQ TYGKTAKKKLC DVLKLIQKKR DK-------- ----------
Consensus60              XLXXFXXXXX XAXXXGXMXX XVXXXIXXXX XKGISKFKSK PRVATNFIR
```

MICROBIAL CONSORTIA PRODUCING DIPICOLINIC ACID AND METHODS FOR SELECTING MICROBES FOR CO-FORMULATION WITH CARRIERS

CROSS REFERENCE TO RELATED APPLICATION

This is the § 371 U.S. National Stage of International Application No. PCT/US2019/035530, filed Jun. 5, 2019, which was published in English under PCT Article 21 (2), which in turn claims the benefit of U.S. Provisional Application No. 62/681,469, filed Jun. 6, 2018, which is incorporated herein by reference in its entirety.

FIELD

This disclosure relates to microbes producing dipicolinic acid and methods of identifying microbes with improved viability, methods of co-formulating microbes with carriers, and compositions including the microbes and/or co-formulations.

BACKGROUND

Microbe-based plant biostimulants offer sustainable agriculture practices that protect the health of the ecosystem. Moreover, supplementation of the plant and soil microbiome with beneficial microorganisms has potential in promoting plant growth and plant fitness, increasing productivity, improving soil fertility, and reducing chemical inputs, resulting in more sustainable agricultural practices. In current agricultural practices, microbial biostimulants can be co-applied and/or co-formulated with numerous wet or dry carriers.

SUMMARY

Microbial inoculants can be susceptible to the chemistry of the carrier(s) used. Moreover, storage conditions and length of storage before application can also affect microbes. These factors can negatively impact their viability and ultimately limit their efficacy in the field. Disclosed herein are compositions and methods that result in improved microbe survival and/or improved co-formulation of microbes with carriers or seeds. In some embodiments, the methods include selecting one or more microbes with extended viability or survival either alone and/or in co-formulation with one or more carriers or seeds.

In some embodiments, disclosed herein are microbes that produce dipicolinic acid (DPA) and compositions including such microbes. In one example, the composition includes *Bacillus amyloliquefaciens, Bacillus firmus, Bacillus flexus, Bacillus licheniformis, Bacillus megaterium, Bacillus pumilus, Bacillus koreensis, Bacillus drentensis, Bacillus subtilis, Clostridium bifermentans, Clostridium beijerinckii, Clostridium pasteurianum, Lactobacillus paracasei, Fontibacillus* sp. (*panacisegetis*), *Oceanobacillus oncorhynchi, Paenibacillus lautus, Paenibacillus azoreducens, Paenibacillus chibensis, Paenibacillus cookii, Paenibacillus* sp. (*chitinolyticus*), *Paenibacillus* sp. (P1XP2), *Pseudomonas* sp., and *Streptomyces griseus* (in some examples, referred to herein as the "DFC" consortium). In one embodiment, the composition includes cells of microbial species deposited with the American Type Culture Collection (ATCC, Manassas, VA) on May 16, 2019 and assigned deposit number PTA-125924. In other embodiments the disclosed microbial consortia or compositions include, consist essentially of, or consist of two or more (such as 5 or more, 10 or more, 15 or more, 20 or more, or all) microbes having 16S rDNA sequences with at least 95% identity (such as at least 96%, 97%, 98%, 99% identity, or more) with SEQ ID NOs: 3-25.

Also disclosed are compositions including the disclosed microbes or consortia (for example, the DFC consortium) and one or more carriers (such as a dry carrier or a liquid carrier) or one or more seeds. In some examples, the carrier includes a liquid or dry fertilizer, a soil-derived substance, an organic substance, an inert material, a dust control chemical, or a mixture of two or more thereof.

In some embodiments, the methods include selecting a microbe for co-formulation with a carrier or seed, including identifying a microbe that comprises one or more dipicolinic acid (DPA) synthase genes, a microbe that expresses one or more DPA synthase proteins, and/or a microbe that produces detectable amounts of DPA; and selecting the microbe for co-formulation with a carrier. In some embodiments, the methods also include co-formulating the selected microbe with the carrier or seed. In some examples, the selected microbes include one or more of those included in Tables 25 or 26, including, but not limited to all of those listed in Table 26.

In some examples, the methods include detecting one or more DPA synthase genes (such as a DPA synthase subunit A (DpaA) gene and/or or a DPA synthase subunit B (DpaB) gene) or one or more DpaA and/or DpaB proteins in a microbe. DpaA genes include nucleic acids that encode a DpaA protein with at least 20% (for example, at least 60%) sequence identity to any one of the amino acid sequences in FIG. 1 (e.g., SEQ ID NOs: 26-41). DpaB genes include nucleic acids that encode a DpaB protein with at least 20% (for example, at least 60%) sequence identity to any one of the amino acid sequences in FIG. 2 (e.g., SEQ ID NOs: 42-56). DpaA proteins include DpaA proteins with at least 20% (such as at least 60%) sequence identity to any one of the amino acid sequences in FIG. 1 (e.g., SEQ ID NOs: 26-41). DpaB proteins include DpaB proteins with at least 20% (such as at least 60%) sequence identity to any one of the amino acid sequences in FIG. 2 (e.g., SEQ ID NOs: 42-56). In further examples, the methods include detecting one or more Isf genes or proteins in a microbe. Isf genes include nucleic acids that encode an Isf protein with at least 20% (for example, at least 60%) sequence identity to any one of the amino acid sequences in FIG. 3 (e.g., SEQ ID NOs: 57-67). Isf proteins include Isf proteins with at least 20% (such as at least 60%) sequence identity to any one of the amino acid sequences in FIG. 3 (e.g., SEQ ID NOs: 57-67). In other examples, the methods include detecting DPA in a microbe or medium containing a microbe, for example, utilizing a fluorescence assay.

In some embodiments, the method includes co-formulating one or more selected microbes with a carrier by contacting the selected microbes (including, but not limited to the microbial consortia disclosed herein) in liquid or dry form with one or more liquid or dry carriers. In some examples, the carrier includes a liquid or dry fertilizer, a soil-derived substance, an organic substance, an inert material, a dust control chemical, or a mixture of two or more thereof. In other examples, the methods include treating seeds with the one or more selected microbes (including, but not limited to the microbial consortia disclosed herein). In some examples, the methods further include co-formulating the one or more selected microbes and one or more microbes that do not comprise one or more DPA synthase genes, do not express one or more DPA synthase proteins, and/or a microbe that does not produce detectable amounts of DPA with the carrier or seed.

The foregoing and other features of the disclosure will become more apparent from the following detailed description, which proceeds with reference to the accompanying figures.

BRIEF DESCRIPTION OF THE DRAWINGS

FIG. 1 is an alignment of DpaA protein sequences from the indicated bacteria. Fourteen DpaA sequences from 13 strains (SEQ ID NOs: 26-39) were aligned using Clustal Omega (clustal.org/omega) with default settings. A consensus sequence was then generated ("Consensus60"; SEQ ID NO: 40) using a minimum sequence identity threshold of 60%. PRK08306 (SEQ ID NO: 41) is the consensus sequence of the DpaA superfamily retrieved from the NCBI CDD Conserved Domain Family database (ncbi.nih.gov/Structure/cdd/cddsrv.cgi).

FIG. 2 is an alignment of DpaB protein sequences from the indicated bacteria. Thirteen DpaB sequences from 13 strains (SEQ ID NOs: 42-54) were aligned using Clustal Omega (clustal.org/omega) with default settings. A consensus sequence was then generated ("Consensus60"; SEQ ID NO: 55) using a minimum sequence identity threshold of 60%. PRK08305 (SEQ ID NO: 56) is the consensus sequence of the DpaB superfamily retrieved from the NCBI CDD Conserved Domain Family database (ncbi.nih.gov/Structure/cdd/cddsrv.cgi).

FIG. 3 shows an alignment of 10 Isf protein sequences from five bacteria (SEQ ID NOs: 57-66) and a consensus sequence (SEQ ID NO: 67).

SEQUENCE LISTING

Figure 4:
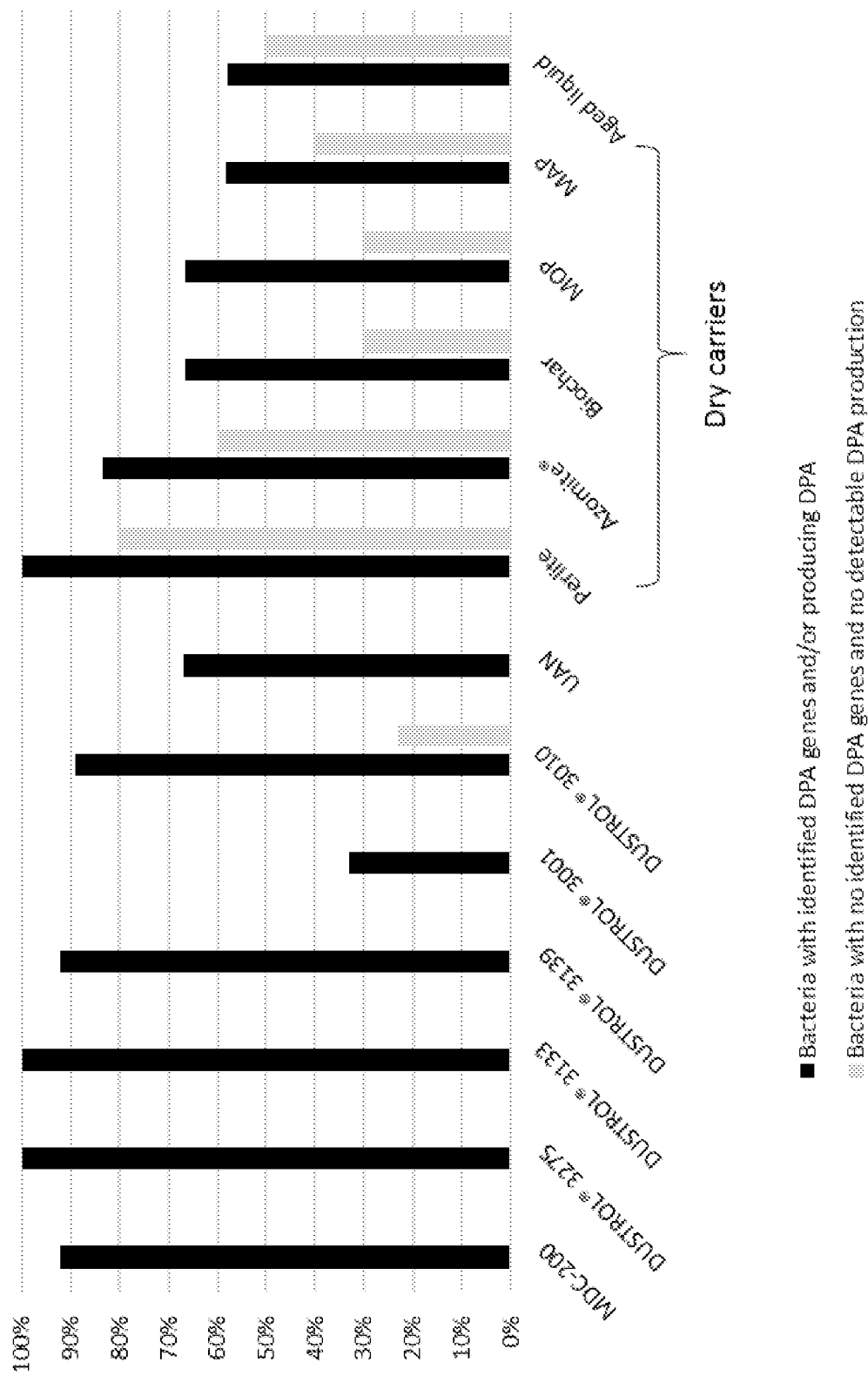
FIG. 4 is a graph summarizing survival of bacteria in combination with the indicated carriers.

Any nucleic acid and amino acid sequences listed herein or in the accompanying Sequence Listing are shown using standard letter abbreviations for nucleotides and amino acids, as defined in 37 C.F.R. § 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Dec. 2, 2020, and is ~142 kilobytes, which is incorporated by reference herein.

SEQ ID NO: 1 is a consensus 16S rDNA nucleic acid sequence from *Streptomyces pratensis.*

SEQ ID NO: 2 is a consensus 16S rDNA nucleic acid sequence from *Streptomyces venezuelae.*

SEQ ID NO: 3 is a 16S rDNA nucleic acid sequence from *Bacillus firmus.*

SEQ ID NO: 4 is a consensus 16S rDNA nucleic acid sequence from *Paenibacillus azoreducens.*

SEQ ID NO: 5 is a 16S rDNA nucleic acid sequence from *Bacillus amyloliquefaciens.*

SEQ ID NO: 6 is a 16S rDNA nucleic acid sequence from *Bacillus flexus.*

SEQ ID NO: 7 is a 16S rDNA nucleic acid sequence from *Bacillus licheniformis.*

SEQ ID NO: 8 is a 16S rDNA nucleic acid sequence from *Bacillus megaterium.*

SEQ ID NO: 9 is a 16S rDNA nucleic acid sequence from *Bacillus pumilus.*

SEQ ID NO: 10 is a 16S rDNA nucleic acid sequence from *Bacillus koreensis.*

SEQ ID NO: 11 is a 16S rDNA nucleic acid sequence from *Bacillus drentensis.*

SEQ ID NO: 12 is a 16S rDNA nucleic acid sequence from *Bacillus subtilis.*

SEQ ID NO: 13 is a 16S rDNA nucleic acid sequence from *Clostridium bifermentans.*

SEQ ID NO: 14 is a 16S rDNA nucleic acid sequence from *Clostridium beijerinckii.*

SEQ ID NO: 15 is a 16S rDNA nucleic acid sequence from *Clostridium pasteurianum.*

SEQ ID NO: 16 is a 16S rDNA nucleic acid sequence from *Lactobacillus paracasei.*

SEQ ID NO: 17 is a partial 16S rDNA nucleic acid sequence from *Fontibacillus* sp. (*panacisegetis*).

SEQ ID NO: 18 is a 16S rDNA nucleic acid sequence from *Oceanobacillus oncorhynchi.*

SEQ ID NO: 19 is a 16S rDNA nucleic acid sequence from *Paenibacillus lautus.*

SEQ ID NO: 20 is a 16S rDNA nucleic acid sequence from *Paenibacillus chibensis.*

SEQ ID NO: 21 is a 16S rDNA nucleic acid sequence from *Paenibacillus cookii.*

SEQ ID NO: 22 is a 16S rDNA nucleic acid sequence from *Paenibacillus* sp. (*chitinolyticus*).

SEQ ID NO: 23 is a partial 16S rDNA nucleic acid sequence from *Paenibacillus* sp. (P1XP2).

SEQ ID NO: 24 is a 16S rDNA nucleic acid sequence from *Pseudomonas* sp.

SEQ ID NO: 25 is a 16S rDNA nucleic acid sequence from *Streptomyces griseus.*

SEQ ID NOs: 26-39 are DpaA amino acid sequences.

SEQ ID NO: 40-41 are DpaA consensus amino acid sequences.

SEQ ID NOs: 42-54 are DpaB amino acid sequences.

SEQ ID NO: 55-56 are DpaB consensus amino acid sequences.

SEQ ID NOs: 57-66 are Isf amino acid sequences.

SEQ ID NO: 67 is an Isf consensus amino acid sequence.

DETAILED DESCRIPTION

Microbes that do not form spores are often more susceptible to deleterious factors occurring during processing and field application than microbes that form spores. The selection process for identifying microbes that form spores from large microbial inventories can be tedious and time consuming. This usually involves wet-lab testing for survivability (for example, in co-formulations with carriers of choice), with limited guarantee of survivability and final product extended shelf-life.

Disclosed herein is a novel strategy and method for selecting microbes with high confidence of extended shelf-life as either standalone biostimulant formulations and/or in co-formulation with wet or dry carriers or seeds, thus significantly accelerating lead time to new product testing in field trials. As described herein, spore forming bacteria with identified DPA genes or proteins and/or producing DPA outperform strains with no identified DPA genes and no detectable DPA production in terms of survivability in co-formulation with carriers over time. Finally, a consortium of microbes that includes DPA-producing strains is described.

I. Terms

Unless otherwise noted, technical terms are used according to conventional usage. Definitions of common terms in molecular biology may be found in Krebs et al., *Lewin's Genes XI*, published by Jones and Bartlett Learning, 2012 (ISBN 1449659853); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 2011 (ISBN 8126531789); and George P. Rédei, *Encyclopedic Dictionary of Genetics, Genomics, and Proteomics*, 2nd Edition, 2003 (ISBN: 0-471-26821-6).

The following explanations of terms and methods are provided to better describe the present disclosure and to guide those of ordinary skill in the art to practice the present disclosure. The singular forms "a," "an," and "the" refer to one or more than one, unless the context clearly dictates otherwise. For example, the term "comprising a cell" includes single or plural cells and is considered equivalent to the phrase "comprising at least one cell." As used herein, "comprises" means "includes." Thus, "comprising A or B," means "including A, B, or A and B," without excluding additional elements. All publications, patent applications, patents, and other references mentioned herein are incorporated by reference in their entirety for all purposes. In case of conflict, the present specification, including explanations of terms, will control.

Although methods and materials similar or equivalent to those described herein can be used to practice or test the disclosed technology, suitable methods and materials are described below. The materials, methods, and examples are illustrative only and not intended to be limiting.

To facilitate review of the various embodiments of this disclosure, the following explanations of specific terms are provided:

Carrier: A substance that can be used as a delivery vehicle (for example, in co-formulation or as inoculant) for microbes, such as the microbes or microbial consortia described herein (also referred to herein as "agro-carriers"). The carrier may be liquid or solid (dry). Exemplary carriers include liquid or dry fertilizers, soil-derived substances (for example, charcoal, clays, turf) organic substances (for example, sawdust, wheat/soy/oat bran, composts,) and inert materials (for example, perlite, vermiculite, bentonite, Azomite®, kaolin, silicates, talc). In some examples, seeds may also be referred to as carriers.

Contacting: Placement in direct physical association, including in either solid and/or liquid form. For example, contacting can occur with one or more microbes (such as the microbes in a microbial consortium) and a carrier or a seed. Contacting can also occur with one or more microbes, microbe/carrier co-formulation, or microbe/seed co-formulation and soil, plants, and/or plant parts (such as foliage, stem, seedling, roots, and/or seeds).

Culturing: Intentional growth of one or more organisms or cells in the presence of assimilable sources of carbon, nitrogen and mineral salts. In an example, such growth can take place in a solid or semi-solid nutritive medium, or in a liquid medium in which the nutrients are dissolved or suspended. In a further example, the culturing may take place on a surface or by submerged culture. The nutritive medium can be composed of complex nutrients or can be chemically defined.

Dipicolinic acid (pyridine-2,6-dicarboxylic acid; DPA): A compound with the structure

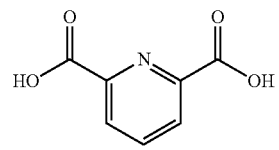 [SMILES: O=C(O)c1cccc(C(=O)O)n1]

In most microbes, DPA is produced by conversion of dihydrodipicolinate to DPA by the enzyme dipicolinate synthase. DPA synthase has two subunits, subunit A (DpaA or spoVFA) and subunit B (DpaB or spoVFB). Exemplary DpaA and DpaB amino acid sequences are provided herein (FIGS. 1 and 2)

Some bacteria (e.g., some *Clostridium*) are able to synthesize DPA, despite lacking identifiable DpaA and DpaB genes. Without being bound by theory, these bacteria are proposed to utilize a structurally related protein, electron transfer flavoprotein (etfA), which is a flavin mononucleotide (FMN) oxidoreductase. EtfA is thought to catalyze the final step in the biosynthesis pathway by converting dihydrodipicolinate to dipicolinic acid (Orsburn et al., *Mol. Microbiol.* 75:178-186, 2010). Alternatively, some bacteria may utilize and iron-sulfur flavoprotein (Isf) in production of DPA.

Heterologous: Originating from a different genetic sources or species. For example, a nucleic acid that is heterologous to a cell originates from an organism or species other than the cell in which it is expressed. Methods for introducing a heterologous nucleic acid into bacterial cells include for example transformation with a nucleic acid, including electroporation, lipofection, and particle gun acceleration.

In another example of use of the term heterologous, a nucleic acid operably linked to a heterologous promoter is from an organism, species, or gene other than that of the promoter. In other examples of the use of the term heterologous, a nucleic acid encoding a polypeptide or portion thereof is operably linked to a heterologous nucleic acid encoding a second polypeptide or portion thereof, for example to form a non-naturally occurring fusion protein.

Isolated: An "isolated" biological component (such as a nucleic acid, protein or organism) has been substantially separated or purified away from other biological components (such as other cells, cell debris, or other proteins or nucleic acids). Biological components that have been "isolated" include those components purified by standard purification methods. The term also embraces recombinant nucleic acids, proteins, or microbes, as well as chemically synthesized nucleic acids or peptides. The term "isolated" (or "enriched" or "purified") does not require absolute purity, and can include microbes or molecules that are at least 50% isolated, such as at least 75%, 80%, 90%, 95%, 98%, 99% or even 100% isolated.

Microbe: A microorganism, including but not limited to bacteria, archaebacteria, fungi, and algae (such as microalgae). In some examples, microbes are single-cellular organisms (for example, bacteria, cyanobacteria, some fungi, or some algae). In other examples, the term microbes includes multi-cellular organisms, such as certain fungi or algae (for example, multicellular filamentous fungi or multicellular algae).

Microbial composition: A composition (which can be solid, liquid, or at least partially both) that includes cells of at least one type (or species) of microbe (or a population of cells of at least one type of microbe). In some examples, a microbial composition comprises cells of one or more types (species) of microbes (or one or more populations of microbes) in a liquid (such as a storage, culture, or fermentation medium or a liquid fertilizer), for example, as a suspension in the liquid. In other examples, a microbial composition includes cells of one or more types (species) of microbes (or one or more populations of microbes) on the surface of or embedded in a solid or gelatinous medium (including but not limited to a culture plate), or a slurry or paste. In other examples, a microbial composition includes cells of one or more types (or species) of microbes (or one or more populations of microbes) in association with a dry material or seed, such as on the surface of or impregnated in a dry material or seed.

Microbial consortium: A mixture, association, or assemblage of cells of two or more microbial species, which in some instances are in physical contact with one another. The microbes in a consortium may affect one another by direct physical contact or through biochemical interactions, or both. For example, microbes in a consortium may exchange nutrients, metabolites, or gases with one another. Thus, in some examples, at least some of the microbes in a consortium are metabolically interdependent. Such interdependent interactions may change in character and extent through time and with changing culture conditions.

Transduced and Transformed: A virus or vector "transduces" a cell when it transfers nucleic acid into the cell. A cell is "transformed" by a nucleic acid transduced into the cell when the DNA becomes replicated by the cell, either by incorporation of the nucleic acid into the cellular genome, or by episomal replication. As used herein, the term transformation encompasses all techniques by which a nucleic acid molecule might be introduced into such a cell, including bacterial conjugation, transfection with viral vectors, transformation with plasmid vectors, and introduction of naked DNA by electroporation, lipofection, and particle gun acceleration.

Vector: A nucleic acid molecule that can be introduced into a host cell, thereby producing a transformed or transduced host cell. Recombinant DNA vectors are vectors including recombinant DNA. A vector can include nucleic acid sequences that permit it to replicate in a host cell, such as an origin of replication. A vector can also include one or more selectable marker genes, a cloning site for introduction of heterologous nucleic acids, a promoter (for example for expression of an operably linked nucleic acid), and/or other genetic elements known in the art. Vectors include plasmid vectors, including plasmids for expression in gram negative and/or gram positive bacterial cells. Exemplary vectors include those for use in *E. coli*.

Viability: Ability of a cell (such as a microbial cell) to grow or reproduce under appropriate conditions for growth or reproduction. In some examples, "survival" or "survivability" refers to the viability of a cell (such as a microbial) cell after a period of storage in a liquid or dry state, alone, in a mixture with other microbial cells, and/or when co-formulated with a carrier or seed.

II. Methods of Identifying Microbes with Viability in Co-Formulations

Disclosed herein are methods of identifying microbes that remain viable or survive when co-formulated with a liquid or solid carrier. The microbes may be individually co-formulated with a carrier or seed (e.g., a single strain or species of microbes is co-formulated with a carrier or seed) or may be part of a consortium or mixture of microbes (e.g., two or more strains or species of microbes) that is co-formulated with a carrier or seed. In other embodiments, the methods include identifying microbes that remain viable or survive for an extended period of time in a consortium (as a standalone consortium or co-formulated with a carrier or seed).

In some examples, microbes identified with the methods disclosed herein, for example, microbes that include one or more DPA synthase genes, express one or more DPA proteins, and/or produce detectable amounts of DPA have improved viability (alone or in a co-formulation) than microbes that do not include one or more DPA synthase genes, do not express one or more DPA synthase proteins, and/or do not produce detectable amounts of DPA. In some examples, the microbes identified with the methods disclosed herein have at least 10% increased viability (for example, at least 20%, at least 30%, at least 40%, at least 50%, at least 60%, at least 70%, at least 80%, at least 90%, at least 1.5-fold, at least 2-fold, at least 5-fold, or more increased viability) compared to a microbe that does not include one or more DPA synthase genes, does not express one or more DPA synthase proteins, and/or does not produce detectable amounts of DPA. Increased viability may include a greater number of viable cells after a set period of time and/or a viability for a longer period of time.

In some embodiments, the methods disclosed herein include identifying microbes that include in their genome one or more genes encoding a DPA synthase, express one or more DPA synthase proteins, and/or produce detectable amounts of DPA. Such microbes are identified as microbes that can remain viable or survive individually or when co-formulated with a liquid or solid carrier (for example, compared to one or more microbes that do not include genes encoding a DPA synthase, do not express one or more DPA synthase proteins, and/or do not produce detectable amounts of DPA). The identified microbes may further be selected for downstream use, such as for co-formulation with a liquid or solid carrier or seed. In some examples, the microbes remain viable or survive (either individually or when co-formulated with a carrier or seed) for at least 1 day, at least 3 days, at least 5 days, at least 7 days, at least 10 days, at least 2 weeks, at least 3 weeks, at least 4 weeks, at least 5 weeks, at least 6 weeks, at least 7 weeks, at least 2 months, at least 3 months, at least 4 months, at least 5 months, at least 6 months, at least 8 months, at least 10 months, at least 1 year, at least 2 years, or more (for example, at least 1-28 days, at least 5-21 days, at least 2-6 weeks, at least 4-8 weeks, at least 2-6 months, at least 3-9 months, at least 4-10 months, at least 6 months to 1 year, at least 1-2 years, or more).

Methods of determining viability or survival of a microbe include detecting growth of the microbe in culture. In some examples, a preparation containing microbial cells (in a liquid or dry state, or in co-formulation with a carrier or seed) is inoculated in a liquid medium, incubated under conditions suitable for microbial growth, and presence and/or amount of microbes after a defined period of time are measured. In other examples a preparation containing microbial cells (in a liquid or dry state, or in co-formulation with a carrier or seed) is streaked on a plate containing solid or semi-solid medium, incubated under conditions suitable for microbial growth, and presence and/or amount of microbes (such as presence, size, and/or number of colonies) are measured. In some examples, the microbes are identified, for example, using PCR methods. Exemplary methods for determining microbial cell viability and identity are provided in Example 1.

In further embodiments, the methods include selecting one or more microbes that include one or more DPA synthase genes, express one or more DPA synthase proteins, and/or produce detectable amounts of DPA and optionally co-formulating the one or more selected microbes with one or more carriers or seeds. In some examples, the methods include preparing a co-formulation of one or more of the selected microbes with one or more carriers or seed. The methods include contacting the one or more microbes with the one or more carriers or seeds, for example, in a solid (dry) or liquid form. In some example, the carrier(s) or seed(s) are contacted with a mixture of microbes. The mixture includes microbes that express DPA synthase or produce DPA (such as microbes selected or produced using the methods described herein, including, but not limited to DFC) and may also include one or more microbes that do not express DPA synthase or produce DPA. In some examples, the carrier is contacted with a liquid that includes about $10^3$-$10^9$ cells/mL or more (e.g., about $1 \times 10^3$ cells/mL, about $5 \times 10^3$ cells/mL, about $1 \times 10^4$ cells/mL, about $5 \times 10^4$ cells/mL, about $1 \times 10^5$ cells/mL, about $5 \times 10^5$ cells/mL, about $1 \times 10^6$ cells/mL, about $5 \times 10^6$ cells/mL, about $1 \times 10^7$ cells/mL, about $5 \times 10^7$ cells/mL, about $1 \times 10^8$ cells/mL, about $5 \times 10^8$ cells/mL, about $1 \times 10^9$ cells/mL, about $5 \times 10^9$ cells/mL, or more) of each microbe.

In some embodiments, a liquid including one or more of the selected microbes (and optionally one or more additional microbes) is placed in contact with one or more dry carriers or seeds. In some examples, the liquid including the microbes is a fresh or frozen bacterial culture or a mixture of fresh or frozen bacterial cultures. In other examples, the liquid including the microbes is a liquid to which freeze-dried microbes have been added. The liquid including the one or more microbes is allowed to soak into the dry carrier or seed. In some examples, an amount of liquid including the one or more microbes is used so that the dry carrier or seed is saturated, for example to provide relatively even distribution of the microbes throughout the carrier or seed. However, non-saturating amounts of liquid may also be used. In non-limiting examples, the amount is about 35 µL/g to 6 mL/g. In some examples, the microbe-impregnated carrier or seed is dried (such as at room temperature or at about 30-35° C.) and stored at ambient temperature (for example, in a closed or air-tight container).

In other embodiments, a liquid including one or more of the selected microbes (and optionally one or more additional microbes) is mixed with one or more liquid carriers. In some examples, the liquid including the microbes is a fresh or frozen bacterial culture or a mixture of fresh or frozen bacterial cultures. In other examples, the liquid including the microbes is a liquid to which freeze-dried microbes have been added. The liquid including the microbes can be mixed with the liquid carrier at any selected amount, for example, from 0.1%-90% (v/v), such as 0.5-1%, 1-5%, 2-10%, 3-6%, 4-8%, 5-15%, 8-20%, 10-25%, 20-40%, 30-50%, 40-60%, 50-75%, or 70-90% (v/v). In some examples, the microbes are mixed with the liquid carrier at about 0.1%, about 0.2%, about 0.5%, about 1%, about 2%, about 3%, about 4%, about 5%, about 6%, about 7%, about 8%, about 9%, about 10%, about 20%, about 30%, about 40%, about 50%, about 60%, about 70%, about 80%, or about 90% (v/v). In one non-limiting example, the mixture of microbes is added to the liquid carrier at 0.5% (v/v) or a ratio of 1:180. In another non-limiting example, the mixture of microbes is added to a concentrated liquid carrier (such as a 10× concentrated liquid carrier) at 90% (v/v) to produce a 1× concentration of the liquid carrier. The amount of microbial cells in the mixture can be adjusted to achieve a desired final concentration of microbial cells, depending on the dilution factor that will be used. The mixture of microbes is stored at ambient temperature (for example, in a closed or air-tight container).

In some embodiments, a dry preparation of microbes (such as freeze-dried microbes) is used in the co-formulation with a dry carrier or seed. In some examples, freeze-dried microbes are mixed with a dry carrier or seed (such as about 40 mg microbes/kg carrier or seed to about 1 g microbes/kg carrier or seed). In some examples, of this embodiment, the freeze-dried microbes are added to a liquid that is then contacted with the dry carrier or seed. In other examples, the freeze-dried microbes are added to a liquid and then contacted with the dry carrier or seed as described above.

A. Detecting DPA Synthase Nucleic Acids

In some embodiments, the methods include identifying presence of one or more DPA synthase nucleic acid molecules (such as DNA, cDNA, or mRNA) in a microbe or population of microbes. In some examples, the methods include detecting one or more DPA synthase genes (such as DpaA and/or DpaB) in the genome of a microbe. In some examples, a microbe includes both DpaA and DpaB genes. Exemplary DPA synthase genes include *B. subtilis* DpaA (GenBank Accession No. NC_000964.3, 1744367-1745260, incorporated herein by reference as present in GenBank on Jun. 3, 2018) and DpaB (GenBank Accession No. NC_000964.3, 1745236-1745865, incorporated herein by reference as present in GenBank on Jun. 3, 2018). In some examples, a DpaA gene encodes a protein shown in FIG. 1 or a protein with at least 20% sequence identity (such as at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, or more) with a protein shown in FIG. 1 (e.g., SEQ ID NOs: 26-39). In some examples, a DpaB gene encodes a protein shown in FIG. 2 or a protein with at least 20% sequence identity (such as at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, or more) with a protein shown in FIG. 2 (e.g., SEQ ID NOs: 42-54. In some examples, a DpaA or DpaB protein has one or more conserved regions identified in the "Consensus60" sequences in FIGS. 1 and 2, respectively (SEQ ID NOs: 40 and 55, respectively).

In other embodiments, the methods include identifying presence of one or more nucleic acids (such as DNA, mRNA, or cDNA) that are involved in an alternative pathway for DPA synthesis. In some examples, the method includes identifying presence or expression of one or more nucleic acids encoding an electron transfer flavoprotein (such as EtfA) or an iron-sulfur flavoprotein (such as Isf).

The electron transfer flavoprotein is a heterodimer consisting of an alpha and a beta subunit, and are part of the adenine nucleotide alpha hydrolase superfamily. Exemplary bacterial EtfA nucleic acid sequences include GenBank Accession Nos. CP000312.1 (2508382-2509389), NC_004578.1 (2407768-2408697), NC_009089.1 (977905-978927), NC_019382.1 (1357738-1356809, complement), NC_003030.1 (2833696-2833268, complement), NC_002971.4 (1062557-1061613, complement), and NC_003063.2 (650447-651376), each of which is incorporated herein by reference as present in GenBank on Jun. 3, 2018. Exemplary bacterial EtfA amino acid sequences include ABG86939, NP_792007.1, YP_001087282.1, YP_006967336.1, NP_349315.1, NP_820116.1, and NP_357016.2, each of which is incorporated herein by reference as present in GenBank on Jun. 3, 2018). Exemplary Isf nucleic acid and protein sequences include GenBank Accession Nos. CP016318 (3060700-3061308) and ARE63607, respectively (incorporated herein by reference as present in GenBank on Jun. 3, 2018) and those shown in FIG. 3 (e.g., SEQ ID NOs: 57-66).

In some examples, DPA synthase nucleic acids (or EtfA or Isf nucleic acids) can be identified by sequence analysis of a microbe (for example, whole genome sequencing and/or sequencing using DPA synthase-specific oligonucleotides). In some examples, the sequence analysis is performed using sequences present in one or more databases, including GenBank (ncbi.nlm.nih.gov/nucleotide/), ENSEMBL (ensembl.org/index.html), IMG (img.jgi.doe.gov), MicrobesOnline (microbesonline.org), SEED (theseed.org), or GOLD (gold.jgi-psf.gov). Exemplary methods for identifying DPA synthase genes are provided in Example 1, below. Similar methods can be used for identifying EtfA or Isf genes.

In some examples, nucleic acids from a microbe or population of microbes are isolated, amplified, or both, prior to detection. In some examples, amplification and detection of expression occur simultaneously or nearly simultaneously. In some examples, nucleic acid expression can be detected by PCR (for example, PCR, real-time PCR, RT-PCR or quantitative RT-PCR). For example, nucleic acids can be isolated and amplified by employing commercially available kits. In an example, the nucleic acids can be incubated with primers that permit the amplification of DpaA and/or DpaB (or EtfA or Isf) nucleic acids, under conditions sufficient to permit amplification of such products. The resulting amplicons can be detected.

In another example, nucleic acids from a microbe or population of microbes are incubated with probes that can bind to DpaA and/or DpaB (or EtfA or Isf) nucleic acid molecules (such as cDNA, genomic DNA, or RNA (such as mRNA)) under high stringency conditions. The resulting hybridization can then be detected. In other examples, a microbe or population of microbes is screened by applying isolated nucleic acid molecules obtained from the microbe(s) to an array. In one example, the array includes oligonucleotides complementary to DpaA and/or DpaB (or EtfA or Isf) nucleic acids. In an example, the microbial nucleic acid molecules are incubated with an array including oligonucleotides complementary to DpaA and/or DpaB (or EtfA or Isf) for a time sufficient to allow hybridization between the isolated nucleic acid molecules and oligonucleotide probes, thereby forming isolated nucleic acid molecule:oligonucleotide complexes. The isolated nucleic acid molecule:oligonucleotide complexes are then analyzed to determine if the nucleic acids are present in the sample.

B. Detecting DPA Synthase Proteins

As an alternative, or in addition to detecting DPA synthase nucleic acids, proteins can be detected using methods such as immunoassays (such as Western blot, immunohistochemistry, flow cytometry, or ELISA) or mass spectrometry. In some examples, a DpaA protein includes a protein with at least 20% sequence identity (such as at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, or more) with a protein shown in FIG. 1 (e.g., SEQ ID NOs: 26-39). In some examples, a DpaB protein includes a protein with at least 20% sequence identity (such as at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, or more) with a protein shown in FIG. 2 (e.g., SEQ ID NOs: 42-54). In some examples, a DpaA or DpaB protein has one or more conserved regions identified in the "Consensus60" sequences in FIGS. 1 and 2, respectively (SEQ ID NOs: 40 and 55, respectively). In other examples, an Isf protein includes a protein with at least 20% sequence identity (such as at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, or more) with a protein shown in FIG. 3 (e.g., SEQ ID NOs: 57-66).

In some examples, proteins are purified before detection. In one example, DpaA and/or DpaB (or Isf) proteins can be detected by incubating a microbial sample with an antibody that specifically binds to DpaA and/or DpaB (or Isf). The antibody ("primary antibody") can include a detectable label. For example, the primary antibody can be directly labeled, or the sample can be subsequently incubated with a secondary antibody that is labeled (for example with a fluorescent label). The label can then be detected, for example by microscopy, ELISA, flow cytometry, or spectrophotometry. In another example, the sample is analyzed by Western blotting for detecting expression of DpaA and/or DpaB proteins. Antibodies for DpaA, DpaB, or Isf can be generated by one of ordinary skill in the art, for example, using the amino acid sequences in FIGS. 1-3.

Suitable labels for the antibody or secondary antibody include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary magnetic agent is gadolinium, and non-limiting exemplary radioactive labels include $^{125}$I, $^{131}$I, $^{35}$S or $^{3}$H.

C. Detecting DPA

In some embodiments, the methods include identifying a microbe or population of microbes that produces DPA (such as detectable levels of DPA). In some examples, the methods include detecting at least 1 nM DPA (such as at least 2 nM, at least 5 nM, at least 10 nM, at least 25 nM, at least 50 nM, at least 100 nM, at least 200 nM, at least 500 nM DPA, or more). In one example, the methods include detecting DPA using a terbium-DPA fluorescence assay (see, e.g., Rosen, Anal. Chem. 69:1082-1085, 1997; Pellegrino et al., Anal.

Chem. 70:1755-1760, 1998; Ammann et al., *Int. J. Microbiol.* 2011:435281, 2011). Briefly, contacting DPA with terbium(III) forms a complex that has increased fluorescence compared to terbium(III), allowing detection and/or quantitation of DPA in a sample. An exemplary Terbium-DPA assay is described in Example 1.

III. Microbes and Co-Formulations

Disclosed herein are microbes that include one or more DPA synthase genes in their genome, express one or more DPA synthase proteins, and/or produce DPA. In some examples, the microbes are modified to include one or more DPA synthase genes in their genome, express one or more DPA synthase proteins, and/or produce DPA. Also disclosed are co-formulations of the microbes with one or more carriers or seeds.

A. Microbes

Microbes that possess one or more DPA synthase genes, express one or more DPA synthase proteins, and/or produce DPA include, but are not limited to, *Bacillus amyloliquefaciens, Bacillus flexus, Bacillus licheniformis, Bacillus megaterium, Bacillus subtilis, Bacillus* sp. (closely related to *B. kochii, B. pocheonensis,* and *Bacillus* sp. (strain R-27341)), *Clostridium beijerinckii, Oceanobacillus oncorhynchi, Paenibacillus chibensis, Paenibacillus cookii, Paenibacillus lautus, Virgibacillus halophilus, Paenibacillus azoreducens,* and *Bacillus firmus*. In some examples, these bacteria include those described in PCT Publication No. WO 2018/045004 (incorporated herein by reference in its entirety). Additional microbes include those listed in Tables 25 and 26. In some examples, these microbes also have sporulation ability; however, sporulation ability and presence of identifiable DPA synthase genes or DPA production are not completely concordant (see, e.g., Table 6).

In additional embodiments, disclosed are compositions including microbes that possess one or more DPA synthase genes, express one or more DPA synthase proteins, and/or produce DPA, including those referred to herein as Dry Formulation Consortium (DFC). The microbes in DFC include, but are not limited to *Bacillus amyloliquefaciens, Bacillus firmus, Bacillus flexus, Bacillus licheniformis, Bacillus megaterium, Bacillus pumilus, Bacillus koreensis, Bacillus drentensis, Bacillus subtilis, Clostridium bifermentans, Clostridium beijerinckii, Clostridium pasteurianum, Lactobacillus paracasei, Fontibacillus* sp. (*panacisegetis*), *Oceanobacillus oncorhynchi, Paenibacillus lautus, Paenibacillus azoreducens, Paenibacillus chibensis, Paenibacillus cookii, Paenibacillus* sp. (*chitinolyticus*), *Paenibacillus* sp. (P1XP2), *Pseudomonas* sp., and *Streptomyces griseus*. In one embodiment, the composition includes cells of microbial species deposited with the American Type Culture Collection (ATCC, Manassas, VA) on May 16, 2019 and assigned deposit number PTA-125924.

One of ordinary skill in the art will recognize that identification of microbes, particularly at the species or strain level, is not always possible. In some examples, the microbes in the compositions described herein were analyzed by 16S rDNA sequencing and whole genome sequencing followed by comparison to sequences in public databases. However, due to limitations of information in sequence databases (including little or no information for some species or strains and/or changes in nomenclature over time) it can be challenging to provide definitive species or strain identifications. Thus, in some embodiments, the microbial species included in the disclosed compositions are identified by their sequence identity to the 16S rDNA sequences provided herein (SEQ ID NOs: 3-25). In some examples, the disclosed microbial consortia or compositions include, consist essentially of, or consist of two or more (such as 5 or more, 10 or more, 15 or more, 20 or more, or all) of the microbes having 16S rDNA sequences with at least 95% identity (such as at least 96%, 97%, 98%, 99%, or more) to SEQ ID NOs: 3-25.

Microbes that possess one or more DPA synthase genes, express one or more DPA synthase proteins, and/or produce detectable amounts of DPA also include microbes that do not naturally have one or more DPA synthase genes, express one or more DPA synthase proteins, and/or produce DPA, but are modified to do so. In some examples, a microbe that does not naturally have one or more DPA synthase genes, express one or more DPA synthase proteins, and/or produce DPA is modified to express one or more heterologous DPA synthase genes, such as DpaA and/or DpaB or one or more Isf genes. Exemplary DpaA and DpaB genes and proteins and Isf genes and proteins are described in Section II and FIGS. 1-3, including SEQ ID NOs: 26-67).

Bacteria that may be modified to express one or more heterologous DPA synthase genes include, but are not limited to, *Azotobacter* (such as *Azotobacter vinelandii*), *Clostridium* (such as *Clostridium pasteurianum*), *Streptomyces* (such as *Streptomyces griseus, Streptomyces venezuelae, Streptomyces pratensis*), *Sporolactobacillus* spp. (e.g., *Sporolactobacillus dextrus*). *Sporosarcina* spp. (e.g., *Sporosarcina halophila*), *Desulfotomaculum* spp. (e.g., *Desulfotomaculum guttoideum*). *Nocardiopsis* Spp. (e.g., *Nocardiopsis sinuspersici*). *Promicromonospora* spp. (e.g., *Promicromonospora enterophila, Promicromonospora Brevibacillus* spp. (e.g., *Brevibacillus centrosporus*), *Rummeliibacillus* spp. (e.g., *Rummeliibacillus pycnus*), *Lysinibacillus* spp., *Terribacillus* spp. (e.g., *Terribacillus shanxiensis*), *Micromonospora* spp. (e.g., *Micromonospora fulva, Micromonospora palomenea*). *Saccharopolyspora* spp. (e.g., *Saccharopolyspora spinose, Saccharopolyspora indica*), and *Fontibacillus* spp. (e.g., *Fontibacillus panacisegetis*). In some examples, these bacteria include those described in PCT Publication No. WO 2018/045004 (incorporated herein by reference in its entirety).

In some examples, the heterologous DpaA and/or DpaB gene is placed under control of a promoter. In some examples, the promoter is a constitutive promoter, while in other examples, the promoter is inducible (for example, an inducible T7 promoter). In additional examples, the promoter is an arabinose-inducible promoter (for example, the pBAD system), a lac promoter (direct IPTG/lactose induction), a trc promoter (direct IPTG/lactose induction), a tetracycline-inducible promoter, or a pho promoter (phosphate deprivation induced). The heterologous DpaA and/or DpaB gene may be included in a vector, for example operatively linked to a promoter. Similar methods can be used for EtfA or Isf genes.

Multiple genes (such as two or more DPA synthase and/or Isf genes) can be expressed simultaneously in bacteria. To ensure adequate and coordinate production of multiple enzymes from a single pathway, each nucleic acid encoding a heterologous gene is optionally placed under control of a single type of promoter, such as the inducible T7 promoter. One example is the Duet™ vectors (Novozymes), which are designed with compatible replicons and drug resistance genes for effective propagation and maintenance of four plasmids in a single cell. This allows for the coexpression of up to eight different proteins. In other examples, the vector is a pET vector, such as a pET21 or pET28 vector. pET and pET-based vectors are commercially available, for example from Novagen (San Diego, CA), or Clontech (Mountain View, CA).

In one example, the vector is pET21a or pET28a. In some examples, the pET vector includes a resistance marker (e.g. ampicillin or kanamycin resistance) and a T7 promoter. The multiple cloning site has been manipulated such that more than one gene (such as 2, 3, 4, or more) can be expressed from a single vector. In some examples, the genes are expressed as a multicistronic product (for example, a bi-cistronic, tri-cistronic, etc. product), with a single mRNA and multiple polypeptides produced. In other examples, the genes are expressed as multiple monocistronic products, with an individual mRNA and polypeptide produced for each gene. Appropriate vectors can be selected depending on the gene(s) to be expressed and the host cell being transformed.

In some examples, a plasmid is introduced extrachromosomally and replicated within the host microbe. In other examples, after introduction of the plasmid, a double homologous recombination event occurs and the one or more genes are inserted into the genome.

Transformation of a bacterial cell with recombinant DNA can be carried out. Where the host is bacterial, competent cells which are capable of DNA uptake can be prepared from cells harvested after exponential growth phase and subsequently treated by the $CaCl_2$ method using procedures well known in the art. Alternatively, $MgCl_2$ or RbCl can be used. Bacteria can also be transformed by electroporation, conjugation, or transduction.

B. Carriers and Seed Treatments

Disclosed herein are methods for co-formulating one or more microbes with one or more carriers and compositions including one or more microbes and one or more carriers. The carrier may be liquid or solid (dry). Carriers include liquid or dry fertilizers (such as fertilizers including urea, potash, ammonium phosphate, and/or ammonium nitrate), soil-derived substances (for example, clay, peat, coal, inorganic soil) organic substances (for example, charcoal, sawdust, wheat/soy/oat bran, compost, coco coir), and/or inert materials (for example, perlite, vermiculite, bentonite, Azomite®, kaolin, silicates, pumice, talc). Exemplary carriers include Azomite®, perlite, biochar, dry fertilizers (such as urea, MOP, or MAP), liquid fertilizer (such as UAN), and dust control chemicals (such as those available from Arr-Maz, FL, USA). Additional exemplary carriers include montmorillonite, attapulgite, hydrous aluminosilicate (Agsorb Products Group, IL, USA), akadama (Eastern Leaf Inc, CA, USA), Seramis Clay granules (Greens hydroponics, UK), Aquasmart™ Pro (Aquasmart, TX, USA), Pyro-Gro (Green Air products, OR, USA), crushed lava, clay pebbles).

In some embodiments, co-formulations with carriers include the consortium of 22 microbes described in WO 2018/045004 (incorporated herein by reference in its entirety; referred to herein as AMC1) and one or more of the carriers described herein. In other embodiments, co-formulations with carriers include the consortium of 23 microbes disclosed herein (e.g., the microbes listed in Table 26 or ATCC deposit PTA-125924) and one or more carriers. Co-formulations also include one or more (such as 1, 2, 3, 4, 5, 6, 7, 8, 9, 10, 11, 12, 13, 14, 15, 16, 17, 18, 19, 20, 21, 22, 23, or more) microbes and one or more of the carriers described herein. In some examples, a co-formulation includes at least one microbe that includes or expresses one or more DPA synthase and/or Isf gene(s) (or produces DPA) and a carrier. In other examples, a co-formulation includes at least one microbe that includes or expresses DPA synthase gene(s) or produces DPA and at least one microbe that does not include or express DPA synthase gene(s) or does not produce DPA with a carrier. Methods of co-formulating a carrier and one or more microbes include contacting the one or more carriers with the one or more microbes. In some examples, the one or more microbes are in liquid form (e.g., are in a liquid medium) or are in a solid or dry form.

Also disclosed herein are methods for treating seeds with one or more microbes (e.g., co-formulating one or more microbes with one or more seeds) and compositions including one or more microbes and one or more seeds. In such embodiments, the seeds are the "carrier" for the microbes. In some embodiments, seed treatments include the consortium of 22 microbes described in WO 2018/045004 (incorporated herein by reference in its entirety) and one or more seeds. In other embodiments, seed treatments include the consortium of 23 microbes disclosed herein (e.g., the microbes listed in Table 26 or ATCC deposit PTA-125924) and one or more seeds. In other examples, a co-formulation includes at least one microbe that includes or expresses one or more DPA synthase and/or Isf gene(s) (or produces DPA) and a seed. In other examples, a co-formulation includes at least one microbe that includes or expresses DPA synthase gene(s) or produces DPA and at least one microbe that does not include or express DPA synthase gene(s) or does not produce DPA and a seed. Exemplary seeds that can be treated with the one or more microbes include, but are not limited to, corn seeds, sunflower seeds, canola seeds, wheat seeds, cucumber seeds, tomato seeds, rice seeds, and cotton seeds.

In some examples, microbe-treated seeds are prepared by applying microbes directly to seeds (e.g., contacting seed with one or more microbes). In other examples, microbe-treated seeds are prepared by applying the microbes as an overcoat to seeds that have been previously treated with an insecticide and/or fungicide (e.g., contacting insecticide and/or fungicide treated seed with one or more microbes). In yet further examples, microbe-treated seeds are prepared by mixing the microbes with an insecticide and/or fungicide (such as an insecticide/fungicide slurry) and applying the mixture to the seeds (e.g., contacting seed with a mixture of insecticide and/or fungicide and one or more microbes). Exemplary insecticides and fungicides that can be used in combination with the microbes include, but are not limited to, metalaxyl, trifloxystrobin, ipconazole, clothianidin, thiamethoxam, fludioxonil, mefenoxam, azoxystrobin, thiabendazole, pyraclostrobin, imidacloprid, fluxapyroxad, and/or sedexane. In some examples, the one or more microbes applied to the seed are in liquid form (e.g., are in a liquid medium) or are in a solid or dry form. Methods of preparing treated seeds include, but are not limited to those described in *Seed Treatment: Oregon Pesticide Applicator Training Manual* (Paulsrud et al., Urbana, Illinois, 2001) and Example 13.

IV. Methods of Use

The disclosed microbial compositions, alone or in co-formulation with one or more liquid or dry carriers, can be used to treat soil, plants, or plant parts (such as roots, stems, foliage, seeds, or seedlings). In other examples, the disclosed microbial compositions can be used in the form of treated seeds.

In some examples, treatment with the disclosed compositions and/or carriers or seeds treated with the disclosed compositions improve plant growth, improve stress tolerance, and/or increase crop yield. In some embodiments the methods include contacting soil, plants (such as plant foliage, stems, roots, seedlings, or other plant parts), or seeds with a microbial composition or co-formulation disclosed herein. In other embodiments, the methods include planting seeds treated with the disclosed compositions. The methods may also include growing the treated plants, plant parts, or seeds and/or cultivating plants, plant parts, or seeds in the treated soil.

In some examples, the amount of the composition(s), alone or as a co-formulation of one or more microbes and carriers or seeds to be applied (for example, per acre or hectare) is calculated and the composition is diluted in water (or in some examples, liquid fertilizer) to an amount sufficient to spray or irrigate the area to be treated (if the composition is a liquid). The composition can be applied at the time of seed planting at a rate of 0.5-2 liters per acre (such as 0.5 L/acre, 1 L/acre, 1.5 L/acre, or 2 L/acre). The composition can also be applied to the soil (e.g., near the plant roots) or plant one or more times during growth, in the same or a different amount. In other examples, the composition can be mixed with diluted herbicides, insecticides, pesticides, or plant growth regulating chemicals. If the composition to be applied is a solid (such as a dry formulation), the solid can be applied directly to the soil, plants, or plant parts or can be suspended or dissolved in water (or other liquid) prior to use.

In some examples, treatment of soil, seeds, plants, or plant parts with a disclosed composition increases plant growth (such as overall plant size, amount of foliage, root number, root diameter, root length, production of tillers, fruit production, pollen production, and/or seed production) by at least about 5% (for example, at least about 10%, at least about 30%, at least about 50%, at least about 75%, at least about 100%, at least about 2-fold, at least about 3-fold, at least about 5-fold, at least about 10-fold, or more). In other examples, the disclosed methods result in increased crop production by about 10-75% (such as about 20-60% or about 30-50%) compared to untreated crops. Other measures of crop performance include quality of fruit, yield, starch or solids content, sugar content or brix, shelf-life of fruit or harvestable product, production of marketable yield or target size, quality of fruit or product, grass tillering and resistance to foot traffic in turf, pollination and fruit set, bloom, flower number, flower lifespan, bloom quality, rooting and root mass, crop resistance to lodging, abiotic stress tolerance to heat, drought, cold and recovery after stress, adaptability to poor soils, level of photosynthesis and greening, and plant health. To determine efficacy of products, controls include the same agronomic practices without addition of microbes, performed in parallel.

The disclosed methods and compositions and/or co-formulations can be used in connection with any crop (for example, for direct crop treatment or for soil treatment prior to or after planting). Exemplary crops include, but are not limited to alfalfa, almond, banana, barley, broccoli, cabbage, cannabis, canola, carrots, citrus and orchard tree crops, corn, cotton, cucumber, flowers and ornamentals, garlic, grapes, hops, horticultural plants, leek, melon, oil palm, onion, peanuts and legumes, pineapple, poplar, pine and wood-bearing trees, potato, raspberry, rice, sesame, sorghum, soybean, squash, strawberry, sugarcane, sunflower, tomato, turf and forage grasses, watermelon, wheat, and eucalyptus.

EXAMPLES

The following examples are provided to illustrate certain particular features and/or embodiments. These examples should not be construed to limit the disclosure to the particular features or embodiments described.

Example 1

Materials and Methods

Isolation and Identification of Microbes: All microbes were derived from Agrinos microbial collection (AMC) and previously described in WO 2018/045004, except for four additional microbes described herein. These additional microbes were isolated as described below.

The bacteria *Streptomyces pratensis* and *Streptomyces venezuelae* were isolated from bulk soil (N38° 38' 49.402", W121° 40" 5.775"). Briefly, the soil sample was suspended in a sterile phosphate buffered saline-TWEEN® 80 solution before serial dilution and plating onto several types semi-solid media. *S. pratensis* and *S. venezuelae* were isolated from *Azotobacter* medium agar with mannitol (HIMEDIA #M372) plates after incubation for up to 3 days at 30° C. The strains were repeatedly streaked onto semi-solid media MP (see below) until isogenic.

*Bacillus firmus* was isolated from a sample of HYT® A (Agrinos AS) which had been previously mixed with fertilizer (UAN32) at a ratio of 1:180. After three weeks incubation at room temperature, aliquots of the mixture were plated on several types of semi-solid media and incubated for up to 3 days at 30° C. A *B. firmus* colony was collected from a Pikovskaya's medium agar plate (HIMEDIA #M520). The strain was repeatedly streaked onto semi-solid media MP (see below) until isogenic.

*Paenibacillus azoreducens* was isolated from a sample of HYT® A (Agrinos AS). *P. azoreducens* was isolated as a colony growing on 1-10 mM ammonium sulfate agar media (0.585 g/L NaCl, 0.075 g/L KCl, 0.147 g/L $CaCl_2$, 0.049 g/L $MgSO_4$, 1.32-0.132 g/L $(NH_4)_2SO_4$, 0.054 g/L $KH_2PO_4$ in HEPES buffer pH 7.5). The strain was repeatedly streaked onto semi-solid media MP (see below) until isogenic.

Taxonomic classification of newly described microbes: For all four newly described strains, whole-genome sequencing of biologically pure isolates was performed as described below. De novo genome assembly was performed with Hierarchical Genome Assembly Process (HGAP, Pacific Biosciences, Menlo Park, CA USA).

Taxonomic identifications were primarily made using 16S ribosomal RNA (rRNA) sequences. 16S rRNA sequences were first identified within the de novo genome assembly using RNAmmer (cbs.dtu.dk/services/RNAmmer/). 16S sequences were then classified using pairwise alignment with NCBI BLASTn, the Ribosomal Database Project (RDP) Nave Bayesian Classifier (Wang et al. *Appl. Environ. Microbiol.* 73:5261-5267, 2007), and Greengenes de novo phylogenetic tree construction and rank mapping (DeSantis et al. *Appl. Environ. Microbiol.* 72:5069-502, 2006). Species assignments were then made using a consensus of the three methods.

Based on the above, microbial identifications were made as follows:

*Streptomyces pratensis*. Using 16S sequences, a whole genome taxonomic classification was also performed. Protein coding sequences were identified using Prodigal (Hyatt et al. *BMC Bioinformatics,* 11:119, 2010). This classification utilized a set of 49 conserved Clusters of Orthologous Groups (COG) families (Tatsuov et al. *Science* 278:631-637, 1997) to find the matching corresponding set of sequences for a specific genome. The sequences from the selected genome were then inserted into the reference alignments, the closest neighbors were extracted and concatenated, and a tree was rendered from them using FastTree2 (an approximate maximum likelihood method; Price et al. *PLoS One* 5:e9490, 2010). This rigorous classification method selected *Streptomyces pratensis* as the most appropriate reference species. The reference genome for *Streptomyces pratensis* ATCC 33331 was downloaded from NCBI RefSeq and aligned against the obtained whole genome sequence using MUMmer mummer.sourceforge.net/). The alignment revealed broad global agreement and confirmed that the two are very closely related on a genome-wide scale. A consensus 16S sequence is provided as SEQ ID NO: 1.

*Streptomyces venezuelae*. The results of all analyses strongly supported the identification of this isolate as *S. venezuelae*. A consensus 16S sequence is provided as SEQ ID NO: 2.

*Bacillus firmus*. The results of all analyses strongly supported the identification of this isolate as *B. firmus*. A consensus 16S sequence is provided as SEQ ID NO: 3.

*Paenibacillus azoreducens*. The results of all analyses strongly supported the identification of this isolate as *P. azoreducens*. A consensus 16S sequence is provided as SEQ ID NO: 4.

Identification of Microbial Metabolic Activity Potential: All potential microbial metabolic activities were assessed using laboratory assays as described in WO 2018/045004, incorporated herein by reference in its entirety. In order to determine whether the microbe reduces sulfur-containing compounds to sulfides during the process of metabolism, bioMérieux's API® identification products were used according to the manufacturer's recommendations (bioMérieux, Inc., Durham, NC USA). The results of the key metabolic activity profiling for newly identified microbes are shown in Table 1.

Evaluation of di picolinic acid (DPA) production in bacteria: Evaluation of DPA production in bacterial strains of interest was performed with a terbium-DPA fluorescence assay, essentially as described by Rosen (*Anal. Chem.* 69:1082-1085, 1997); Pellegrino et al. (*Anal. Chem.* 70:1755-1760, 1998); and Ammann et al. (*Int. J. Microbiol.* 2011:435281, 2011). Briefly, each isogenic strain was grown on agar media (see Table 2) either aerobically or anaerobically. Aerobic strains were grown at 30° C. for up to 3 days, while anaerobic strains were grown at 35° C. in BD GasPak EZ container systems (Becton, Dickinson and Company, Franklin Lakes, NJ USA) with Pack-Anaero anaerobic gas generating sachets (Mitsubishi Gas Chemical Company, Inc., Tokyo, Japan) for up to 3 days. For the DPA assay, approximately 5 µL of bacteria was taken from a colony growing on a plate and resuspended in 10 mL of sodium acetate buffer (0.2 M, pH 5). The suspension was autoclaved for 15 min at 121° C., 15 psig and cooled at room temperature for about 30 min. Equal volumes of the autoclaved suspension and a 30 µM Terbium(III) chloride hexahydrate (Sigma-Aldrich, Saint Louis, MO USA) solution were subsequently mixed. Fluorescence was then measured (272 nm excitation, 545 nm emission) using a the Cytation 5 Imaging Reader (BioTek, Winooski, VT USA).

Culturing of bacteria used in this study on semi-solid media: Isogenic bacterial strains stored at −80° C. as master cell banks were grown on agar media (Table 2) until formation of distinct colonies was observed. Briefly, aerobic strains were grown at 30° C. for up to 3 days, while anaerobic strains were grown at 35° C. in BD GasPak EZ container systems (Becton, Dickinson and Company, Franklin Lakes, NJ USA) with Pack-Anaero anaerobic gas generating sachets (Mitsubishi Gas Chemical Company, Inc., Tokyo, Japan) for up to 3 days.

TABLE 1

Metabolic activities of new microbial isolates

| Microbe | N metab. | Salt tolerant | Mineral solubil. | Cellulolytic/ Chitinolytic | Other Plant Beneficial Activity | Sulfur metab. | Iron metab./ Siderophore |
|---|---|---|---|---|---|---|---|
| *Streptomyces venezuelae* | N, D | ≥2.5% | | Chitin + Cellulose | M + IAA | | Siderophore biosynthesis and transport |
| *Streptomyces pratensis* | N | ≥2.5% | | Chitin + Cellulose | M + IAA | | Siderophore biosynthesis and transport |
| *Bacillus firmus* | N | <5% | | Cellulose | M + IAA | | Siderophore transport |
| *Paenibacillus azoreducens* | N | <2.5% | P, Ca | | IAA | H2S prod. | Siderophore transport |

D: denitrification,
N: Nitrogen fixation,
P: phosphate,
Ca: calcium,
IAA: Indole-3-acetic acid production,
M: Malic acid assimilation,
H2S: production of hydrogen sulfide

TABLE 2

Agar media used to culture microbes

| Genus | Agar-based medium* |
|---|---|
| Bacillus spp. | MP, NA (amyloliquefaciens; flexus; licheniformis; subtilis), BHI (subtilis; licheniformis; flexus), RCM (firmus; sp.(pocheonensis)), YPD (megaterium; amyloliquefaciens), RhX (amyloliquefaciens) |
| Lactobacillus spp. | RCM, MP, MRS |
| Virgibacillus spp. | YPD, MP |
| Paenibacillus spp. | BHI, MP, NA (cookii, lautus), RCM (azoreducens), R2A (chibensis) |
| Clostridium spp. | RCM (pasteurianum; beijerinckii), AMAS (pasteurianum), NA (beijerinckii), MP (pasteurianum; beijerinckii), MP |
| Oceanobacillus spp. | BHI, RhX, NA, MP |
| Acetobacter spp. | RCM, YPD, MP |
| Pseudomonas spp. | MP, YPD, BHI (putida), RCM (sp. (fluorescens)) |
| Streptomyces spp. | MP, BHI, NA (pratensis), YPD (griseus) |
| Azotobacter spp. | MP, AMAS, RhX |

*NA: nutrient agar (BD #213000); YPD: yeast peptone dextrose (BD #242720); BHI: Brain Heart infusion agar (Teknova, CA, USA); RhX: 111 Rhizobium × medium (ATCC); AMAS: azotobacter medium agar (HIMEDIA #M372); RCM: reinforce Clostridium medium (BD#218081); MRS: Lactobacilli MRS (BD# 288210); R2A: R2A agar (HIMEDIA #SMEB962), MP: Molasses medium agar (2% w/v molasses, 0.15 g/L $MgSO_4$, 0.1 g/L $CaCl_2$, 0.12 g/L $FeSO_4$, 1 g/L $K_2SO_4$, 5 g/L Yeast extract, 10 g/L peptone, 5 g/L NaCl, 0.1 g/L $NaMoO_4$, 0.01 g/L $MnCl_2$, 0.03 g/L $KH_2PO_4$, 0.03 g/L $Na_2HPO_4$ and 15 g/L Agar)

Culturing of individual bacteria strains used in this study in liquid media: Selected colonies from agar-grown strains were inoculated in appropriate sterilized liquid media (Table 3) and incubated for up to 3 days. Aerobic strains were cultured at 30° C. with shaking (125-175 rpm) while anaerobic strains were cultured under N2 gas in sealed serum bottles or Hungate tubes at 35° C. with no agitation. When needed, microbial consortia were produced by mixing equal volumes of individually grown strains. A typical result illustrating the number of cells per mL per strain (see below) is summarized in Table 4. Microbial content was determined by Droplet Digital PCR (ddPCR) using Supermix For Probes (Bio-Rad Laboratories, Hercules, CA), as described in WO 2018/045004.

TABLE 3

Liquid media used to culture microbes

| Genus | Liquid medium* |
|---|---|
| Bacillus spp. | BHI (flexus; licheniformis; sp.(pocheonensis); subtilis), YPDS (megaterium; amyloliquefaciens), NB (firmus) |
| Lactobacillus spp. | RCM |
| Virgibacillus spp. | BHIS |
| Paenibacillus spp. | BHI (chibensis; cookii; lautus), NB (azoreducens) |
| Clostridium spp. | RCM |
| Oceanobacillus spp. | BHIS |
| Acetobacter spp. | YPD |
| Pseudomonas spp. | YPDS 0.5% |
| Streptomyces spp. | YEME |
| Azotobacter spp. | MP |

*YPD: yeast peptone dextrose (BD #242720); YPDS: yeast peptone dextrose (BD #242720) supplemented with 0.5 g/L NaCl; BHI: Brain Heart infusion (Teknova, CA, USA); RCM: reinforce clostridium medium (BD#218081); ); BHIS: Brain Heart infusion (Teknova, CA, USA) supplemented with 45 g/L NaCl; RCM: reinforce clostridium medium (BD#218081); MP: Molasses medium (2% w/v molasses, 0.15 g/L $MgSO_4$, 0.1 g/L $CaCl_2$, 0.12 g/L $FeSO_4$, 1 g/L $K_2SO_4$, 5 g/L Yeast extract, 10 g/L peptone, 5 g/L NaCl, 0.1 g/L $NaMoO_4$, 0.01 g/L $MnCl_2$, 0.03 g/L $KH_2PO_4$ and 0.03 g/L $Na_2HPO_4$); YEME: Yeast extract-malt extract medium (3 g/L yeast extract, 5 g/L bacto-peptone; 3 g/L malt extract; 10 g/L glucose; 340 g/L sucrose 5 mM $MgCl_2$); NB: nutrient broth (BD #234000)

TABLE 4

Typical number of bacteria cells per mL of final liquid formulation by mixing individually cultured strains.

| Microorganisms | Number of bacteria cells per mL of final liquid formulation (mix of individuals) |
|---|---|
| Bacillus megaterium | 2.53E+07 |
| Lactobacillus paracasei/casei | 7.66E+07 |
| Clostridium beijerinckii | 1.97E+07 |
| Acetobacter pasteurianus | 4.58E+07 |
| Lactobacillus buchneri | 1.77E+07 |
| Bacillus subtilis | 5.26E+07 |
| Paenibacillus cookii | 9.14E+07 |
| Lactobacillus vini | 9.06E+07 |
| Bacillus licheniformis | 5.00E+08 |
| Paenibacillus lautus | 5.16E+07 |
| Oceanobacillus oncorhynchi | 2.12E+07 |
| Bacillus amyloliquefaciens | 8.30E+07 |
| Bacillus sp. | 1.26E+08 |
| Pseudomonas putida | 1.02E+08 |
| Pseudomonas sp. | 1.96E+08 |
| Streptomyces griseus | 3.76E+07 |
| Paenibacillus chibensis | 9.34E+07 |
| Bacillus flexus | 5.88E+07 |
| Clostridium pasteurianum | 3.29E+07 |
| Azotobacter vinelandii | 6.02E+07 |
| Virgibacillus halophilus | 1.95E+07 |
| Lactobacillus delbrueckii | 3.36E+07 |

Production of co-cultivated microbial consortia by fermentation: Both aerobic and/or anaerobic bacteria were cultured in medium containing 2% molasses supplemented with essential elements such as phosphates, sodium, potassium and chlorides (in the form of commercially available Phosphate Buffered Saline) as well as amino acids, nitrogen and peptides/proteins in the form of food grade Whey powder (0.1% w/v) and non-GMO soybean extract produced enzymatically (0.25% w/v; Ferti-Nitro Plus Plant N; Ferti-Organic, Brownsville, TX USA). Sodium chloride concentrations ranged from 0-4% w/v. Strains from Table 4 described above (referred to herein as AMC1) were inoculated into 2 L DASGIP bioreactors (Eppendorf North America Hauppauge, NY) with a 1.5 liter working volume at a final inoculation of $OD_{600}$ for each strain ranging between 6.67E-05 to 6.67E-04. Ammonium hydroxide and phosphoric acid were used as base and acid solutions respectively to maintain pH between pH 5.5 and 6.9. Temperature was controlled between 28° C. and 35° C. Anaerobic fermentations were continuously sparged with N2 gas to maintain an anaerobic environment while sparged air was used in aerobic fermentations as a source of oxygen for the microbes during the length of fermentation (typically up to 3 days). For some experiments, after fermentation batches containing different strains were pooled to generate one complete bacterial mixture of 22 strains. A typical result illustrating the number of cells per mL per strain (see below) is summarized in Table 5. Microbial content in fermentates was determined by Droplet Digital PCR (ddPCR) using Supermix For Probes (Bio-Rad Laboratories, Hercules, CA), as described describes in WO 2018/045004.

TABLE 5

Typical number of bacteria cells per mL of final liquid formulation through co-cultivation

| Microorganisms | Number of bacteria cells per mL of final liquid formulation (co-culture) |
|---|---|
| Bacillus megaterium | 1.40E+04 |
| Lactobacillus paracasei/casei | 9.60E+05 |
| Clostridium beijerinckii | 1.60E+07 |
| Acetobacter pasteurianus | 1.20E+07 |
| Lactobacillus buchneri | 1.00E+05 |
| Bacillus subtilis | 1.30E+06 |
| Paenibacillus cookii | 6.60E+03 |
| Lactobacillus vini | 8.20E+04 |
| Bacillus licheniformis | 9.30E+05 |
| Paenibacillus lautus | 2.00E+09 |
| Oceanobacillus oncorhynchi | 2.00E+09 |
| Bacillus amyloliquefaciens | 6.00E+05 |
| Bacillus sp. | 3.20E+05 |
| Pseudomonas putida | 2.30E+07 |
| Pseudomonas sp. | 1.20E+07 |
| Streptomyces griseus | 7.50E+06 |
| Paenibacillus chibensis | 5.80E+03 |
| Bacillus flexus | 6.00E+06 |
| Clostridium pasteurianum | 4.80E+06 |
| Azotobacter vinelandii | 1.30E+07 |
| Virgibacillus halophilus | 6.10E+06 |
| Lactobacillus delbrueckii | 2.00E+06 |

Production of freeze-dried microbial consortium: In some experiments, the consortium of microbes produced was freeze-dried prior to experimentation in co-formulation with agro-carriers. Consortia were produced either by pooling an equal volume of individually cultured bacteria or using co-cultured fermentates (described above). Freeze-drying was performed essentially as described in WO 2018/045004. Briefly, freeze-dried microbial formulations were produced by mixing the liquid microbial consortia with mannitol/lyoprotectant solution (OPS Diagnostics Lebanon, NJ, USA) as per manufacturer's recommendation and the microbial suspension was aliquoted into lyophilization vials (OPS Diagnostics, Lebanon, NJ, USA). After 60 minutes at −80° C., the mixtures were placed in the FreeZone 6 freeze dry system (Labconco, Kansas City, MO), vacuum was applied, and the water in the samples was allowed to sublimate. Samples were stored at 4° C. until needed. In some experiments, the lyoprotectant solution was prepared by adding the following chemicals to microbial cultures for a final concentration of 0.75 g/L Tryptic Soy Broth (Becton, Dickinson and Company, USA), 10 g/L sucrose (Sigma Aldrich, USA) and 5 g/L skim milk (Carnation, Nestlé S.A, CH).

Co-formulation of microbes with agro-carriers: Liquid microbial consortia (produced from co-culture or individually grown and then pooled) or individual bacteria strains produced as described above, were impregnated onto agro-carriers such as perlite, Azomite® (Azomite, UT, USA), pumice, Monobasic Ammonium phosphate fertilizer (MAP; Mosaic, MN, USA), Muriate of potash fertilizer (MOP; Mosaic, MN, USA), and Biochar (Cool Terra®; Cool Planet Energy system, CO, USA). Depending on the carrier's water retention characteristics, different volumes of microbial consortia were used so as to saturate the carrier from as low as 35 µL for per gram up to 6 mL per gram. The microbe/agro-carrier mixture was then dried overnight at 30° C.-35° C. before storing in air tight containers for further shelf life microbial survivability studies and plant assays.

In the case of co-formulation with liquid agro-chemicals such as urea and ammonium nitrate in water ($UAN_{32}$; TGI, CA, USA) or fertilizer dust control agents (DUSTROL; ArrMaz FL, USA), liquid microbial consortia, produced as detailed above, were mixed at various ratios (described in examples below) prior to storage and microbial survivability analysis. All work was performed under sanitary conditions to minimize contamination.

In some instances, freeze-dried bacterial consortia were used, in order to minimize the effects of the culture broth on the carrier's chemistry. Details are described in examples as appropriate.

Analysis of Bacteria Genomes for DPA Synthase Production

Microbial genomic DNA extraction: Bacterial cells of different species were grown and harvested from optimized liquid broth and culture conditions. PowerSoil DNA isolation kit (MO BIO Laboratories, Inc, Carlsbad, CA USA) was used for small scale genomic DNA extractions. For large scale genomic DNA extractions, the GenElute Bacterial Genomic DNA kit (Sigma-Aldrich, St. Louis, MO USA) or Qiagen Genomic DNA Buffer Set and Genomic-tip 500/G (Qiagen, Hilden, Germany) were used following the methods recommended by the manufacturer. The resulting genomic DNA was subsequently precipitated with equal volume of isopropanol, washed with 70% ethanol, air-dried, and resuspended in TE buffer.

Whole genome sequencing (WGS): Whole Genome Sequencing of biologically pure isolates was performed using PacBio RSII system (Pacific Biosciences, Menlo Park, CA USA) following the manufacturer's recommended method for sequence library preparation and sequencing. An average of 73,000 reads of 24 kb in length on average were generated from the microbial isolates, followed by de novo genome assembly with Hierarchical Genome Assembly Process (HGAP, Pacific Biosciences, Menlo Park, CA USA).

Identification of DPA synthase coding sequence in selected bacteria strains: Initial bioinformatic analyses included select members of the class Bacilli; Bacillus (Bacillus megaterium, Bacillus subtilis, Bacillus licheniformis, Bacillus amyloliquefaciens, Bacillus sp., and Bacillus flexus), as well as Lactobacillus (Lactobacillus delbrueckii). First, using previously acquired whole-genome sequences, a bacterial pan-genome analysis was performed using BPGA-Version-1.3 (iicb.res.in/bpga/index.html) to estimate the genomic diversity and to determine the core (conserved), accessory (dispensable), and unique (strain-specific) gene pool. A search was then performed for any dipicolinate synthase subunit A (DpaA) in the accessory gene set. This was followed by a complete search of the strains in Table 1 for DpaA and DpaB using a custom Bash script (Free Software Foundation, 2007).

Briefly, protein coding genes were annotated in two stages. Prodigal (PROkaryotic DYnamic programming Gene-finding ALgorithm (Hyatt et al., BMC Bioinformatics 11:119, 2010)) was used to identify the coordinates of candidate genes but does not describe the putative gene product. These candidate genes were then compared to large databases in a hierarchical manner, starting with a smaller trustworthy database, moving to medium-sized but domain-specific databases, and finally to curated models of protein families. By default, an e-value threshold of $10^{-6}$ was used with the following series of databases:

1. All bacterial proteins in UniProt that have real protein or transcript evidence and are not a fragment. BLAST+ is used for the search.
2. All proteins from finished bacterial genomes in RefSeq for a specified genus. BLAST+ is used for the search.
3. A series of hidden Markov model profile databases, including Pfam (Punta et al., 2012) and TIGRFAMs (Haft et al., 2013). This is performed using hmmscan from the HMMER 3.1 package (Eddy, 2011).
4. If no matches can be found, label as 'hypothetical protein'.

These data were then tabulated along with the capacity for sporulation and dry-formulation survivability (see Table 6) to establish correlations between DPA synthase and viability. Alignments of DpaA and DpaB genes were then performed using Clustal Omega (www.ebi.ac.uk/Tools/msa/clustalo/) and amino acid composition and frequency statistics calculated using Seaview 4 (Gouy et al. *Mol. Biol. Evol.* 27:221-224, 2010). DpaA and DpaB amino acid alignments were then used to calculate consensus sequences and probability matrices in R using packages Biostrings and seqinr (Pagès et al., 2016; Charif and Lobry, *Structural Approaches to Sequence Evolution*, pp. 207-232, 2007; R Core Team, 2016).

Dry formulation sample preparation: For each shelf-life timepoint, 0.03-1 g of dry formulation (agro-carrier/bacterial consortium) was suspended in up to 3 mL of culture broth such as peptone water or other appropriate medium and incubated up to 1 hr at room temperature. In some instances, gentle sonication (35 khz) was used to release bacteria from dry matrices using a water bath sonicator (VWR ultrasonic cleaner). The suspension was subsequently serially diluted from $10^{-1}$ to $10^{-5}$ in sterile peptone water or other type of culture broth. In other cases, dry material was added directly to liquid media for growth.

Survivability assay: The bacterial strains which underwent treatment(s) were given the opportunity to multiply. In order to maximize the growth potential of each strain in the consortium, several different agar media were used such as chA (semi-dry chitin, 5 g/L; $K_2HPO_4$, 0.7 g/L; $KH_2PO_4$, 0.3 g/L; $MgSO_4.5H_2O$, 0.5 g/L; $FeSO_4.7H_2O$, 0.01 g/L; $ZnSO_4$, 0.001 g/L; $MnCl_2$, 0.001 g/L and agar, 15 g/L), RCM, NA, MP, YPD, RhX, AMAS, and/or BHIS. In some instances, each serial dilution produced above was spread plated onto one or more agar media in duplicate. In other cases, dry material produced above was suspended into one or more liquid media in sextuplet. For plate cultures, plates were incubated in static incubators, one set aerobically at 30° C. and the other set anaerobically at 35° C. for 3 days. For liquid cultures, tubes were incubated either shaking aerobically at 30° C. or static anaerobically at 35° C. for 7 days. Bacteria which had survived the treatment(s) grew either by

TABLE 6

Summary of strains capable of sporulating and producing DPA

| Bacteria strains | Sporulation ability | Presence of DPA synthase genes | DPA production |
|---|---|---|---|
| A. pasteurianus | N | NF | ND |
| A. vinelandii | Y | NF | ND |
| B. amyloliquefaciens | Y | Y | Y |
| B. flexus | Y | Y | Y |
| B. licheniformis | Y | Y | Y |
| B. megaterium | Y | Y | Y |
| B. subtilis | Y | Y | Y |
| Bacillus sp. | Y | Y | Y |
| C. beijerinckii | Y | NF | Y |
| C. pasteurianum | Y | NF | ND |
| L. buchneri | N | NF | ND |
| L. casei/paracasei | N | NF | ND |
| L. delbrueckii | N | NF | ND |
| L. vini | N | NF | ND |
| O. oncorhynchi | Y | Y | ND |
| P. chibensis | Y | Y | Y |
| P. cookii | Y | Y | Y |
| P. lautus | Y | Y | Y |
| P. putida | N | NF | ND |
| Pseudomonas sp. | N | NF | ND |
| S. griseus | Y | NF | ND |
| V. halophilus | Y | Y | ND |
| S. venezuelae | Y | NF | ND |
| S. pratensis | Y | NF | ND |
| P. azoreducens | Y | Y | Y |
| B. firmus | Y | Y | Y |

Y: yes;
N: no;
NF: not found;
ND: not detected

Bacteria in Consortia Survivability Assay

Liquid co-formulation sample preparation: For each shelf-life timepoint, 1 mL of the co-formulation (agrochemical/bacterial consortium) was serially diluted from $10^{-1}$ to $10^{-5}$ in sterile peptone water.

forming colonies or multiplied in liquid cultures, and this growth was then be sampled and identified using droplet digital PCR (ddPCR).

Genomic DNA was extracted from harvested cells using the DNeasy PowerLyzer PowerSoil kit (Qiagen, Inc., Germantown, MD USA) per the manufacturer's recommendations. DNA was then quantified using the Quantas Fluorometer and the QuantiFluor dsDNA (Promega Corporation, Madison, WI USA) and processed for identification and quantification using strain specific probes in conjunction with ddPCR (Dreo et al., *Anal. Bioanal. Chem.* 406:6513-6528, 2014; Yin, et al., *Journal of Microbiological Methods* 65:21-31, 2006). Briefly, ddPCR reactions were prepared by combining DNA sample, primers, and probes (designed using unique sequences from the 16S genes and/or unique coding gene sequences identified from WGS genome assemblies as previously described in WO 2018/045004, incorporated herein by reference) with Bio-Rad's ddPCR Supermix for Probes per the manufacturer's recommendations. Droplets were then generated using either the QX200™ droplet generator or the AutoDG™ Instrument per the manufacturer's recommendations. Polymerase chain reaction (PCR) was carried out using the Eppendorf Mastercycler® nexus gradient using the recommended thermal cycling conditions from Bio-Rad's ddPCR Supermix for Probes. Following the PCR protocol, reactions were read using the QX200 droplet reader. Finally, concentrations were analyzed with QuantaSoft™ software.

In the case of single strain survivability identification after co-formulation with liquid or dry agro-carrier, simple plating was performed using agar medium best suited of the given strains, as described in Table 2.

Example 2

Identification of DPA Synthase Coding Sequence in Selected Bacterial Strains

Dipicolinate synthase subunit A (DpaA): An amino acid alignment of DpaA from the bacterial strains revealed that it is divergent, with only 28.4% of amino acids conserved. Results are summarized in Tables 7-9 and FIG. 1. *Oceanobacillus oncorhynchi* appeared more divergent than most other strains. By calculating the percent identity with the denominator defined as aligned positions, *O. oncorhynchi* had a 58% percent identity with the consensus sequence using BLOSUM62. In addition, these amino acid changes appeared to lie in conserved regions for most of the strains analyzed. The amino acid alignment of DpaA also revealed that *Virgibacillus halophilus* had two copies of the gene, likely due to a duplication of the gene. The first copy was highly divergent (51% identity with the consensus sequence, same method as above), and the second copy appeared to have been truncated by 29 amino acids, in addition to significant amino acid changes. In addition, while all other instances of DpaA were located sequentially with DpaB as part of an operon, in *V. halophilus* the two genes are separated by 539 other genes.

TABLE 7

Number of DpaA gene copies

| Strains with DPA genes | Number of DpaA gene copies |
|---|---|
| Bacillus megaterium | 1 |
| Bacillus subtilis | 1 |
| Paenibacillus cookii | 1 |
| Bacillus licheniformis | 1 |
| Paenibacillus lautus | 1 |
| Oceanobacillus oncorhynchi | 1 |
| Bacillus amyloliquefaciens | 1 |
| Bacillus sp. | 1 |
| Paenibacillus chibensis | 1 |
| Bacillus flexus | 1 |

TABLE 7-continued

Number of DpaA gene copies

| Strains with DPA genes | Number of DpaA gene copies |
|---|---|
| Bacillus firmus | 1 |
| Virgibacillus halophilus | 2 |
| Paenibacillus azoreducens | 1 |

TABLE 8

Sequence diversity of DpaA genes

| | | |
|---|---|---|
| Selected sites: | 303 | 100.0% |
| Complete (no gaps, no X): | 262 | 86.5% |
| Variable: | 208 | 68.6% |
| Informative: | 176 | 58.1% |
| Gaps or X: | 41 | 13.5% |
| Identical: | 54 | 17.8% |
| Conserved, not identical: | 32 | 10.6% |
| Total conserved: | 86 | 28.4% |

TABLE 9

Amino acid composition of DpaA genes
Amino Acid Composition (all sites)

| | |
|---|---|
| Group 1: | 30.50% |
| E: | 5.7 |
| D: | 6 |
| Q: | 3.4 |
| N: | 3.1 |
| H: | 2.3 |
| R: | 4.3 |
| K: | 5.6 |
| Group 2: | 29.90% |
| I: | 9.3 |
| L: | 10.2 |
| M: | 2.8 |
| V: | 7.6 |
| Group 3: | 33.50% |
| A: | 9 |
| P: | 3.7 |
| S: | 5.8 |
| G: | 8.3 |
| T: | 6.7 |
| Group 4: | 4.90% |
| F: | 3.2 |
| Y: | 1.6 |
| Group 5: | 1.30% |
| W: | 0.1 |
| C: | 1.2 |

Dipicolinate synthase subunit B (DpaB): An amino acid alignment of DpaB from the bacterial strains revealed that it is more conserved that DpaA, with 45.5% of the amino acids conserved. Results are summarized in Tables 10-12 and FIG. 2. No duplications or major truncations were detected. As mentioned above, all copies of DpaB were located sequentially with DpaA as part of an operon, except for *V. halophilus* whose DpaB lies 539 genes upstream from DpaA.

TABLE 10

Number of DpaB gene copies

| Strains with DPA genes | Number of DpaB gene copies |
|---|---|
| Bacillus megaterium | 1 |
| Bacillus subtilis | 1 |
| Paenibacillus cookii | 1 |
| Bacillus licheniformis | 1 |
| Paenibacillus lautus | 1 |

TABLE 10-continued

Number of DpaB gene copies

| Strains with DPA genes | Number of DpaB gene copies |
|---|---|
| Oceanobacillus oncorhynchi | 1 |
| Bacillus amyloliquefaciens | 1 |
| Bacillus sp. | 1 |
| Paenibacillus chibensis | 1 |
| Bacillus flexus | 1 |
| Bacillus firmus | 1 |
| Virgibacillus halophilus | 1 |
| Paenibacillus azoreducens | 1 |

TABLE 11

DpaB sequence diversity

| Selected sites: | 202 | 100.0% |
|---|---|---|
| Complete (no gaps, no X): | 196 | 97.0% |
| Variable: | 133 | 65.8% |
| Informative: | 104 | 51.5% |
| Gaps or X: | 6 | 3.0% |
| Identical: | 63 | 31.2% |
| Conserved, not identical: | 29 | 14.4% |
| Total conserved: | 92 | 45.5% |

TABLE 12

Amino acid composition of DpaB genes
Amino Acid Composition (all sites)

| Group 1: | 30.30% |
|---|---|
| E: | 4.8 |
| D: | 4.7 |
| Q: | 3.8 |
| N: | 6.2 |
| H: | 1.4 |
| R: | 3.2 |
| K: | 6.3 |
| Group 2: | 29.00% |
| I: | 6.5 |
| L: | 9.8 |
| M: | 4.3 |
| V: | 8.4 |
| Group 3: | 34.30% |
| A: | 8.3 |
| P: | 6.6 |
| S: | 5.2 |
| G: | 7 |
| T: | 7.1 |
| Group 4: | 4.70% |
| F: | 3 |
| Y: | 1.7 |
| Group 5: | 1.70% |
| W: | 0.6 |
| C: | 1.1 |

Correlation between production of DPA (in assays described above) and presence of DPA genes: As noted in Table 6, *Clostridium beijerinckii* was detected as a DPA-producing strain via the Terbium-DPA fluorescence assay, but neither DpaA or DpaB were identifiable in its genome. We found that *C. beijerinckii* possesses an iron-sulfur flavoprotein (Isf) that is structurally related to EtfA, which has been previously implicated in DPA production (Orsburn et al., Mol. Microbiol. 75:178-186, 2010). Six copies of the iron-sulfur flavoprotein were detected in the genome of *C. beijerinckii*. These sequences were then aligned with isf sequences from four diverse bacteria: *Archaeoglobus fulgidus*, *Methanocaldococcus jannaschii*, *Methanosarcina thermophila*, and *Peptoclostridium difficile* (FIG. 3). This Isf protein is absent in *Clostridium pasteurianum*, and production of DPA was not detected in *C. pasteurianum*. Additional support for the role of Isf in DPA production is provided in Example 12.

Example 3

Survival of Selected Single Strains on a Carrier

An evaluation of bacterial survivability in Azomite® impregnated with individual strains was performed. Four strains were selected based on their ability to produce DPA in lab assays and/or on the results of DPA gene identification. The impregnated material was stored dry for 5 days before evaluating bacteria survivability. Results are as indicated in Table 13. 100% of strains with detectable production of DPA (2/2) remained viable for 5 days. For strains with undetectable DPA production, 50% (1/2 strains) remained viable for 5 days.

TABLE 13

Survival of individual bacteria in co-formulation with
dry Azomite ® vs. DPA production

| Microbe | DPA production | 5-day viability |
|---|---|---|
| Streptomyces venezuelae | 0 | 1 |
| Streptomyces pratensis | 0 | 0 |
| Bacillus firmus | 1 | 1 |
| Paenibacillus azoreducens | 1 | 1 |

1 = detected and 0 = not detected or below detection limit. The DPA production column represents those strains that tested positive for DPA production via the Terbium-DPA fluorescence assay.

In a second experiment, the number of strains was expanded. An evaluation of bacteria survivability in Azomite® following impregnation was performed over a 1-month period. Briefly, Azomite® was impregnated with individual isogenic strains, dried, and samples were taken on days 3, 7, 14, 21, and 28 for bacteria viability analysis. Results are as indicated in Table 14 and show that 100% (4/4) bacteria with identified DPA genes and producing DPA remained viable for 1 month. For strains with no identified DPA genes and undetectable DPA production, 40% (2/5 strains) remained viable for 1 month.

TABLE 14

Survival of individual bacteria in co-formulation with dry Azomite ® vs.
DPA gene identification and DPA production

| Microbe | DPA Genes | DPA production | 3 days | 7 days | 14 days | 21 days | 28 days |
|---|---|---|---|---|---|---|---|
| Bacillus subtilis | 1 | 1 | 1 | 1 | 1 | 1 | 1 |
| Paenibacillus putida | 0 | 0 | 1 | 0 | 0 | 0 | 0 |
| Pseudomonas sp. | 0 | 0 | 1 | 1 | 1 | 1 | 1 |
| Streptomyces griseus | 0 | 0 | 1 | 1 | 1 | 1 | 1 |

TABLE 14-continued

Survival of individual bacteria in co-formulation with dry Azomite ® vs. DPA gene identification and DPA production

| Microbe | DPA Genes | DPA production | 3 days | 7 days | 14 days | 21 days | 28 days |
|---|---|---|---|---|---|---|---|
| Streptomyces venezuelae | 0 | 0 | 1 | 0 | 0 | 0 | 0 |
| Streptomyces pratensis | 0 | 0 | 0 | 0 | 0 | 0 | 0 |
| Bacillus firmus | 1 | 1 | 1 | 1 | 1 | 1 | 1 |
| Paenibacillus azoreducens | 1 | 1 | 1 | 1 | 1 | 1 | 1 |

1 = detected and 0 = not detected or below detection limit. The DPA genes column represents those strains that possess both DpaA and DpaB genes. The DPA production column represents those strains that tested positive for DPA production via the Terbium-DPA fluorescence assay.

A second agro-carrier (perlite) was then tested. A microbial survivability evaluation was performed over a 1-month period, as previously was described with Azomite®. The results are as indicated in Table 15 and show that 100% (4/4) of bacteria with identified DPA genes and producing DPA remained viable for 1 month. For strains with no detected DPA genes and undetectable DPA production, 60% (3/5 strains) remained viable for 1 month.

TABLE 15

Survival of individual bacteria in co-formulation with dry perlite vs. DPA gene identification and DPA production

| Microbe | DPA Genes | DPA production | 3 days | 7 days | 14 days | 21 days | 28 days |
|---|---|---|---|---|---|---|---|
| Bacillus subtilis | 1 | 1 | 1 | 1 | 1 | 1 | 1 |
| Paenibacillus putida | 0 | 0 | 1 | 1 | 1 | 1 | 0 |
| Pseudomonas sp. | 0 | 0 | 1 | 1 | 1 | 1 | 0 |
| Streptomyces griseus | 0 | 0 | 1 | 1 | 1 | 1 | 0 |
| Streptomyces venezuelae | 0 | 0 | 0 | 0 | 0 | 0 | 0 |
| Streptomyces pratensis | 0 | 0 | 0 | 0 | 0 | 0 | 0 |
| Bacillus firmus | 1 | 1 | 1 | 1 | 1 | 1 | 1 |
| Paenibacillus azoreducens | 1 | 1 | 1 | 1 | 1 | 1 | 1 |

1 = detected and 0 = not detected or below detection limit. The DPA genes column represents those strains that possess both DpaA and DpaB genes. The DPA production column represents those strains that tested positive for DPA production via the Terbium-DPA fluorescence assay.

Example 4

Survival of Microbial Consortia on a Carrier

In the following experiment, 22 bacteria were grown individually and subsequently mixed to produce a consortium, as described above. Dry Azomite® in a pelletized form was impregnated with 0.23-0.4 mL of consortium (to preserve the integrity of the pellet), dried and stored for two weeks before analyzing which bacteria survived using the assay for assaying microbial viability from a consortium (Example 1). Two independent trials were conducted, and the results are summarized in Table 16. We observed that 83% and 92% of bacteria strains with identified DPA genes and/or producing DPA remained viable 2 weeks after impregnation on Azomite®. The strain which did not appear to show consistent viability in the two trials was O. oncorhynchi. As mentioned above, O. oncorhynchi DPA synthase subunit A appears more divergent than most other examined strains, with a 58% percent identity with the consensus sequence using BLOSUM62. For strains with no identified DPA genes and no detectable DPA production, the results varied between 60% and 70% of bacteria remaining viable within the same period. Reproducibility between the two trials was low and may be attributed to different metabolic states of this set of microbes at the time of impregnation.

TABLE 16

Survival of individual bacteria in co-formulation with dry Azomite ®

| Bacteria genus/species | DPA Genes | DPA production | Trial 1 2 weeks | Trial 2 2 weeks | |
|---|---|---|---|---|---|
| *Bacillus amyloliquefaciens* | 1 | 1 | 1 | 1 | Bacteria with identified DPA genes and/or producing DPA |
| *Bacillus flexus* | 1 | 1 | 1 | 1 | |
| *Bacillus licheniformis* | 1 | 1 | 1 | 1 | |
| *Bacillus megaterium* | 1 | 1 | 1 | 1 | |
| *Bacillus* sp. | 1 | 1 | 1 | 1 | |
| *Bacillus subtilis* | 1 | 1 | 1 | 1 | |
| *Paenibacillus chibensis* | 1 | 1 | 1 | 1 | |

TABLE 16-continued Survival of individual bacteria in co-formulation with dry Azomite ®

| Bacteria genus/species | DPA Genes | DPA production | Trial 1 2 weeks | Trial 2 2 weeks | |
|---|---|---|---|---|---|
| *Paenibacillus cookii* | 1 | 1 | 1 | 1 | |
| *Oceanobacillus oncorhynchi* | 1 | 0 | 1 | 0 | |
| *Paenibacillus lautus* | 1 | 0 | 1 | 1 | |
| *Virgibacillus halophilus* | 1 | 0 | 0 | 0 | |
| *Clostridium beijerinckii* | 0 | 1 | 1 | 1 | |
| *Acetobacter pasteurianus* | 0 | 0 | 0 | 1 | Bacteria with |
| *Azotobacter vinelandii* | 0 | 0 | 1 | 1 | no identified |
| *Clostridium pasteurianum* | 0 | 0 | 1 | 1 | DPA genes |
| *Lactobacillus buchneri* | 0 | 0 | 1 | 1 | and no |
| *Lactobacillus delbrueckii* | 0 | 0 | 0 | 0 | detectable |
| *Lactobacillus paracasei/casei* | 0 | 0 | 1 | 0 | DPA production |
| *Lactobacillus vini* | 0 | 0 | 0 | 0 | |
| *Pseudomonas putida* | 0 | 0 | 1 | 0 | |
| *Pseudomonas* sp. | 0 | 0 | 1 | 1 | |
| *Streptomyces griseus* | 0 | 0 | 1 | 1 | |

1 = detected and 0 = not detected or below detection limit. The DPA genes column represents those strains that possess both DpaA and DpaB genes. The DPA production column represents those strains that test positive for DPA production via the Terbium-DPA fluorescence assay.

Similar to the experiment with Azomite® described above, the 22 bacteria were grown individually and subsequently mixed to produce a consortium. Perlite was impregnated with 2-6 mL of consortium, dried and stored for 2 weeks before analyzing which bacteria survived using the assay for assaying microbial viability from a consortium, (Example 1). Two independent trials were conducted, and the results are summarized in Table 17. We observed that 58% and 100% of bacteria strains with identified DPA genes and/or producing DPA remain viable two weeks after impregnation on perlite. For strains with no identified DPA genes and no detectable DPA production, the results varied between 60% and 80% of bacteria remaining viable within the same period. Compared with the Azomite® experiment, the bacteria with identified DPA genes and/or producing DPA showed good reproducibility even using a different impregnation substrate. They also outperformed those with no identified DPA genes or with no detectable DPA production in our assay.

TABLE 17

Survival of individual bacteria from consortium in co-formulation with perlite

| Bacteria genus/species | DPA Genes | DPA production | Trial 1 2 weeks | Trial 2 2 weeks | |
|---|---|---|---|---|---|
| *Bacillus amyloliquefaciens* | 1 | 1 | 1 | 1 | Bacteria with identified DPA genes and/or producing DPA |
| *Bacillus flexus* | 1 | 1 | 0 | 1 | |
| *Bacillus licheniformis* | 1 | 1 | 1 | 1 | |
| *Bacillus megaterium* | 1 | 1 | 1 | 1 | |
| *Bacillus* sp. | 1 | 1 | 1 | 1 | |
| *Bacillus subtilis* | 1 | 1 | 1 | 1 | |
| *Paenibacillus chibensis* | 1 | 1 | 1 | 1 | |
| *Paenibacillus cookii* | 1 | 1 | 1 | 1 | |
| *Oceanobacillus oncorhynchi* | 1 | 0 | 0 | 1 | |
| *Paenibacillus lautus* | 1 | 0 | 1 | 1 | |
| *Virgibacillus halophilus* | 1 | 0 | 0 | 1 | |
| *Clostridium beijerinckii* | 0 | 1 | 1 | 1 | |
| *Acetobacter pasteurianus* | 0 | 0 | 1 | 0 | Bacteria with no identified DPA genes and no detectable DPA production |
| *Azotobacter vinelandii* | 0 | 0 | 0 | 0 | |
| *Clostridium pasteurianum* | 0 | 0 | 1 | 1 | |
| *Lactobacillus buchneri* | 0 | 0 | 1 | 1 | |
| *Lactobacillus delbrueckii* | 0 | 0 | 0 | 0 | |
| *Lactobacillus paracasei/casei* | 0 | 0 | 1 | 1 | |
| *Lactobacillus vini* | 0 | 0 | 1 | 0 | |
| *Pseudomonas putida* | 0 | 0 | 1 | 1 | |
| *Pseudomonas* sp. | 0 | 0 | 1 | 1 | |
| *Streptomyces griseus* | 0 | 0 | 1 | 1 | |

1 = detected and 0 = not detected or below detection limit. The DPA genes column represents those strains that possess both DpaA and DpaB genes. The DPA production column represents those strains that test positive for DPA production via the Terbium-DPA fluorescence assay.

Example 4

Survival of Microbial Consortia Co-Formulated with Liquid Dust Control Agents

In the experiments below, bacterial strains of interest were grown on semi-solid agar plates using media as described above (see Table 2). Dust control chemical/bacteria co-formulations were generated by suspending a 1 μL loopful scraped from an agar plate in 200 μL of sterile peptone water, and then mixing with dust control chemicals at a rate of 5% v/v. Survivability of each strain in co-formulation was then determined by inoculating fresh media (Table 3) with the bacteria/agrochemical mixture and scoring for signs of growth.

Survivability of bacteria co-formulated with MDC-200: An evaluation of bacterial viability following co-formulation with the dust control agent MDC-200 (ArrMaz, FL, USA) was performed over a 1-month period. Results are as indicated in Table 18. We observed that 92% (11/12) of bacteria with identified DPA genes and/or producing DPA remained viable for 1 month. For strains with no identified DPA genes and undetectable DPA production, 0% (0/10 strains) remained viable for 1 month.

Survivability of bacteria co-formulated with DUSTROL® 3275: An evaluation of bacterial viability following co-formulation with DUSTROL® 3275 (ArrMaz, FL, USA) was performed over a 1-month period. Results are as indicated in Table 18. We observed that 100% (12/12) of bacteria with identified DPA genes and/or producing DPA remained viable for 1 month. For strains with no identified DPA genes and undetectable DPA production, 0% (0/10 strains) remained viable for 1 month.

Survivability of bacteria co-formulated with DUSTROL® 3133: An evaluation of bacterial viability following co-formulation with DUSTROL® 3133 (ArrMaz, FL, USA) was performed over a 1-month period. Results are as indicated in Table 18. We observed that 100% (12/12) of bacteria with identified DPA genes and/or producing DPA remained viable for 1 month. For strains with no identified DPA genes and undetectable DPA production, 0% (0/10 strains) remained viable for 1 month.

Survivability of bacteria co-formulated with DUSTROL® 3139: An evaluation of bacterial viability following co-formulation with DUSTROL® 3139 (ArrMaz, FL, USA) was performed over a 1-month period. Results are as indicated in Table 18. We observed that 92% (11/12) of bacteria with identified DPA genes and/or producing DPA remained viable for 1 month. For strains with no identified DPA genes and undetectable DPA production, 0% (0/10 strains) remained viable for 1 month.

Survivability of bacteria co-formulated with DUSTROL® 3001: An evaluation of bacterial viability following co-formulation with DUSTROL® 3001 (ArrMaz, FL, USA) was performed over a 1-month period. Results are as indicated in Table 18. We observed that 33% (4/12) of bacteria with identified DPA genes and/or producing DPA remained viable for 1 month. Strains with no identified DPA genes and undetectable DPA production, 0% (0/10 strains) remained viable for 1 month. The reduced survival in this experiment may be due to incompatibility of microbes (whether or not they produce DPA) with one or more components of DUSTROL® 3001.

Survivability of bacteria co-formulated with DUSTROL® 3010: An evaluation of bacterial viability following co-formulation with DUSTROL® 3010 (ArrMaz, FL, USA) was performed over a 1-month period. Results are as indicated in Table 18. We observed that 75% (9/12) of bacteria with identified DPA genes and/or producing DPA remained viable for 1 month. For strains with no identified DPA genes and undetectable DPA production, 20% (2/10 strains) remained viable for 1 month.

TABLE 18

One-month survival of individual bacteria from consortium in co-formulation with liquid dust control chemicals

| Bacteria Genus/Species | DPA genes | DPA production | MDC-200 | DUSTROL ® 3275 | DUSTROL ® 3133 | DUSTROL ® 3139 | DUSTROL ® 3001 | DUSTROL ® 3010 | |
|---|---|---|---|---|---|---|---|---|---|
| *Bacillus amyloliquefaciens* | 1 | 1 | 1 | 1 | 1 | 1 | 1 | 1 | Bacteria with identified DPA genes and/or DPA production |
| *Bacillus flexus* | 1 | 1 | 1 | 1 | 1 | 1 | 0 | 1 | |
| *Bacillus licheniformis* | 1 | 1 | 1 | 1 | 1 | 1 | 0 | 1 | |
| *Bacillus megaterium* | 1 | 1 | 1 | 1 | 1 | 1 | 0 | 1 | |
| *Bacillus* sp. | 1 | 1 | 1 | 1 | 1 | 1 | 0 | 1 | |
| *Bacillus subtilis* | 1 | 1 | 1 | 1 | 1 | 1 | 1 | 1 | |
| *Paenibacillus chibensis* | 1 | 1 | 1 | 1 | 1 | 1 | 1 | 1 | |
| *Paenibacillus cookii* | 1 | 1 | 1 | 1 | 1 | 1 | 0 | 0 | |
| *Oceanobacillus oncorhynchi* | 1 | 0 | 1 | 1 | 1 | 1 | 0 | 1 | |
| *Paenibacillus lautus* | 1 | 0 | 1 | 1 | 1 | 1 | 1 | 0 | |
| *Virgibacillus halophilus* | 1 | 0 | 0 | 1 | 1 | 0 | 0 | 0 | |
| *Clostridium beijerinckii* | 0 | 1 | 1 | 1 | 1 | 1 | 0 | 1 | |
| *Acetobacter pasteurianus* | 0 | 0 | 0 | 0 | 0 | 0 | 0 | 1 | Bacteria with no identified DPA genes and no detectable DPA production |
| *Azotobacter vinelandii* | 0 | 0 | 0 | 0 | 0 | 0 | 0 | 0 | |
| *Clostridium pasteurianum* | 0 | 0 | 0 | 0 | 0 | 0 | 0 | 0 | |
| *Lactobacillus buchneri* | 0 | 0 | 0 | 0 | 0 | 0 | 0 | 0 | |
| *Lactobacillus delbrueckii* | 0 | 0 | 0 | 0 | 0 | 0 | 0 | 0 | |
| *Lactobacillus casei* | 0 | 0 | 0 | 0 | 0 | 0 | 0 | 0 | |

TABLE 18-continued

One-month survival of individual bacteria from consortium in co-formulation with liquid dust control chemicals

| Bacteria Genus/Species | DPA genes | DPA production | MDC-200 | DUSTROL® 3275 | DUSTROL® 3133 | DUSTROL® 3139 | DUSTROL® 3001 | DUSTROL® 3010 |
|---|---|---|---|

TABLE 19-continued

Bacterial survivability over a one-month period in co-formulation with UAN fertilizer

| Genus/Species | DPA genes | DPA production | UAN - 0 Day | UAN - 7 Day | UAN - 14 Day | UAN - 30 Day |
|---|---|---|---|---|---|---|
| Pseudomonas putida | 0 | 0 | 0 | 0 | 0 | 0 |
| Pseudomonas sp. | 0 | 0 | 0 | 0 | 0 | 0 |
| Streptomyces griseus | 0 | 0 | 1 | 0 | 0 | 0 |

1 = detected and 0 = not detected or below detection limit. The DPA genes column represents those strains that possess both DpaA and DpaB genes. The DPA production column represents those strains that test positive for DPA production via the Terbium-DPA fluorescence assay. The next 4 columns represent timepoints where the co-formulation was tested for viability using the assay described above.
*On Day 30, *Acetobacter pasteurianus* (a strain unable to produce DPA) was detected as viable for the first time, indicating false negatives for the 0, 7, and 14-day timepoints.

Example 6

Survival of Microbial Consortia Co-Formulated with Biochar

In this experiment, the 22 bacteria shown in Table 4 were grown individually and subsequently mixed to produce a consortium, as described above. One gram of Biochar (Cool Terra®; Cool Planet Energy system, CO, USA) was impregnated with ~0.5 mL of consortium, dried, and stored for 7 days before analyzing which bacteria survived using the survivability assay previously described. The results are summarized in Table 20. 66.7% (7/12 strains) of the bacteria with identified DPA genes and/or producing DPA remained viable 7 days after impregnation on biochar. For strains with no identified DPA genes and no detectable DPA production, 30% (3/10 strains) remained viable within the same time frame.

Example 7

Survival of Microbial Consortia Co-Formulated with Dry Fertilizer Granules

In this experiment, the 22 bacteria shown in Table 4 were grown individually and subsequently mixed to produce a consortium and impregnated on MOP (0-0-60) dry fertilizer at a rate of 35 µL/g, as described above. The fertilizer was then stored at room temperature and periodically sampled to assess microbial survivability as previously described. The results are summarized in Table 21. 66.7% (8/12 strains) of the bacteria with identified DPA genes and/or producing DPA remained viable up to 7 days. For strains with no identified DPA genes and no detectable DPA production, 30% (3/10 strains) remained viable within the same time frame.

TABLE 20

Survival of bacteria from consortium in biochar after 7 days

| Bacteria genus/species | DPA Genes | DPA production | 7 days | |
|---|---|---|---|---|
| Bacillus amyloliquefaciens | 1 | 1 | 1 | Bacteria with identified DPA genes and/or producing DPA |
| Bacillus flexus | 1 | 1 | 1 | |
| Bacillus licheniformis | 1 | 1 | 1 | |
| Bacillus megaterium | 1 | 1 | 1 | |
| Bacillus sp. | 1 | 1 | 1 | |
| Bacillus subtilis | 1 | 1 | 1 | |
| Paenibacillus chibensis | 1 | 1 | 0 | |
| Paenibacillus cookii | 1 | 1 | 0 | |
| Oceanobacillus oncorhynchi | 1 | 0 | 0 | |
| Paenibacillus lautus | 1 | 0 | 1 | |
| Virgibacillus halophilus | 1 | 0 | 0 | |
| Clostridium beijerinckii | 0 | 1 | 1 | |
| Acetobacter pasteurianus | 0 | 0 | 0 | Bacteria with no identified DPA genes and no detectable DPA production |
| Azotobacter vinelandii | 0 | 0 | 0 | |
| Clostridium pasteurianum | 0 | 0 | 1 | |
| Lactobacillus buchneri | 0 | 0 | 1 | |
| Lactobacillus delbrueckii | 0 | 0 | 0 | |
| Lactobacillus paracasei/casei | 0 | 0 | 1 | |
| Lactobacillus vini | 0 | 0 | 0 | |
| Pseudomonas putida | 0 | 0 | 0 | |
| Pseudomonas sp. | 0 | 0 | 0 | |
| Streptomyces griseus | 0 | 0 | 0 | |

1 = detected and 0 = not detected or below detection limit. The DPA genes column represents those strains that possess both DpaA and DpaB genes. The DPA production column represents those strains that test positive for DPA production via the Terbium-DPA fluorescence assay.

TABLE 21

Survival of bacteria from consortium in MOP after 7 days

| Bacteria genus/species | DPA genes | DPA production | Survival on day 7 | |
|---|---|---|---|---|
| Bacillus amyloliquefaciens | 1 | 1 | 1 | Bacteria with |
| Bacillus flexus | 1 | 1 | 1 | identified |
| Bacillus licheniformis | 1 | 1 | 1 | DPA genes and/ |
| Bacillus megaterium | 1 | 1 | 1 | or producing DPA |
| Bacillus sp. | 1 | 1 | 0 | |
| Bacillus subtilis | 1 | 1 | 1 | |
| Paenibacillus chibensis | 1 | 1 | 0 | |
| Paenibacillus cookii | 1 | 1 | 1 | |
| Oceanobacillus oncorhynchi | 1 | 0 | 1 | |
| Paenibacillus lautus | 1 | 0 | 1 | |
| Virgibacillus halophilus | 1 | 0 | 0 | |
| Clostridium beijerinckii | 0 | 1 | 0 | |
| Acetobacter pasteurianus | 0 | 0 | 1 | Bacteria with |
| Azotobacter vinelandii | 0 | 0 | 0 | no identified |
| Clostridium pasteurianum | 0 | 0 | 1 | DPA genes and |
| Lactobacillus buchneri | 0 | 0 | 0 | no detectable |
| Lactobacillus delbrueckii | 0 | 0 | 0 | DPA production |
| Lactobacillus paracasei/casei | 0 | 0 | 0 | |
| Lactobacillus vini | 0 | 0 | 0 | |
| Pseudomonas putida | 0 | 0 | 0 | |
| Pseudomonas sp. | 0 | 0 | 1 | |
| Streptomyces griseus | 0 | 0 | 1 | |

1 = detected and 0 = not detected or below detection limit. The DPA genes column represents those strains that possess both DpaA and DpaB genes. The DPA production column represents those strains that test positive for DPA production via the Terbium-DPA fluorescence assay.

The 22 bacteria shown in Table 4 were also grown individually and subsequently mixed to produce a consortium and impregnated on MAP (11-52-0) at a rate of 35 µL/g, as described above. The fertilizer was then stored at room temperature and periodically sampled to assess microbial survivability as previously described. The results are summarized in Table 22. In this case, 58.3% (7/12 strains) of the bacteria with identified DPA genes and/or producing DPA remained viable up to 7 days. For strains with no identified DPA genes and no detectable DPA production, 40% (4/10 strains) remained viable within the same time frame.

TABLE 22

Survival of bacteria from consortium in MAP after 7 days

| Bacteria genus/species | DPA genes | DPA production | Survival on day 7 | |
|---|---|---|---|---|
| Bacillus amyloliquefaciens | 1 | 1 | 1 | Bacteria with |
| Bacillus flexus | 1 | 1 | 0 | identified DPA |
| Bacillus licheniformis | 1 | 1 | 1 | genes and/or |
| Bacillus megaterium | 1 | 1 | 1 | producing DPA |
| Bacillus sp. | 1 | 1 | 0 | |
| Bacillus subtilis | 1 | 1 | 0 | |
| Paenibacillus chibensis | 1 | 1 | 0 | |
| Paenibacillus cookii | 1 | 1 | 1 | |
| Oceanobacillus oncorhynchi | 1 | 0 | 1 | |
| Paenibacillus lautus | 1 | 0 | 1 | |
| Virgibacillus halophilus | 1 | 0 | 0 | |
| Clostridium beijerinckii | 0 | 1 | 1 | |
| Acetobacter pasteurianus | 0 | 0 | 1 | Bacteria with no |
| Azotobacter vinelandii | 0 | 0 | 0 | identified DPA |
| Clostridium pasteurianum | 0 | 0 | 1 | genes and no |
| Lactobacillus buchneri | 0 | 0 | 0 | detectable DPA |
| Lactobacillus delbrueckii | 0 | 0 | 0 | production |
| Lactobacillus paracasei/casei | 0 | 0 | 0 | |
| Lactobacillus vini | 0 | 0 | 0 | |
| Pseudomonas putida | 0 | 0 | 1 | |
| Pseudomonas sp. | 0 | 0 | 1 | |
| Streptomyces griseus | 0 | 0 | 0 | |

1 = detected and 0 = not detected or below detection limit. The DPA genes column represents those strains that possess both DpaA and DpaB genes. The DPA production column represents those strains that test positive for DPA production via the Terbium-DPA fluorescence assay.

Example 9

Survival of Microbes from Consortium Compared to DPA Expression/Production

In this experiment, the 22 bacteria shown in Table 4 were grown individually and subsequently mixed to produce a consortium, as described above. The consortium was then stored at room temperature and periodically sampled to assess microbial survivability, as previously described. The results are summarized in Table 23.

On week 2, 83% (10/12 strains) of the bacteria with identified DPA genes and/or producing DPA remained viable. For strains with no identified DPA genes and no detectable DPA production, 60% (6/10 strains) remained viable within the same time frame. After 7.5 weeks, that 58% (7/12 strains) of the bacteria with identified DPA genes and/or producing DPA remained viable. For strains with no identified DPA genes and no detectable DPA production, 50% (5/10 strains) remained viable within the period.

TABLE 23

Survival of bacteria from consortium in spent medium

| Bacteria genus/species | DPA genes | DPA production | 2 weeks | 7.5 weeks | |
|---|---|---|---|---|---|
| *Bacillus amyloliquefaciens* | 1 | 1 | 1 | 1 | Bacteria with identified DPA genes and/or producing DPA |
| *Bacillus flexus* | 1 | 1 | 1 | 0 | |
| *Bacillus licheniformis* | 1 | 1 | 1 | 1 | |
| *Bacillus megaterium* | 1 | 1 | 1 | 1 | |
| *Bacillus* sp. | 1 | 1 | 1 | 1 | |
| *Bacillus subtilis* | 1 | 1 | 1 | 1 | |
| *Paenibacillus chibensis* | 1 | 1 | 1 | 1 | |
| *Paenibacillus cookii* | 1 | 1 | 1 | 0 | |
| *Oceanobacillus oncorhynchi* | 1 | 0 | 0 | 0 | |
| *Paenibacillus lautus* | 1 | 0 | 1 | 0 | |
| *Virgibacillus halophilus* | 1 | 0 | 0 | 0 | |
| *Clostridium beijerinckii* | 0 | 1 | 1 | 1 | |
| *Acetobacter pasteurianus* | 0 | 0 | 1 | 1 | Bacteria with no identified DPA genes and no detectable DPA production |
| *Azotobacter vinelandii* | 0 | 0 | 0 | 0 | |
| *Clostridium pasteurianum* | 0 | 0 | 1 | 1 | |
| *Lactobacillus buchneri* | 0 | 0 | 1 | 1 | |
| *Lactobacillus delbrueckii* | 0 | 0 | 1 | 0 | |
| *Lactobacillus paracasei/casei* | 0 | 0 | 1 | 1 | |
| *Lactobacillus vini* | 0 | 0 | 1 | 1 | |
| *Pseudomonas putida* | 0 | 0 | 0 | 0 | |
| *Pseudomonas* sp. | 0 | 0 | 0 | 0 | |
| *Streptomyces griseus* | 0 | 0 | 0 | 0 | |

1 = detected and 0 = not detected or below detection limit. The DPA genes column represents those strains that possess both DpaA and DpaB genes. The DPA production column represents those strains that test positive for DPA production via the Terbium-DPA fluorescence assay.

Example 10

Summary of Microbial Survival

In all instances tested, spore forming bacteria with identified DPA genes and/or producing DPA outperformed strains with no identified DPA genes and no detectable DPA production in terms of survivability in co-formulation with agro-carriers over time, as either liquid or dry formulations (Table 24 and FIG. 4). Therefore in the rational design of microbial consortia with selected plant/soil beneficial traits for co-formulation with agro-carriers (wet and/or dry) or as seed treatments, the selection of spore forming and DPA-producing microbes can assist in providing that desired microbial functionalities (such as but not limited to nitrogen metabolism, sulfur metabolism, salt tolerance, mineral salt solubilization, cellulose degradation, chitin degradation, phytohormone production, iron metabolism, dephosphorylation of organic matter) are retained in the surviving microbes. In some instances, this can ensure sufficient redundancy in microbial functionalities present in the rationally designed consortium in order to comply with target crops, soils, and application practice needs as well as geographical and regulatory challenges.

TABLE 24

Survival of microbial strains in co-formulation with agro-chemicals/carriers

| Carrier (shelf-life tested) | Bacteria with identified DPA genes and/or producing DPA | Bacteria with no identified DPA genes and no detectable DPA production |
|---|---|---|
| MDC-200 (1 mo) | 92% | 0% |
| DUSTROL ® 3275 (1 mo) | 100% | 0% |
| DUSTROL ® 3133 (1 mo) | 100% | 0% |
| DUSTROL ® 3139 (1 mo) | 92% | 0% |
| DUSTROL ® 3001 (1 mo) | 33% | 0% |
| DUSTROL ® 3010 (1 mo) | 75% | 20% |
| UAN (1 mo) | 67% | 0% |
| Perlite (2 weeks) | 75-100% | 60-80% |
| Azomite ® (2 weeks) | 83.3% | 60% |
| Biochar (1 week) | 66.7% | 30% |
| MOP (1 week) | 66.7% | 30% |
| MAP (1 week) | 58.3% | 40% |
| Aged liquid/Spent medium (7.5 weeks) | 58% | 50% |

Example 11

Evaluation of Plant Growth Promoting Activity

Figure 5:
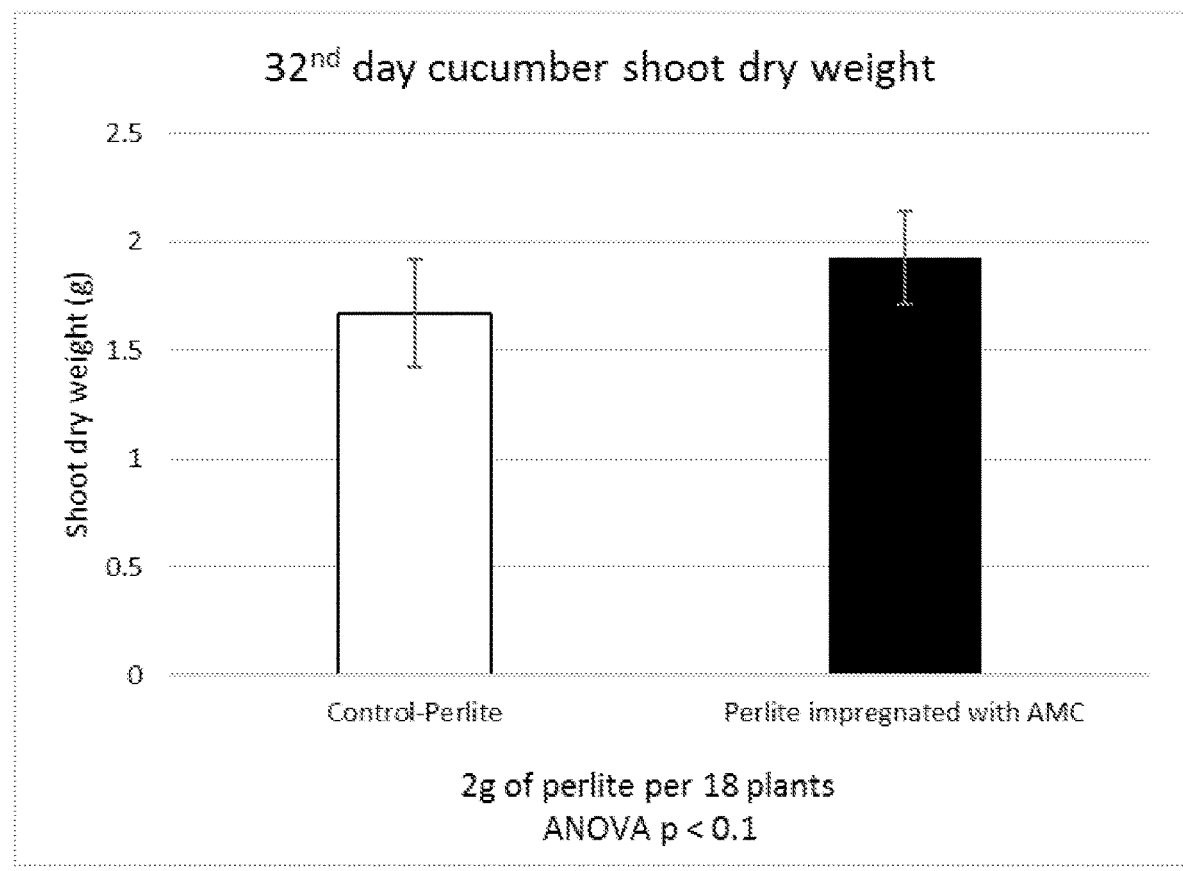
FIG. 5 is graph showing 32 day cucumber shoot dry weight in plants treated with perlite or perlite impregnated with a microbial consortium (AMC1).

Cucumber seeds purchased from The Seed Kingdom (Lubbock, TX) were pre-germinated for 4 days at 22-24° C. in rolled germination paper (Anchor Paper, Saint Paul, MN) impregnated with a dilute mixture of liquid fertilizer (25 ppm NPK in water). Potting medium (Sunshine Mix) was pre-treated with a Hoagland solution (Hoagland, Calif. Agric. Exp. Stn. Bull. 347:36-39, 1938), modified to contain P, 30.97 ppm; K, 39.1 ppm; Ca, 40.0 ppm; Mg, 14.59 ppm; S, 20.143 ppm; Fe, 1.010 ppm; Cu, 0.019 ppm; Co, 0.012 ppm; B, 2.44 ppm; Mn, 0.494 ppm; Mo, 0.001 ppm and Zn, 0.056 ppm. A rate of 1 L per pound of potting medium was used. To each pot, 1 mL of a 10% w/v urea solution was added before pre-germinated cucumber seedlings with similar length were transplanted. For each treatment (including control) 17-18 plants were randomized in flats in defined growth conditions, controlling for temperature (16-24° C.) and 12 hours photoperiod. The control pots contained 2 g of untreated perlite. The experimental pots were treated with perlite impregnated with 2 mL of the 22 bacteria shown in Table 4. The impregnated perlite had been stored dry for two weeks prior to use in this assay. The flats were watered 3 times a week with modified Hoagland solution. After 28 to 32 days, shoots were dried, and weights were recorded for each plant. The data were analyzed by One-way ANOVA (Analysis Of Variance) and with post-hoc Tukey test to compare samples within the experiment. Shoot dry weight was increased in plants treated with the microbe-impregnated perlite, though it did not reach statistical significance (FIG. 5). As described in Example 4 (Table 17) mainly microbes with identified DPA genes and/or with detectable DPA production survived on impregnated perlite, a subset of the starting consortium.

Example 12

DPA Producing Consortium

To identify suitable strains for use in designing an additional DPA producing consortium, an in-house microbial collection was screened. Strains derived from genera that are known to sporulate were revived from bacterial glycerol stocks on appropriate media and allowed to grow for up to three days. Single colonies were then selected and passaged at least three times to verify purity. Strains were tested for DPA production using the terbium-DPA fluorescence assay as described in Example 1. Strains shown to produce DPA were selected for whole-genome sequencing. Whole-genome sequencing of biologically pure isolates was performed using Illumina NovaSeq 6000 sequencing system (Illumina, Inc., San Diego, CA USA) following the manufacturer's recommended method for sequence library preparation and sequencing. An average of 5,133,928 reads of 87 bp in length on average were generated from the microbial isolates. De novo genome assembly was performed using SPAdes 3.12.0 (Nurk et al., *J. Comput. Biol.* 20:714-737, 2013). Assembled contigs were then annotated with PROKKA (Seemann, *Bioinformatics* 30(14):2068-2069, 2014). Annotated genomes were then assessed for the presence of Dipicolinate Synthase subunit A (DpaA) and Dipicolinate Synthase subunit B (DpaB) and Iron-sulfur Flavoprotein (Isf, Table 25). In most cases, strains that produced DPA possessed both DpaA and DpaB genes and lacked Isf genes. All strains that produced DPA and lacked DpaA and DpaB possessed one or more copies of Isf genes. In three cases strains possessed all three (DpaA, DpaB, and Isf) genes. Therefore, detection of DPA production via the terbium-DPA fluorescence assay was perfectly correlated with the presence of DpaA, DpaB, and/or Isf genes.

TABLE 25

Whole-genome taxonomic classification, DPA-production, and gene copy number for DpaA, DpaB, and Isf

| Whole Genome ID | DPA-production | Gene Copy Number DpaA | DpaB | Isf |
|---|---|---|---|---|
| *Bacillus megaterium* | 1 | 1 | 1 | 0 |
| *Bacillus koreensis* | 1 | 1 | 1 | 0 |
| *Bacillus clausii* | 1 | 1 | 1 | 0 |
| *Clostridium beijerinckii* | 1 | 0 | 0 | 6 |
| *Bacillus subtilis* | 1 | 1 | 1 | 0 |
| *Clostridium* sp. (*carboxidivorans*) | 1 | 0 | 0 | 1 |
| *Paenibacillus cookii* | 1 | 1 | 1 | 0 |
| *Clostridium* sp. (*scatologenes*) | 1 | 0 | 0 | 1 |
| *Bacillus licheniformis* | 1 | 1 | 1 | 0 |
| *Paenibacillus lautus* | 1 | 1 | 1 | 0 |
| *Brevibacillus* sp. (*choshinensis*) | 1 | 1 | 1 | 0 |
| *Bacillus amyloliquefaciens* | 1 | 1 | 1 | 0 |
| *Bacillus* sp. (*pocheonensis*) | 1 | 1 | 1 | 0 |
| *Lysinibacillus* sp. (*fusiformis*) | 1 | 1 | 1 | 0 |
| *Lysinibacillus* sp. (*chungkukjangi*) | 1 | 1 | 1 | 0 |
| *Bacillus pumilus* | 1 | 1 | 1 | 0 |
| *Rummeliibacillus* sp. (pycnus) | 1 | 1 | 1 | 0 |
| *Bacillus cereus* | 1 | 1 | 1 | 1 |
| *Paenibacillus chibensis* | 1 | 1 | 1 | 0 |
| *Bacillus flexus* | 1 | 1 | 1 | 0 |
| *Brevibacillus parabrevis* | 1 | 1 | 1 | 0 |
| *Bacillus aryabhattai* | 1 | 1 | 1 | 0 |
| *Paenibacillus* sp. (*amylolyticus*) | 1 | 1 | 1 | 0 |
| *Clostridium beijerinckii* | 1 | 0 | 0 | 11 |
| *Bacillus subtilis* | 1 | 1 | 1 | 0 |
| *Paenibacillus* sp. (*chitinolyticus*) | 1 | 1 | 1 | 0 |
| *Bacillus* sp. (*wudalianchiensis*) | 1 | 1 | 1 | 0 |
| *Paenibacillus larvae* | 1 | 1 | 1 | 0 |
| *Bacillus licheniformis* | 1 | 3 | 3 | 0 |
| *Paenibacillus* sp. (*agaridevorans*) | 1 | 1 | 1 | 0 |
| *Clostridium* sp. (*tyrobutyricum*) | 1 | 0 | 0 | 1 |
| *Paenibacillus* sp. (*alvei*) | 1 | 1 | 1 | 0 |
| *Bacillus* sp. (*selenatarsenatis*) | 1 | 1 | 1 | 0 |
| *Paenibacillus* sp. (P1XP2) | 1 | 1 | 1 | 0 |
| *Fontibacillus* sp. (*panacisegetis*) | 1 | 1 | 1 | 0 |
| *Bacillus firmus* | 1 | 1 | 1 | 0 |
| *Bacillus subtilis* | 1 | 1 | 1 | 0 |

TABLE 25-continued Whole-genome taxonomic classification, DPA-production, and gene copy number for DpaA, DpaB, and Isf

| Whole Genome ID | DPA-production | DpaA | DpaB | Isf |
|---|---|---|---|---|
| Lysinibacillus sp. (chungkukjangi) | 1 | 1 | 1 | 0 |
| Paenibacillus sp. (ehimensis) | 1 | 1 | 1 | 0 |
| Paenibacillus lactis | 1 | 1 | 1 | 0 |
| Bacillus farraginis | 1 | 1 | 1 | 0 |
| Paenibacillus sp. (P1XP2) | 1 | 1 | 1 | 0 |
| Brevibacillus massiliensis | 1 | 1 | 1 | 0 |
| Paenibacillus azoreducens | 1 | 1 | 1 | 0 |
| Bacillus litoralis | 1 | 1 | 1 | 0 |
| Bacillus endophyticus | 1 | 1 | 1 | 0 |
| Paenibacillus xylanexedens | 1 | 1 | 1 | 0 |
| Bacillus frigoritolerans | 1 | 1 | 1 | 0 |
| Bacillus velezensis | 1 | 1 | 1 | 0 |
| Clostridium aerotolerans | 1 | 1 | 1 | 1 |
| Sphingomonas koreensis | 1 | 0 | 0 | 2 |
| Clostridium beijerinckii | 1 | 0 | 0 | 10 |
| Clostridium aerotolerans | 1 | 1 | 1 | 2 |
| Brevibacillus sp. (brevis) | 1 | 2 | 2 | 0 |
| Bacillus sp. (cereus) | 1 | 1 | 1 | 0 |
| Bacillus badius | 1 | 1 | 1 | 0 |
| Bacillus aryabhattai | 1 | 1 | 1 | 0 |
| Bacillus anthracis | 1 | 1 | 1 | 0 |
| Bacillus flexus | 1 | 1 | 1 | 0 |
| Bacillus drentensis | 1 | 1 | 1 | 0 |
| Bacillus sp. (cuccumis) | 1 | 1 | 1 | 0 |
| Paenibacillus peoriae | 1 | 1 | 1 | 0 |
| Bacillus sp. (cereus) | 1 | 1 | 1 | 0 |
| Bacillus aryabhattai | 1 | 1 | 1 | 0 |
| Bacillus sp. (solani) | 1 | 1 | 1 | 0 |
| Terribacillus sp. (aidingensis) | 1 | 1 | 1 | 0 |
| Bacillus sp. (circulans) | 1 | 1 | 1 | 0 |
| Brevibacterium frigoritolerans | 1 | 1 | 1 | 0 |

The DPA production column represents those strains that test positive for DPA production via the Terbium-DPA fluorescence assay, 1 = detected and 0 = not detected or below detection limit.

For strains that tested positive for DPA production, potential microbial metabolic activities (such as but not limited to nitrogen metabolism, sulfur metabolism, salt tolerance, mineral salt solubilization, cellulose degradation, chitin degradation, phytohormone production, iron metabolism, dephosphorylation of organic matter) were assessed using laboratory assays as described in WO 2018/045004 and Example 1. Strains possessing the greatest number of metabolic activities were selected for co-fermentation in microbial consortia along with 5 strains that lack DPA production which were selected for their metabolic activities (see Example 1). Those strains that proved to be amenable to co-fermentation in consortium (see Table 26), also referred to herein as Dry Formulation Consortium (DFC), were selected for co-formulation with a carrier such as bentonite, perlite and/or urea.

All consortia included in this example were fermented as follows. Both aerobic and anaerobic bacteria strains were cultured on medium containing 2-10% sugar source. Amino acids, nitrogen and peptides were provided in the form of one or more of the following: food grade whey powder (0.1-0.5% w/v), yeast extract (0.1-0.5% w/v), non-GMO soybean extract produced enzymatically (0.1-0.5% w/v; Ferti-Nitro Plus Plant N; Ferti-Organic, Brownsville, TX USA), spirulina (0.1-0.5% w/v), and/or peptone (0.1-0.5% w/v). When needed, additional vitamins and micronutrients were provided by kelp extract (0.1-0.5% w/v), purified B-vitamins (Sigma), and/or Wolfe's trace metal solution. When needed, additional salts were added as phosphate buffered saline solution and/or sodium chloride addition (0-4% w/v). Strains from AMC1 (described above) were inoculated into 2 L DASGIP bioreactors (Eppendorf North America Hauppauge, NY) with a 1.5 liter working volume. The pH during fermentation was maintained between 5.0 and 7.0. Aeration conditions during fermentation were controlled by varying agitation, gas composition (air and/or nitrogen gas) and gas flow rates to obtain target oxygen transfer rate (estimated by using $k_La$) and ranged from having a $k_La$ (per hour) of 0 to 110. Temperature was controlled between 28° C. and 35° C.

TABLE 26

Co-cultivated consortium ("DFC") designed for co-formulation with carriers or as seed treatment

| Taxonomy | DPA-production |
|---|---|
| Bacillus amyloliquefaciens | 1 |
| Bacillus firmus | 1 |
| Bacillus flexus | 1 |
| Bacillus licheniformis | 1 |
| Bacillus megaterium | 1 |
| Bacillus pumilus | 1 |
| Bacillus koreensis | 1 |
| Bacillus drentensis | 1 |
| Bacillus subtilis | 1 |
| Clostridium bifermentans | 1 |
| Clostridium beijerinckii | 1 |
| Clostridium pasteurianum | 0 |
| Lactobacillus paracasei | 0 |
| Fontibacillus sp. (panacisegetis) | 1 |
| Oceanobacillus oncorhynchi | 0 |
| Paenibacillus lautus | 1 |
| Paenibacillus azoreducens | 1 |
| Paenibacillus chibensis | 1 |
| Paenibacillus cookii | 1 |
| Paenibacillus sp. (chitinolyticus) | 1 |
| Paenibacillus sp. (P1XP2) | 1 |
| Pseudomonas sp. | 0 |
| Streptomyces griseus | 0 |

The DPA production column represents those strains that test positive for DPA production via the Terbium-DPA fluorescence assay, 1 = detected and 0 = not detected or below detection limit.

To produce co-formulations, DFC fermentate was applied to bentonite or perlite, and then dried for approximately 24 hours. In some cases, fermentate was concentrated via centrifugation prior to application. Co-formulations were then tested for viability. In addition, certain co-formulations were tested in the plant growth room trials to verify plant beneficial characteristics.

Viability of DFC and AMC1 with carriers: In preparation for field trials that included DFC liquid, AMC1 liquid, DFC-impregnated perlite, AMC1-impregnated perlite, DFC-impregnated bentonite, and AMC1-impregnated bentonite, DFC and AMC1 were each co-fermented and perlite or bentonite carriers were impregnated with 2 mL/g or 1 mL/g respectively. The impregnated perlite and bentonite were stored dry for one to three weeks, at which point the viability assay was performed to determine the number of strains that were viable at the time of application. In addition, liquid was stored for one week, at which point the viability assay was performed to determine the number of strains that were viable at the time of application. In liquid, 16 out of 23 DFC strains were viable after one week versus 14 out of 22 AMC1 strains (Table 27).

TABLE 27

Viability of DFC and AMC1 consortia in liquid following aging

| | DFC Liquid T0 - At Application | AMC1 Liquid |
|---|---|---|
| *Bacillus amyloliquefaciens* | 1 | 1 |
| *Bacillus flexus* | 0 | 1 |
| *Bacillus licheniformis* | 1 | 1 |
| *Bacillus megaterium* | 1 | 1 |
| *Bacillus subtilis* | 0 | 0 |
| *Paenibacillus chibensis* | 1 | 1 |
| *Paenibacillus cookii* | 1 | 1 |
| *Oceanobacillus oncorhynchi* | 0 | 1 |
| *Paenibacillus lautus* | 1 | 1 |
| *Clostridium beijerinckii* | 1 | 1 |
| *Clostridium pasteurianum* | 1 | 1 |
| *Lactobacillus paracasei* | 1 | 1 |
| *Pseudomonas* sp. | 0 | 0 |
| *Streptomyces griseus* | 1 | 0 |
| *Bacillus koreensis* | 0 | |
| *Bacillus pumilus* | 1 | |
| *Paenibacillus* sp. (*chitinolyticus*) | 1 | |
| *Paenibacillus* sp. (P1XP2) | 1 | |
| *Fontibacillus* sp. (*panacisegetis*) | 1 | |
| *Bacillus firmus* | 0 | |
| *Clostridium bifermentans* | 1 | |
| *Paenibacillus azoreducens* | 1 | |
| *Bacillus drentensis* | 0 | |
| *Bacillus* sp. | | 0 |
| *Virgibacillus halophilus* | | 0 |
| *Acetobacter pasteurianus* | | 1 |
| *Azotobacter vinelandii* | | 0 |
| *Lactobacillus buchneri* | | 1 |
| *Lactobacillus delbrueckii* | | 0 |
| *Lactobacillus vini* | | 1 |
| *Pseudomonas putida* | | 0 |
| Total # Viable: | 16 | 14 |

1 = detected and 0 = not detected or below detection limit

On impregnated perlite, 17 out of 23 DFC strains versus 14 out of 22 AMC1 strains were viable after up to three weeks (Table 28).

TABLE 28

Viability of DFC and AMC1 consortia impregnated on perlite following aging.

| | DFC Perlite T0 - At Application | AMC1 Perlite |
|---|---|---|
| *Bacillus amyloliquefaciens* | 1 | 1 |
| *Bacillus flexus* | 1 | 1 |
| *Bacillus licheniformis* | 1 | 1 |
| *Bacillus megaterium* | 1 | 1 |
| *Bacillus subtilis* | 1 | 1 |
| *Paenibacillus chibensis* | 1 | 1 |
| *Paenibacillus cookii* | 1 | 1 |
| *Oceanobacillus oncorhynchi* | 0 | 0 |
| *Paenibacillus lautus* | 1 | 1 |
| *Clostridium beijerinckii* | 1 | 1 |
| *Clostridium pasteurianum* | 1 | 1 |
| *Lactobacillus paracasei* | 0 | 1 |
| *Pseudomonas* sp. | 0 | 0 |
| *Streptomyces griseus* | 0 | 0 |
| *Bacillus koreensis* | 1 | |
| *Bacillus pumilus* | 1 | |
| *Paenibacillus* sp. (*chitinolyticus*) | 1 | |
| *Paenibacillus* sp. (P1XP2) | 1 | |
| *Fontibacillus* sp. (*panacisegetis*) | 1 | |
| *Bacillus firmus* | 1 | |
| *Clostridium bifermentans* | 0 | |
| *Paenibacillus azoreducens* | 1 | |
| *Bacillus drentensis* | 0 | |
| *Bacillus* sp. | | 1 |
| *Virgibacillus halophilus* | | 0 |
| *Acetobacter pasteurianus* | | 1 |
| *Azotobacter vinelandii* | | 0 |
| *Lactobacillus buchneri* | | 1 |
| *Lactobacillus delbrueckii* | | 0 |
| *Lactobacillus vini* | | 0 |
| *Pseudomonas putida* | | 0 |
| Total # Viable: | 17 | 14 |

1 = detected and 0 = not detected or below detection limit.

On impregnated bentonite, 17 out of 23 DFC strains versus 14 out of 22 AMC1 strains were viable after up to three weeks (Table 29). This illustrates how DPA-producing strains maintain improved viability when stored in liquid, as well as when dried on a carrier such as perlite or bentonite.

TABLE 29

Viability of DFC and AMC1 consortia impregnated on bentonite following aging

| | DFC Bentonite T0 - At Application | AMC1 Bentonite |
|---|---|---|
| *Bacillus amyloliquefaciens* | 1 | 1 |
| *Bacillus flexus* | 1 | 1 |
| *Bacillus licheniformis* | 1 | 1 |
| *Bacillus megaterium* | 1 | 1 |
| *Bacillus subtilis* | 1 | 1 |
| *Paenibacillus chibensis* | 1 | 1 |
| *Paenibacillus cookii* | 1 | 1 |
| *Oceanobacillus oncorhynchi* | 0 | 0 |
| *Paenibacillus lautus* | 1 | 1 |
| *Clostridium beijerinckii* | 1 | 1 |
| *Clostridium pasteurianum* | 1 | 1 |
| *Lactobacillus paracasei* | 1 | 1 |
| *Pseudomonas* sp. | 0 | 0 |
| *Streptomyces griseus* | 0 | 0 |
| *Bacillus koreensis* | 0 | |
| *Bacillus pumilus* | 1 | |
| *Paenibacillus* sp. (*chitinolyticus*) | 1 | |
| *Paenibacillus* sp. (P1XP2) | 1 | |
| *Fontibacillus* sp. (*panacisegetis*) | 1 | |
| *Bacillus firmus* | 1 | |
| *Clostridium bifermentans* | 0 | |
| *Paenibacillus azoreducens* | 1 | |
| *Bacillus drentensis* | 0 | |
| *Bacillus* sp. | | 1 |
| *Virgibacillus halophilus* | | 0 |
| *Acetobacter pasteurianus* | | 0 |
| *Azotobacter vinelandii* | | 0 |
| *Lactobacillus buchneri* | | 1 |
| *Lactobacillus delbrueckii* | | 0 |
| *Lactobacillus vini* | | 1 |
| *Pseudomonas putida* | | 0 |
| Total # Viable: | 17 | 14 |

1 = detected and 0 = not detected or below detection limit.

Following 3 months of aging, DFC-impregnated perlite showed 15 strains as viable, whereas AMC1-impregnated perlite showed only 11 strains as viable and only one of which was not DPA producing (Tables 30 and 31).

TABLE 30

Viability of AMC1 impregnated on perlite and bentonite over time

| | DPA | Perlite - 3 months | Bentonite - 3 months |
|---|---|---|---|
| *Bacillus amyloliquefaciens* | 1 | 1 | 1 |
| *Bacillus flexus* | 1 | 1 | 1 |
| *Bacillus licheniformis* | 1 | 1 | 1 |
| *Bacillus megaterium* | 1 | 1 | 1 |
| *Bacillus* sp. | 1 | 0 | 0 |
| *Bacillus subtilis* | 1 | 1 | 1 |
| *Paenibacillus chibensis* | 1 | 1 | 1 |
| *Paenibacillus cookii* | 1 | 1 | 1 |
| *Oceanobacillus oncorhynchi* | 1 | 1 | 1 |
| *Paenibacillus lautus* | 1 | 1 | 1 |
| *Virgibacillus halophilus* | 0 | 0 | 0 |
| *Clostridium beijerinckii* | 1 | 1 | 1 |
| *Acetobacter pasteurianus* | 0 | 0 | 0 |
| *Azotobacter vinelandii* | 0 | 0 | 0 |
| *Clostridium pasteurianum* | 0 | 1 | 1 |
| *Lactobacillus buchneri* | 0 | 0 | 1 |
| *Lactobacillus delbrueckii* | 0 | 0 | 0 |
| *Lactobacillus paracasei* | 0 | 0 | 1 |
| *Lactobacillus vini* | 0 | 0 | 0 |
| *Pseudomonas putida* | 0 | 0 | 0 |
| *Pseudomonas* sp. | 0 | 0 | 0 |
| *Streptomyces griseus* | 0 | 0 | 0 |
| Total # Viable: | | 11 | 13 |

The DPA column represents those strains that test positive for DPA production via the Terbium-DPA fluorescence assay. 1 = detected and 0 = not detected or below detection limit.

Following the same 3 months of aging, DFC-impregnated bentonite showed 19 strains as viable, whereas AMC1-impregnated perlite showed on 13 strains as viable and only three of which were not DPA producing (Tables 30 and 31).

TABLE 31

Viability of DFC impregnated on perlite and bentonite over time

| | DPA | Perlite - 3 months | Bentonite - 3 months |
|---|---|---|---|
| *Bacillus amyloliquefaciens* | 1 | 1 | 1 |
| *Bacillus flexus* | 1 | 0 | 1 |
| *Bacillus licheniformis* | 1 | 1 | 1 |
| *Bacillus megaterium* | 1 | 1 | 1 |
| *Bacillus subtilis* | 1 | 1 | 1 |
| *Paenibacillus chibensis* | 1 | 1 | 1 |
| *Paenibacillus cookii* | 1 | 1 | 1 |
| *Oceanobacillus oncorhynchi* | 1 | 1 | 1 |
| *Paenibacillus lautus* | 1 | 1 | 1 |
| *Clostridium beijerinckii* | 1 | 1 | 1 |
| *Clostridium pasteurianum* | 0 | 1 | 1 |
| *Lactobacillus paracasei* | 0 | 0 | 1 |
| *Pseudomonas* sp. | 0 | 0 | 0 |
| *Streptomyces griseus* | 0 | 0 | 0 |
| *Bacillus koreensis* | 1 | 0 | 1 |
| *Bacillus pumilus* | 1 | 1 | 1 |
| *Paenibacillus* sp. (*chitinolyticus*) | 1 | 1 | 1 |
| *Paenibacillus* sp. (P1XP2) | 1 | 1 | 1 |
| *Fontibacillus* sp. (*panacisegetis*) | 1 | 1 | 1 |
| *Bacillus firmus* | 1 | 0 | 1 |
| *Clostridium bifermentans* | 0 | 0 | 0 |
| *Paenibacillus azoreducens* | 1 | 1 | 1 |
| *Bacillus drentensis* | 1 | 0 | 0 |
| Total # viable: | | 15 | 19 |

The DPA column represents those strains that test positive for DPA production via the Terbium-DPA fluorescence assay. 1 = detected and 0 = not detected or below detection limit.

Evaluation of DFC Plant Beneficial Activity: Cucumber seeds purchased from The Seed Kingdom (Lubbock, TX) were pre-germinated for 4 days at 22° C. in rolled germination paper (Anchor Paper, Saint Paul, MN) impregnated with a dilute mixture of liquid fertilizer (25 ppm NPK in water). At the time of seed preparation, the potting medium (Sunshine Mix) was prepared with a pre-treatment of 67.60 kg Tricalcium phosphate (TCP) ha$^{-1}$ and a modified Hoagland solution (Hoagland, CA Agric. Exp. Stn. Bull. 347:36-39, 1938). This Hoagland solution, NK+ was modified to contain N, 56.03 ppm; P, 0 ppm; K, 39.1 ppm; Ca, 40.0 ppm; Mg, 14.59 ppm; S, 20.143 ppm; Fe, 1.010 ppm; Cu, 0.019 ppm; Co, 0.012 ppm; B, 2.44 ppm; Mn, 0.494 ppm; Mo, 0.001 ppm and Zn, 0.056 ppm, which was applied a rate of 1 L per pound of potting medium. The control treatments also contained 10 g of untreated perlite or 20 g of untreated bentonite per pound of potting medium. In comparison, the experimental pots had the same amount of perlite or bentonite as the control pots however those carriers were impregnated with 2 mL/g of DFC or 1 mL/g of DFC, respectively. The impregnated perlite and bentonite had been stored dry for two weeks prior to use in this assay, at which point the viability assay was performed to determine the number of strains from DFC that were viable at the time of application. The large majority of strains (15-18 out of 23 strains viable) survived the co-formulation and aging process.

Following the pre-germination of the cucumber seeds, similar length seedling were selected and one was transplanted into each pot. For each treatment (including control) 18 plants were randomized in flats in defined growth conditions, controlling for temperature (16-24° C.) and 12 hours photoperiod. The flats were watered for the first time three days after transplanting with a modified Hoagland solution, PK+ which contains N, 0 ppm; P, 14.49 ppm; K, 19.55 ppm; Ca, 20.0 ppm; Mg, 14.59 ppm; S, 20.143 ppm; Fe, 1.010 ppm; Cu, 0.019 ppm; Co, 0.012 ppm; B, 2.44 ppm; Mn, 0.494 ppm; Mo, 0.001 ppm and Zn, 0.056 ppm. The flats were then watered 3 times a week with NK+ Hoagland solution. After 32 days, shoots were harvested, and dried weights were recorded for each plant. The data were analyzed by One-way ANOVA (Analysis Of Variance) and with a post-hoc Tukey test to compare samples within the experiment. These trials were performed twice on two separate occasions.

Figure 6:
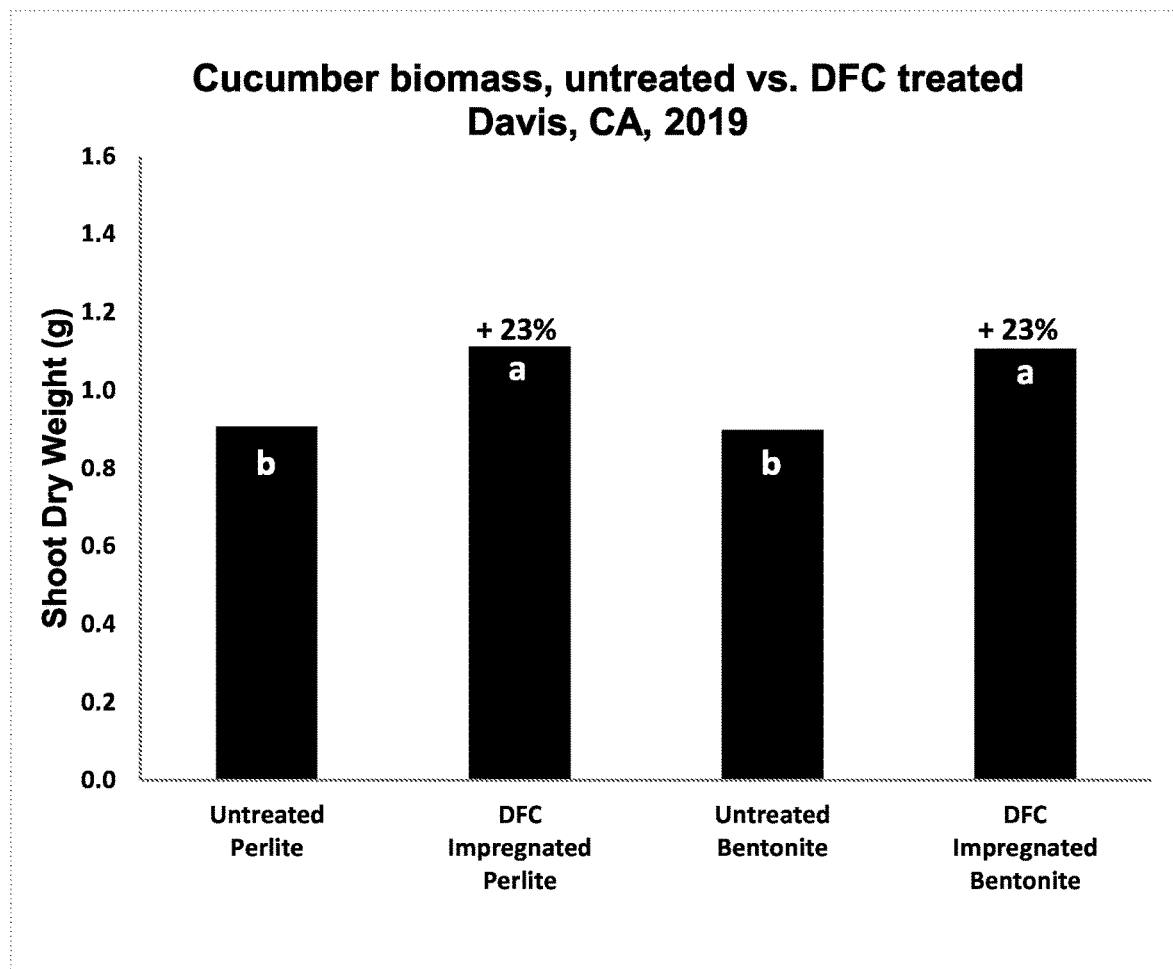
FIG. 6 is a graph showing 32 day cucumber shoot dry weight in plants treated with perlite, perlite impregnated with DFC microbial consortium, bentonite, and bentonite impregnated with DFC microbial consortium.
Figure 7:
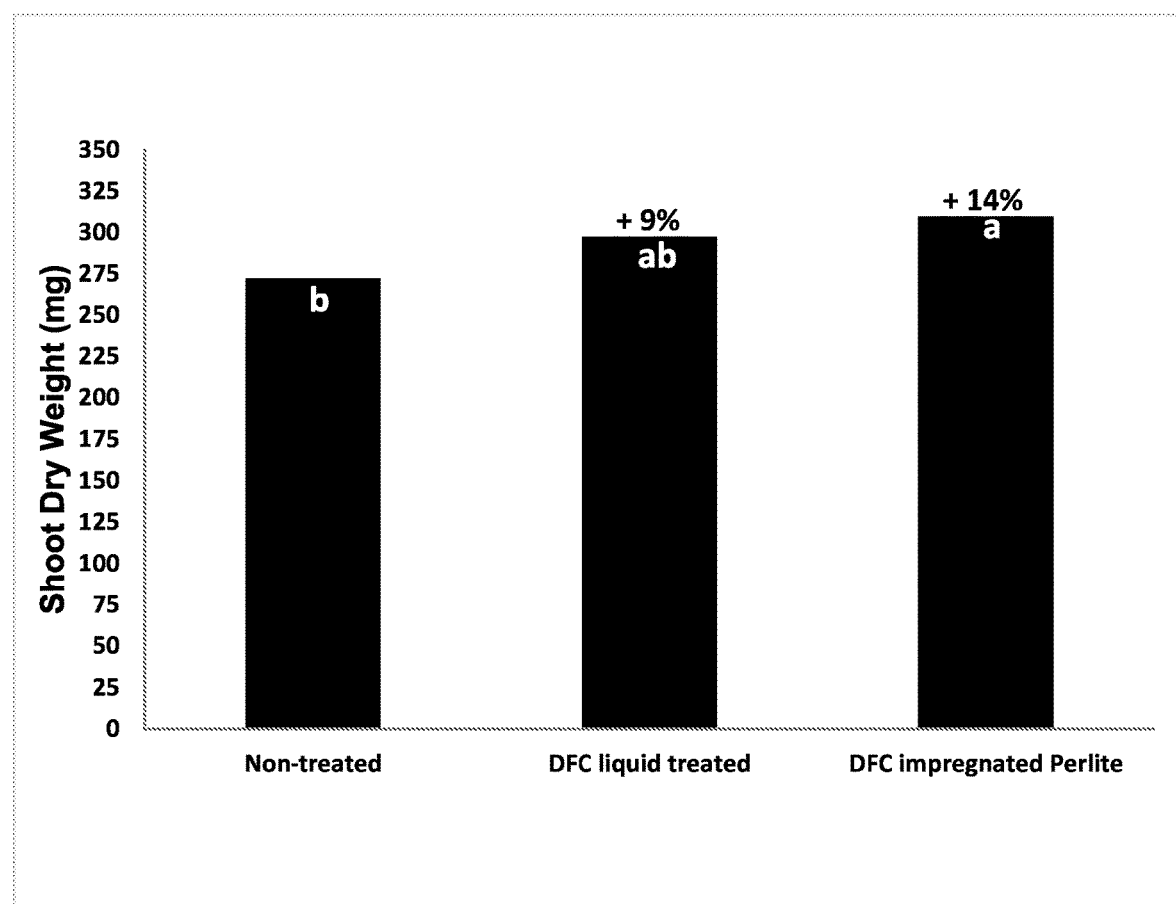
FIG. 7 is a graph showing 32 day cucumber shoot dry weight in untreated plants, plants treated with liquid DFC consortium, and plants treated with perlite impregnated with DFC microbial consortium.

The results of the initial trial showed a significant increase in shoot weight for both DFC impregnated perlite and DFC impregnated bentonite when compared to controls (FIG. 6). The results of the second trial also showed a significant increase in shoot weight for both DFC liquid treatment and DFC impregnated perlite, and while the DFC impregnated perlite performed better that the DFC liquid treatment, they were not significantly different (FIG. 7). Thus, co-formulation with a carrier did not impact efficacy when compared to fresh liquid product.

Example 13

Microbe Seed Treatment

Microbe seed treatments were applied to corn and soybean seed using a batch treater SGS (SGS North America, Brookings, SD USA). One kg of seed was treated for each treatment. In separate seed treatments, microbes were either applied directly to untreated seed, applied as an overcoat to seed previously treated with an insecticide/fungicide package, or mixed with the insecticide/fungicide slurry prior to seed application. For corn, insecticide/fungicide treatment consisted of either an Acceleron mix containing metalaxyl, trifloxystrobin, ipconazole, and clothianidin, or a CruiserMaxx mix containing Cruiser (thiamethoxam), fludioxonil, mefenoxam, azoxystrobin, and thiabendazole. For soybean, insecticide/fungicide treatment consisted of either an Acceleron mix containing metalaxyl, pyraclostrobin, imidacloprid, and fluxapyroxad, or a CrusierMaxx mix containing Cruiser (thiamethoxam), mefenoxam, fludioxonil, and sedexane.

Figure 8:
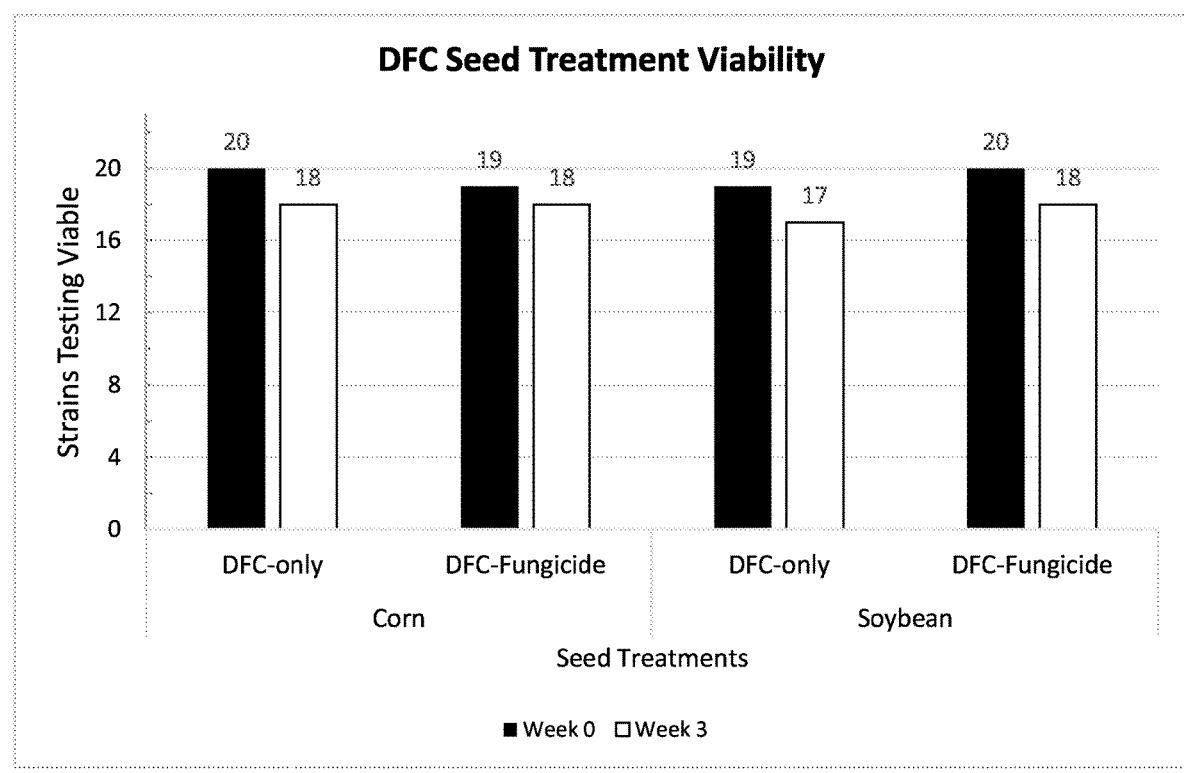
FIG. 8 is a graph showing survival of bacteria from DFC consortium in combination with corn and soybean seeds, along with insecticide/fungicide treatments.

Following seed treatment, viability was tested (as in Example 1) within 48 hours and three weeks thereafter. The overwhelming majority of strains (19-20 out of 23 strains viable) survived the initial co-formulation process. After three weeks, only a slight reduction in viability was observed (17-18 out of 23 strains viable; FIG. 8). This illustrated that selecting DPA producing strains was effective not only for dry fertilizers such as bentonite and perlite, but also effective as a seed treatment. In addition, seeds were tested for germination to determine the impact of seed treatment on germination potential. A Cold Vigor test was performed, where 4 replications of 100 seeds were tested for germination. Each 100 seed replicate was planted on moistened crepe cellulose paper and chilled overnight at 10° C. The seeds were then covered with one inch of non-sterile sand wet to 70% water holding capacity and returned to 10° C. for seven days without light. The seeds were then moved into 25° C. for four days. Seedlings that emerged through the sand were evaluated. Results were reported as a percentage that represents the number of seedlings categorized as normal according to AOSA rules. Scores of 82% or higher are considered to be the minimum acceptable for marketing a corn seed lot according to Iowa State Seed Lab and SGS. All treatments had a germination percentage of at least 83.8% or greater (Table 32). This illustrates that in addition to performing well in the form of a seed treatment, DPA-producing strains did not negatively impact germination of said seeds.

TABLE 32

Average germination rate of DFC treated corn and soybean seeds using the cold vigor germination test

| | Corn | | Soybean | |
| --- | --- | --- | --- | --- |
| | Untreated | DFC | Untreated | DFC |
| No Fungicide Treatment | 90.30% | 87.50% | 87.50% | 83.80% |
| Acceleron Treated | 89.30% | 87.90% | 86.00% | 84.90% |
| CruiserMaxx Treated | 88.00% | 86.00% | 85.00% | 88.65% |

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of improving plant growth, improving stress tolerance, and/or increasing crop yield, comprising contacting soil, plants, plant parts, or seeds with a composition comprising cells of microbial species including or consisting of microbes with 16S rDNA nucleic acid sequences having at least 99% sequence identity to each of SEQ ID NOs: 3-25.

2. The method of claim 1, further comprising contacting the soil, plants, plant parts, or seeds with:
- one or more of chitin, chitosan, glucosamine, and amino acids;
- a liquid fertilizer; and/or
- one or more pesticides, one or more fungicides, one or more herbicides, one or more insecticides, one or more plant hormones, one or more plant elicitors, or combinations of two or more thereof.

3. The method of claim 1, further comprising activating the microbial species in the composition prior to contacting the soil, plants, plant parts, or seeds with the composition.

4. The method of claim 1, wherein the composition further comprises a carrier or a seed.

5. The method of claim 1, wherein the composition comprises cells of microbial species including or consisting of microbes with 16S rDNA nucleic acid sequences of each of SEQ ID NOs: 3-25.

6. The method of claim 4, wherein the carrier comprises urea, potash, ammonium phosphate, ammonium nitrate, clay, peat, coal, inorganic soil, charcoal, sawdust, wheat/soy/oat bran, compost, coco coir, perlite, vermiculite, bentonite, kaolin, silicates, pumice, talc, a liquid fertilizer or a liquid dust control chemical.

7. The method of claim 4, wherein the seed comprises corn seed, sunflower seed, canola seed, wheat seed, cucumber seed, tomato seed, rice seed, and/or cotton seed.

8. The method of claim 4, further comprising one or more insecticide and/or fungicide.

9. A method of improving plant growth, improving stress tolerance, and/or increasing crop yield, comprising contacting soil, plants, plant parts, or seeds with a composition comprising American Type Culture Collection deposit number PTA-125924.

10. The method of claim 9, further comprising contacting the soil, plants, plant parts, or seeds with:
- one or more of chitin, chitosan, glucosamine, and amino acids;
- a liquid fertilizer; and/or
- one or more pesticides, one or more fungicides, one or more herbicides, one or more insecticides, one or more plant hormones, one or more plant elicitors, or combinations of two or more thereof.

11. The method of claim 9, further comprising activating the microbial species in the composition prior to contacting the soil, plants, plant parts, or seeds with the composition.

12. The method of claim 9, wherein the composition further comprises a carrier or a seed.

13. The method of claim 12, wherein the carrier comprises urea, potash, ammonium phosphate, ammonium nitrate, clay, peat, coal, inorganic soil, charcoal, sawdust, wheat/soy/oat bran, compost, coco coir, perlite, vermiculite, bentonite, kaolin, silicates, pumice, talc, a liquid fertilizer or a liquid dust control chemical.

14. The method of claim 12, wherein the seed comprises corn seed, sunflower seed, canola seed, wheat seed, cucumber seed, tomato seed, rice seed, and/or cotton seed.

15. The method of claim 12, further comprising one or more insecticide and/or fungicide.

* * * * *

SEQUENCE LISTING

<160> NUMBER OF SEQ ID NOS: 67

<210> SEQ ID NO 1
<211> LENGTH: 1524
<212> TYPE: DNA
<213> ORGANISM: Streptomyces pratensis

<400> SEQUENCE: 1

```
catggagagt ttgatcctgg ctcaggacga acgctggcgg cgtgcttaac acatgcaagt    60
cgaacgatga agcccttcgg ggtggattag tggcgaacgg gtgagtaaca cgtgggcaat   120
ctgcccttca ctctgggaca gcccggaa acggggtcta ataccggata acactctgtc   180
cctcatgggg cggggttaaa agctccggcg gtgaaggatg agcccgcggc ctatcagctt   240
gttggtgggg taatggccta ccaaggcgac gacgggtagc cggcctgaga gggcgaccgg   300
ccacactggg actgagacac ggcccagact cctacgggag gcagcagtgg ggaatattgc   360
acaatgggcg aaagcctgat gcagcgacgc cgcgtgaggg atgacggcct tcgggttgta   420
aacctctttc agcagggaag aagcgcaagt gacggtacct gcagaagaag caccggctaa   480
ctacgtgcca gcagccgcgg taatacgtag ggtgcgagcg ttgtccggaa ttattgggcg   540
taaagagctc gtaggcggct tgtcacgtcg gatgtgaaag ctcggggctt aaccccgagt   600
ctgcattcga tacgggctag ctagagtgtg taggggaga tcggaattcc tggtgtagcg   660
gtgaaatgcg cagatatcag gaggaacacc ggtggcgaag gcggatctct gggccattac   720
tgacgctgag gagcgaaagc gtggggagcg aacaggatta gataccctgg tagtccacgc   780
cgtaaacgtt gggaactagg tgttggcgac attccacgtc gtcggtgccg cagctaacgc   840
attaagttcc cgcctgggg agtacggccg caaggctaaa actcaaagga attgacgggg   900
gcccgcacaa gcagcggagc atgtggctta attcgacgca acgcgaagaa ccttaccaag   960
gcttgacata taccggaaag catcagagat ggtgcccccc ttgtggtcgg tatacaggtg  1020
gtgcatggct gtcgtcagct cgtgtcgtga tgttgggt taagtccgc aacgagcgca  1080
acccttgttc tgtgttgcca gcatgccctt cggggtgatg ggactcaca ggagactgcc  1140
ggggtcaact cggaggaagg tggggacgac gtcaagtcat catgccccctt atgtcttggg  1200
ctgcacacgt gctacaatgg ccggtacaat gagctgcgat gccgcgaggc ggagcgaatc  1260
tcaaaaagcc ggtctcagtt cggattgggg tctgcaactc gaccccatga agtcggagtt  1320
gctagtaatc gcagatcagc attgctgcgg tgaatacgtt cccgggcctt gtacacaccg  1380
cccgtcacgt cacgaaagtc ggtaacaccc gaagccggtg gcccaacccc ttgtgggagg  1440
gagctgtcga aggtgggact ggcgattggg acgaagtcgt aacaaggtag ccgtaccgga  1500
aggtgcggct ggatcaccte cttt                                          1524

<210> SEQ ID NO 2
<211> LENGTH: 1524
<212> TYPE: DNA
<213> ORGANISM: Streptomyces venezuelae

<400> SEQUENCE: 2
cacggagagt ttgatcctgg ctcaggacga acgctggcgg cgtgcttaac acatgcaagt    60
cgaacgatga agcccttcgg ggtggattag tggcgaacgg gtgagtaaca cgtgggcaat   120
ctgcccttca ctctgggaca gcccggaa acggggtcta ataccggata acaccggctc   180
ctgcatgggg gctggttaaa agctccggcg gtgaaggatg agcccgcggc ctatcagctt   240
gttggtgggg taatggccta ccaaggcgac gacgggtagc cggcctgaga gggcgaccgg   300
ccacactggg actgagacac ggcccagact cctacgggag gcagcagtgg ggaatattgc   360
acaatgggcg aaagcctgat gcagcgacgc cgcgtgaggg atgacggcct tcgggttgta   420
aacctctttc agcagggaag aagcgaaagt gacggtacct gcagaagaag cgccggctaa   480
ctacgtgcca gcagccgcgg taatacgtag ggcgcaagcg ttgtccggaa ttattgggcg   540
taaagagctc gtaggcggct tgtcacgtcg ggtgtgaaag cccggggctt aaccccgggt   600
```

```
ctgcatccga tacgggcagg ctagagtgtg gtaggggaga tcggaattcc tggtgtagcg      660
gtgaaatgcg cagatatcag gaggaacacc ggtggcgaag gcggatctct gggccattac      720
tgacgctgag gagcgaaagc gtggggagcg aacaggatta gataccctgg tagtccacgc      780
cgtaaacgtt gggaactagg tgttggcgac attccacgtc gtcggtgccg cagctaacgc      840
attaagttcc ccgcctgggg agtacggccg caaggctaaa actcaaagga attgacgggg      900
gcccgcacaa gcagcggagc atgtggctta attcgacgca acgcgaagaa ccttaccaag      960
gcttgacata taccggaaag cattagagat agtgccccct tgtggtcgg tatacaggtg      1020 gtgcatggct gtcgtcagct cgtgtcgtga gatgttgggt taagtcccgc aacgagcgca      1080
acccttgtcc tgtgttgcca gcatgccctt cggggtgatg gggactcaca ggagaccgcc      1140
ggggtcaact cggaggaagg tggggacgac gtcaagtcat catgcccctt atgtcttggg      1200
ctgcacacgt gctacaatgg ccggtacaaa gagctgcgat gccgtgaggc ggagcgaatc      1260
tcaaaaagcc ggtctcagtt cggattgggg tctgcaactc gacccatga agtcggagtt      1320 gctagtaatc gcagatcagc attgctgcgg tgaatacgtt cccgggcctt gtacacaccg      1380
cccgtcacgt cacgaaagtc ggtaacaccc gaagccggtg gcccaacccc ttgtgggagg      1440
gagctgtcga aggtgggact ggcgattggg acgaagtcgt aacaaggtag ccgtaccgga      1500
aggtgcggct ggatcacctc cttt                                            1524

<210> SEQ ID NO 3
<211> LENGTH: 1548
<212> TYPE: DNA
<213> ORGANISM: Bacillus firmus

<400> SEQUENCE: 3
tatggagagt ttgatcctgg ctcaggacga acgctggcgg cgtgcctaat acatgcaagt       60
cgagcggaca gatgggagct tgctccctga agtcagcggc ggacgggtga gtaacacgtg      120
ggcaacctgc ctgtaagact gggataactc cgggaaaccg gggctaatac cggataattc      180
tttccctcac atgagggaaa gctgaaagat ggtttcggct atcacttaca gatgggcccg      240
cggcgcatta gctagttggt gaggtaacgg ctcaccaagg caacgatgcg tagccgacct      300
gagagggtga tcggccacac tgggactgag acacggccca gactcctacg ggaggcagca      360
gtagggaatc ttccgcaatg gacgaaagtc tgacggagca acgccgcgtg agtgatgaag      420
gttttcggat cgtaaaactc tgttgttagg gaagaacaag taccggagta actgccggta      480
ccttgacggt acctaaccag aaagccacgg ctaactacgt gccagcagcc gcggtaatac      540
gtaggtggca agcgttgtcc ggaattattg ggcgtaaagc gcgcgcaggc ggttccttaa      600
gtctgatgtg aaagccccg gctcaaccgg ggagggtcat tggaaactgg gaacttgag      660 tgcagaagag aagagtggaa ttccacgtgt agcggtgaaa tgcgtagaga tgtggaggaa      720
caccagtggc gaaggcgact ctttggtctg taactgacgc tgaggcgcga aagcgtgggg      780
agcaaacagg attagatacc ctggtagtcc acgccgtaaa cgatgagtgc taagtgttag      840
agggtttccg ccctttagtg ctgcagcaaa cgcattaagc actccgcctg gggagtacgg      900
ccgcaaggct gaaactcaaa ggaattgacg ggggcccgca caagcggtgg agcatgtggt      960
ttaattcgaa gcaacgcgaa gaaccttacc aggtcttgac atctcctgac aaccctagag     1020
atagggcgtt ccccttcggg ggacaggatg acaggtggtg catggttgtc gtcagctcgt     1080
gtcgtgagat gttgggttaa gtcccgcaac gagcgcaacc cttgatctta gttgccagca     1140
```

```
ttcagttggg cactctaagg tgactgccgg tgacaaaccg aggaaggtg gggatgacgt   1200 caaatcatca tgccccttat gacctgggct acacacgtgc tacaatggat ggtacaaagg   1260
gctgcgagac cgcgaggtta agcgaatccc ataaaaccat tctcagttcg gattgcaggc   1320
tgcaactcgc ctgcatgaag ccggaatcgc tagtaatcgc ggatcagcat gccgcggtga   1380
atacgttccc gggccttgta cacaccgccc gtcacaccac gagagtttgt aacacccgaa   1440
gtcggtgggg taaccttttg gagccagccg cctaaggtgg gacagatgat tggggtgaag   1500
tcgtaacaag gtagccgtat cggaaggtgc ggctggatca cctcctt           1548
```

<210> SEQ ID NO 4
<211> LENGTH: 1552
<212> TYPE: DNA
<213> ORGANISM: Paenibacillus azoreducens

<400> SEQUENCE: 4

```
cttggagagt ttgatcctgg ctcaggacga acgctggcgg cgtgcctaat acatgcaagt     60
cgagcggatt tgatgaggag cttgctcctc tgatggttag cggcggacgg gtgagtaaca    120
cgtaggcaac ctgcctgcaa gaccgggata actagcggaa acgttagcta ataccggata    180
atttatcgct ttgcatgaag cgataatgaa agacggagca atctgtcact tgcagatggg    240
cctgcggcgc attagctagt tggtgaggta acggctcacc aaggcgacga tgcgtagccg    300
acctgagagg gtgaacggcc acactgggac tgagacacgg cccagactcc tacgggaggc    360
agcagtaggg aatcttccgc aatgggcgaa agcctgacgg agcaacgccg cgtgagtgat    420
gaaggttttc ggatcgtaaa gctctgttgc agggaagaa cgaccgttag agtaactgct    480
aacggagtga cggtacctga aagaaagcc ccggctaact acgtgccagc agccgcggta    540
atacgtaggg ggcaagcgtt gtccggaatt attgggcgta aagcgcgcgc aggcggtcgc    600
ttaagtctgg tgtttaaggc caaggctcaa ccttggttcg cactggaaac tgggtgactt    660
gagtgcagaa gaggagagtg gaattccacg tgtagcggtg aaatgcgtag agatgtggag    720
gaacaccagt ggcgaaggcg actctctggg ctgtaactga cgctgaggcg cgaaagcgtg    780
gggagcaaac aggattagat accctggtag tccacgccgt aaacgatgaa tgctaggtgt    840
tagggttttc gataccctta gtgccgaagt taacacatta gcattccgcc tggggagta    900 cggtcgcaag actgaaactc aaaggaattg acggggaccc gcacaagcag tggagtatgt    960
ggtttaattc gaagcaacgc gaagaacctt accaggtctt gacatccctc tgaccggact   1020
agagatagtc ctttccttcg ggacagagga gacaggtggt gcatggttgt cgtcagctcg   1080
tgtcgtgaga tgttgggtta agtcccgcaa cgagcgcaac ccttgatttt agttgccagc   1140
actttaaggt gggcactcta aaatgactgc cggtgacaaa ccggaggaag gcggggatga   1200
cgtcaaatca tcatgcccct tatgacctgg gctacacacg tactacaatg gccagtacaa   1260
cgggaagcga atcgcgaga tggagccaat cctatcaaag ctggtctcag ttcggattgc   1320
aggctgcaac tcgcctgcat gaagtcggaa ttgctagtaa tcgcggatca gcatgccgcg   1380
gtgaatacgt tcccgggtct tgtacacacc gcccgtcaca ccacgagagt ttacaacacc   1440
cgaagtcggt gaggtaaccg caaggagcca gccgccgaag gtggggtaga tgattggggt   1500
gaagtcgtaa caaggtagcc gtatcggaag gtgcggctgg atcacctcct tt           1552
```

<210> SEQ ID NO 5
<211> LENGTH: 1548
<212> TYPE: DNA
<213> ORGANISM: Bacillus amyloliquefaciens

<400> SEQUENCE: 5

```
atcggagagt tgatcctgg ctcaggacga acgctggcgg cgtgcctaat acatgcaagt       60
cgagcggaca gatgggagct tgctccctga tgttagcggc ggacgggtga gtaacacgtg      120
ggtaacctgc ctgtaagact gggataactc cgggaaaccg gggctaatac cggatggttg      180
tctgaaccgc atggttcaga cataaaaggt ggcttcggct accacttaca gatgacccg       240
cggcgcatta gctagttggt gaggtaacgg ctcaccaagg cgacgatgcg tagccgacct      300
gagagggtga tcggccacac tgggactgag acacggccca gactcctacg ggaggcagca     360
gtagggaatc ttccgcaatg gacgaaagtc tgacggagca acgccgcgtg agtgatgaag      420
gttttcggat cgtaaagctc tgttgttagg gaagaacaag tgccgttcaa atagggcggc     480
accttgacga tacctaacca gaaagccacg gctaactacg tgccagcagc cgcggtaata     540
cgtaggtggc aagcgttgtc cggaattatt gggcgtaaag ggctcgcagg cggtttctta     600
agtctgatgt gaaagccccc ggctcaaccg ggagggtca ttggaaactg gggaacttga      660
gtgcagaaga ggagagtgga attccacgtg tagcggtgaa atgcgtagag atgtggagga     720
acaccagtgg cgaaggcgac tctctggtct gtaactgacg ctgaggagcg aaagcgtggg     780
gagcgaacag gattagatac cctggtagtc cacgccgtaa acgatgagtg ctaagtgtta     840
gggggtttcc gcccttagt gctgcagcta acgcattaag cactccgcct ggggagtacg      900
gtcgcaagac tgaaactcaa aggaattgac ggggcccgc acaagcggtg gagcatgtgg      960
tttaattcga agcaacgcga agaaccttac caggtcttga catcctctga caatcctaga    1020
gataggacgt cccccttcggg ggcagagtga caggtggtgc atggttgtcg tcagctcgtg   1080
tcgtgagatg ttgggttaag tcccgcaacg agcgcaaccc ttgatcttag ttgccagcat    1140
tcagttgggc actctaaggt gactgccggt gacaaaccgg aggaaggtgg ggatgacgtc    1200
aaatcatcat gccccttatg acctgggcta cacacgtgct acaatggaca gaacaaaggg    1260
cagcgaaacc gcgaggttaa gccaatccca caaatctgtt ctcagttcgg atcgcagtct    1320
gcaactcgac tgcgtgaagc tggaatcgct agtaatgcg gatcagcatg ccgcggtgaa     1380
tacgttcccg ggccttgtac acaccgcccg tcacaccacg agagtttgta acacccgaag    1440
tcggtgaggt aacctttatg agccagccg ccgaaggtgg gacagatgat tggggtgaag    1500
tcgtaacaag gtagccgtat cggaaggtgc ggctggatca cctcctttt              1548
```

<210> SEQ ID NO 6
<211> LENGTH: 1550
<212> TYPE: DNA
<213> ORGANISM: Bacillus flexus

<400> SEQUENCE: 6

```
tcggagagtt tgatcctggc tcaggatgaa cgctggcggc gtgcctaata catgcaagtc      60
gagcgaactg attagaagct tgcttctatg acgttagcgg cggacgggtg agtaacacgt     120
gggcaacctg cctgtaagac tgggataact ccgggaaacc ggagctaata ccggataaca    180
ttttctcttg cataagagaa aattgaaaga tggtttcggc tatcacttac agatgggccc    240
gcggtgcatt agctagttgg tgaggtaacg gctcaccaag gcaacgatgc atagccgacc    300
tgagagggtg atcggccaca ctgggactga gacacggccc agactcctac gggaggcagc   360
agtagggaat cttccgcaat ggacgaaagt ctgacggagc aacgccgcgt gagtgatgaa    420
ggctttcggg tcgtaaaact ctgttgttag ggaagaacaa gtacaagagt aactgcttgt    480
```

-continued

| | |
|---|---|
| accttgacgg tacctaacca gaaagccacg gctaactacg tgccagcagc cgcggtaata | 540 |
| cgtaggtggc aagcgttatc cggaattatt gggcgtaaag cgcgcgcagg cggtttctta | 600 |
| agtctgatgt gaaagcccac ggctcaaccg tgagggtca ttggaaactg gggaacttga | 660 |
| gtgcagaaga gaaaagcgga attccacgtg tagcggtgaa atgcgtagag atgtggagga | 720 |
| acaccagtgg cgaaggcggc ttttggtct gtaactgacg ctgaggcgcg aaagcgtggg | 780 |
| gagcaaacag gattagatac cctggtagtc cacgccgtaa acgatgagtg ctaagtgtta | 840 |
| gagggtttcc gcccttagt gctgcagcta acgcattaag cactccgcct ggggagtacg | 900 |
| gtcgcaagac tgaaactcaa aggaattgac ggggcccgc acaagcggtg gagcatgtgg | 960 |
| tttaattcga agcaacgcga agaaccttac caggtcttga catcctctga caactctaga | 1020 |
| gatagagcgt tccccttcgg gggacagagt gacaggtggt gcatggttgt cgtcagctcg | 1080 |
| tgtcgtgaga tgttgggtta agtcccgcaa cgagcgcaac ccttgatctt agttgccagc | 1140 |
| atttagttgg gcactctaag gtgactgccg gtgacaaacc ggaggaaggt ggggatgacg | 1200 |
| tcaaatcatc atgccccta tgacctgggc tacacacgtg ctacaatgga tggtacaaag | 1260 |
| ggctgcaaga ccgcgaggtc aagccaatcc cataaaacca ttctcagttc ggattgtagg | 1320 |
| ctgcaactcg cctacatgaa gctggaatcg ctagtaatcg cggatcagca tgccgcggtg | 1380 |
| aatacgttcc cgggccttgt acacaccgcc cgtcacacca cgagagtttg taacacccga | 1440 |
| agtcggtggg gtaaccttta tggagccagc cgcctaaggt gggacagatg attgggtga | 1500 |
| agtcgtaaca aggtagccgt atcggaaggt gcggctggat cacctccttt | 1550 |

<210> SEQ ID NO 7
<211> LENGTH: 1549
<212> TYPE: DNA
<213> ORGANISM: Bacillus licheniformis

<400> SEQUENCE: 7

| | |
|---|---|
| catggagagt ttgatcctgg ctcaggacga acgctggcgg cgtgcctaat acatgcaagt | 60 |
| cgagcggacc gacgggagct tgctccctta ggtcagcggc ggacgggtga gtaacacgtg | 120 |
| ggtaacctgc ctgtaagact gggataactc cgggaaaccg gggctaatac cggatgcttg | 180 |
| attgaaccgc atggttccaa tcataaaagg tggcttttag ctaccactta cagatggacc | 240 |
| cgcggcgcat tagctagttg gtgaggtaac ggctcaccaa ggcgacgatg cgtagccgac | 300 |
| ctgagagggt gatcggccac actgggactg agacacggcc cagactccta cgggaggcag | 360 |
| cagtagggaa tcttccgcaa tggacgaaag tctgacggag caacgccgcg tgagtgatga | 420 |
| aggttttcgg atcgtaaaac tctgttgtta gggaagaaca agtaccgttc gaatagggcg | 480 |
| gcacttgac ggtacctaac cagaaagcca cggctaacta cgtgccagca gccgcggtaa | 540 |
| tacgtaggtg gcaagcgttg tccggaatta ttgggcgtaa agcgcgcgca ggcggtttct | 600 |
| taagtctgat gtgaaagccc ccggctcaac cggggagggt cattggaaac tgggaactt | 660 |
| gagtgcagaa gaggagagtg gaattccacg tgtagcggtg aaatgcgtag agatgtggag | 720 |
| gaacaccagt ggcgaaggcg actctctggt ctgtaactga cgctgaggcg cgaaagcgtg | 780 |
| gggagcgaac aggattagat accctggtag tccacgccgt aaacgatgag tgctaagtgt | 840 |
| tagagggttt ccgcccttta gtgctgcagc aaacgcatta agcactccgc ctggggagta | 900 |
| cggtcgcaag actgaaactc aaaggaattg acggggccc gcacaagcgg tggagcatgt | 960 |
| ggtttaattc gaagcaacgc gaagaacctt accaggtctt gacatcctct gacaacccta | 1020 |
| gagatagggc ttccccttcg ggggcagagt gacaggtggt gcatggttgt cgtcagctcg | 1080 |

```
tgtcgtgaga tgttgggtta agtcccgcaa cgagcgcaac ccttgatctt agttgccagc   1140
attcagttgg gcactctaag gtgactgccg gtgacaaacc ggaggaaggt ggggatgacg   1200
tcaaatcatc atgcccctta tgacctgggc tacacacgtg ctacaatggg cagaacaaag   1260
ggcagcgaag ccgcgaggct aagccaatcc cacaaatctg ttctcagttc ggatcgcagt   1320
ctgcaactcg actgcgtgaa gctggaatcg ctagtaatcg cggatcagca tgccgcggtg   1380
aatacgttcc cgggccttgt acacaccgcc cgtcacacca cgagagtttg taacacccga   1440
agtcggtgag gtaaccttt ggagccagcc gccgaaggtg ggacagatga ttggggtgaa   1500
gtcgtaacaa ggtagccgta tcggaaggtg cggctggatc acctcctttt            1549

<210> SEQ ID NO 8
<211> LENGTH: 1549
<212> TYPE: DNA
<213> ORGANISM: Bacillus megaterium

<400> SEQUENCE: 8
tcggagagtt tgatcctggc tcaggatgaa cgctggcggc gtgcctaata catgcaagtc   60
gagcgaactg attagaagct tgcttctatg acgttagcgg cggacgggtg agtaacacgt   120
gggcaacctg cctgtaagac tgggataact tcgggaaacc gaagctaata ccggatagga   180
tcttctcctt catgggagat gattgaaaga tggtttcggc tatcacttac agatgggccc   240
gcggtgcatt agctagttgg tgaggtaacg gctcaccaag caacgatgc atagccgacc    300 tgagagggtg atcggccaca ctgggactga gacacggccc agactcctac gggaggcagc   360
agtagggaat cttccgcaat ggacgaaagt ctgacgagc aacgccgcgt gagtgatgaa    420
ggctttcggg tcgtaaaact ctgttgttag ggaagaacaa gtacgagagt aactgctcgt   480
accttgacgg tacctaacca gaaagccacg gctaactacg tgccagcagc cgcggtaata   540
cgtaggtggc aagcgttatc cggaattatt gggcgtaaag cgcgcgcagg cggtttctta   600
agtctgatgt gaaagcccac ggctcaaccg tggagggtca ttggaaactg ggaacttga    660 gtgcagaaga gaaaagcgga attccacgtg tagcggtgaa atgcgtagag atgtggagga   720
acaccagtgg cgaaggcggc ttttggtct gtaactgacg ctgaggcgcg aaagcgtggg    780
gagcaaacag gattagatac cctggtagtc cacgccgtaa acgatgagtg ctaagtgtta   840
gagggtttcc gccctttagt gctgcagcta acgcattaag cactccgcct ggggagtacg   900
gtcgcaagac tgaaactcaa aggaattgac ggggcccgc acaagcggtg gagcatgtgg    960
tttaattcga agcaacgcga agaaccttac caggtcttga catcctctga caactctaga   1020
gatagagcgt tccccttcgg gggacagagt gacaggtggt gcatggttgt cgtcagctcg   1080
tgtcgtgaga tgttgggtta agtcccgcaa cgagcgcaac ccttgatctt agttgccagc   1140
atttagttgg gcactctaag gtgactgccg gtgacaaacc ggaggaaggt ggggatgacg   1200
tcaaatcatc atgcccctta tgacctgggc tacacacgtg ctacaatgga tggtacaaag   1260
ggctgcaaga ccgcgaggtc aagccaatcc cataaaacca ttctcagttc ggattgtagg   1320
ctgcaactcg cctacatgaa gctggaatcg ctagtaatcg cggatcagca tgccgcggtg   1380
aatacgttcc cgggccttgt acacaccgcc cgtcacacca cgagagtttg taacacccga   1440
agtcggtgga gtaaccgtaa ggagctagcc gcctaaggtg ggacagatga ttggggtgaa   1500
gtcgtaacaa ggtagccgta tcggaaggtg cggctggatc acctcctttt            1549

<210> SEQ ID NO 9
```

```
<211> LENGTH: 1544
<212> TYPE: DNA
<213> ORGANISM: Bacillus pumilus

<400> SEQUENCE: 9
ggagagtttg atcctggctc aggacgaacg ctggcggcgt gcctaataca tgcaagtcga      60
gcggacagaa gggagcttgc tcccggatgt tagcggcgga cgggtgagta acacgtgggt     120
aacctgcctg taagactggg ataactccgg gaaaccggag ctaataccgg atagttcctt     180
gaaccgcatg gttcaaggat gaaagacggt ttcggctgtc acttacagat ggacccgcgg     240
cgcattagct agttggtggg gtaatggctc accaaggcga cgatgcgtag ccgacctgag     300
agggtgatcg gccacactgg gactgagaca cggcccagac tcctacggga gcagcagta     360
gggaatcttc cgcaatggac gaaagtctga cggagcaacg ccgcgtgagt gatgaaggtt     420
ttcggatcgt aaagctctgt tgttagggaa gaacaagtgc gagagtaact gctcgcacct     480
tgacggtacc taaccagaaa gccacggcta actacgtgcc agcagccgcg gtaatacgta     540
ggtggcaagc gttgtccgga attattgggc gtaaagggct cgcaggcggt ttcttaagtc     600
tgatgtgaaa gccccggct caaccgggga gggtcattgg aaactgggaa acttgagtgc     660
agaagaggag agtggaattc cacgtgtagc ggtgaaatgc gtagagatgt ggaggaacac     720
cagtggcgaa ggcgactctc tggtctgtaa ctgacgctga ggagcgaaag cgtggggagc     780
gaacaggatt agataccctg gtagtccacg ccgtaaacga tgagtgctaa gtgttagggg     840
gtttccgccc cttagtgctg cagctaacgc attaagcact ccgcctgggg agtacggtcg     900
caagactgaa actcaaagga attgacgggg cccgcacaa gcggtggagc atgtggttta     960
attcgaagca acgcgaagaa ccttaccagg tcttgacatc ctctgacaac cctagagata    1020
gggctttccc ttcggggaca gagtgacagg tggtgcatgg ttgtcgtcag ctcgtgtcgt    1080
gagatgttgg gttaagtccc gcaacgagcg caacccttga tcttagttgc cagcatttag    1140
ttgggcactc taaggtgact gccggtgaca aaccggagga aggtggggat gacgtcaaat    1200
catcatgccc cttatgacct gggctacaca cgtgctacaa tggacagaac aaagggctgc    1260
gagaccgcaa ggtttagcca atcccataaa tctgttctca gttcggatcg cagtctgcaa    1320
ctcgactgcg tgaagctgga atcgctagta atcgcggatc agcatgccgc ggtgaatacg    1380
ttcccgggcc ttgtacacac cgcccgtcac accacgagag tttgcaacac ccgaagtcgg    1440
tgaggtaacc tttatggagc cagccgccga aggtggggca gatgattggg gtgaagtcgt    1500
aacaaggtag ccgtatcgga aggtgcggct ggatcaccuc cttt                     1544

<210> SEQ ID NO 10
<211> LENGTH: 1549
<212> TYPE: DNA
<213> ORGANISM: Bacillus koreensis

<400> SEQUENCE: 10
tcggagagtt tgatcctggc tcaggacgaa cgctggcggc gtgcctaata catgcaagtc      60
gagcggactt gttagaagct tgcttctaac aagttagcgg cggacgggtg agtaacacgt     120
gggtaacctg cctgtaagat ggggataact ccgggaaacc ggagctaata ccgaataaca     180
ctttcgctcg catgagcgga tgttaaaaga cggtttcggc tgtcacttac agatggaccc     240
gcggcgcatt agctagttgg tgaggtaacg gctcaccaag gcgacgatgc gtagccgacc     300
tgagagggtg atcggccaca ctgggactga gacacggccc agactcctac gggaggcagc     360
agtagggaat cttccgcaat ggacgaaagt ctgacggagc aacgccgcgt gagtgatgaa     420
```

```
ggttttcgga tcgtaaaact ctgttgttag ggaagaacaa gtacgagagt aactgctcgt      480
accttgacgg tacctaacca gaaagccacg gctaactacg tgccagcagc cgcggtaata      540
cgtaggtggc aagcgttgtc cggaattatt gggcgtaaag cgcgcgcagg cggttcctta      600
agtctgatgt gaaagcccac ggctcaaccg tggagggtca ttggaaactg gggaacttga      660
gtgcagaaga ggaaagcgga attccacgtg tagcggtgaa atgcgtagag atgtggagga      720
acaccagtgg cgaaggcggc tttctggtct gtaactgacg ctgaggcgcg aaagcgtggg      780
gagcaaacag gattagatac cctggtagtc cacgccgtaa acgatgagtg ctaagtgtta      840
gagggtttcc gccctttagt gctgcagcta acgcattaag cactccgcct ggggagtacg      900
gccgcaaggc tgaaactcaa aggaattgac ggggcccgc acaagcggtg gagcatgtgg        960
tttaattcga agcaacgcga agaaccttac caggtcttga catcctttga ccactctaga     1020
gatagagctt tccccttcgg gggacaaagt gacaggtggt gcatggttgt cgtcagctcg     1080
tgtcgtgaga tgttgggtta agtcccgcaa cgagcgcaac ccttgatctt agttgccagc     1140
attaagttgg gcactctaag gtgactgccg gtgacaaacc ggaggaaggt ggggatgacg     1200
tcaaatcatc atgcccctta tgacctgggc tacacacgtg ctacaatgga tgatacaaag     1260
ggttgcgaag ccgcgaggtg aagctaatct cataaaatca ttctcagttc ggattgtagg     1320
ctgcaactcg cctacatgaa gctggaatcg ctagtaatcg cggatcagca tgccgcggtg     1380
aatacgttcc cgggccttgt acacaccgcc cgtcacacca cgagagtttg taacacccga     1440
agtcggtggg gtaaccgtaa ggagccagcc gcctaaggtg gacagatga ttggggtgaa      1500 gtcgtaacaa ggtagccgta tcggaaggtg cggctggatc acctcctttt                1549
```

<210> SEQ ID NO 11
<211> LENGTH: 1454
<212> TYPE: DNA
<213> ORGANISM: Bacillus drentensis

<400> SEQUENCE: 11

```
cttggagagt ttgatcctgg ctcaggacga acgctggcgg cgtgcctaat acatgcaagt       60
cgagcgaatc ttcaggagct tgctcctgtt ggttagcggc ggacgggtga gtaacacgtg      120
ggcaacctgc ctgtaagact gggataacac cgggaaaccg gtgctaatac cggataatcc      180
ttttcctctc atgaggaaaa gctgaaagtc ggtttcggct gacacttaca gatgggcccg      240
cggcgcatta gctagttggt gaggtaacgg ctcaccaagg cgacgatgcg tagccgacct      300
gagagggtga tcggccacac tgggactgag acacggccca gactcctacg ggaggcagca      360
gtagggaatc ttccacaatg gacgaaagtc tgatggagca acgccgcgtg agcgatgaag      420
gccttcgggt cgtaaagctc tgttgttagg gaagaacaag taccgagta actgccggta      480 ccttgacggt acctaaccag aaagccacgg ctaactacgt gccagcagcc gcggtaatac      540
gtaggtggca agcgttgtcc ggaattattg gcgtaaagc gcgcgcaggc ggtcctttaa      600
gtctgatgtg aaagcccacg gctcaaccgt ggagggtcat tggaaactgg ggacttgag      660 tgcagaagag gaaagcggaa ttccacgtgt agcggtgaaa tgcgtagaga tgtggaggaa      720
caccagtggc gaaggcggct ttctggtctg taactgacgc tgaggcgcga aagcgtgggg      780
agcaaacagg attagatacc ctggtagtcc acgccgtaaa cgatgagtgc taagtgttag      840
ggggtttccg cccttagtg ctgcagctaa cgcattaagc actccgcctg gggagtacgg      900
ccgcaaggct gaaactcaaa ggaattgacg ggcccgca caagcggtgg agcatgtggt       960
```

-continued

```
ttaattcgaa gcaacgcgaa gaaccttacc aggtcttgac atcctctgac actcctagag   1020
ataggacgtt ccccttcggg ggacagagtg acaggtggtg catggttgtc gtcagctcgt   1080
gtcgtgagat gttgggttaa gtcccgcaac gagcgcaacc cttgatctta gttgccagca   1140
ttcagttggg cactctaagg tgactgccgg tgacaaaccg gaggaaggtg gggatgacgt   1200
caaatcatca tgccccttat gacctgggct acacacgtgc tacaatggat ggtacaaagg   1260
gctgcaagac cgcgaggttt agccaatccc ataaaaccat tctcagttcg gattgcaggc   1320
tgcaactcgc ctgcatgaag ccggaatcgc tagtaatcgc ggatcagcat gccgcggtga   1380
atacgttccc gggccttgta cacaccgccc gtcacaccac gagagtttgt aacacccgaa   1440
gtcggtgggg taac                                                     1454

<210> SEQ ID NO 12
<211> LENGTH: 1454
<212> TYPE: DNA
<213> ORGANISM: Bacillus subtilis

<400> SEQUENCE: 12
cttggagagt ttgatcctgg ctcaggacga acgctggcgg cgtgcctaat acatgcaagt     60
cgagcgaatc ttcaggagct tgctcctgtt ggttagcggc ggacgggtga gtaacacgtg    120
ggcaacctgc ctgtaagact gggataacac cgggaaaccg gtgctaatac cggataatcc    180
ttttcctctc atgaggaaaa gctgaaagtc ggtttcggct gacacttaca gatgggcccg    240
cggcgcatta gctagttggt gaggtaacgg ctcaccaagg cgacgatgcg tagccgacct    300
gagagggtga tcggccacac tgggactgag acacggccca gactcctacg ggaggcagca    360
gtagggaatc ttccacaatg gacgaaagtc tgatggagca acgccgcgtg agcgatgaag    420
gccttcgggt cgtaaagctc tgttgttagg gaagaacaag taccggagta actgccggta    480
ccttgacggt acctaaccag aaagccacgg ctaactacgt gccagcagcc gcggtaatac    540
gtaggtggca agcgttgtcc ggaattattg ggcgtaaagc gcgcgcaggc ggtcctttaa    600
gtctgatgtg aaagcccacg gctcaaccgt ggagggtcat tggaaactgg gggacttgag    660
tgcagaagag gaaagcggaa ttccacgtgt agcggtgaaa tgcgtagaga tgtggaggaa    720
caccagtggc gaaggcggct ttctggtctg taactgacgc tgaggcgcga aagcgtgggg    780
agcaaacagg attagatacc ctggtagtcc acgccgtaaa cgatgagtgc taagtgttag    840
ggggtttccg ccccttagtg ctgcagctaa cgcattaagc actccgcctg gggagtacgg    900
ccgcaaggct gaaactcaaa ggaattgacg ggggcccgca caagcggtgg agcatgtggt    960
ttaattcgaa gcaacgcgaa gaaccttacc aggtcttgac atcctctgac actcctagag   1020
ataggacgtt ccccttcggg ggacagagtg acaggtggtg catggttgtc gtcagctcgt   1080
gtcgtgagat gttgggttaa gtcccgcaac gagcgcaacc cttgatctta gttgccagca   1140
ttcagttggg cactctaagg tgactgccgg tgacaaaccg gaggaaggtg gggatgacgt   1200
caaatcatca tgccccttat gacctgggct acacacgtgc tacaatggat ggtacaaagg   1260
gctgcaagac cgcgaggttt agccaatccc ataaaaccat tctcagttcg gattgcaggc   1320
tgcaactcgc ctgcatgaag ccggaatcgc tagtaatcgc ggatcagcat gccgcggtga   1380
atacgttccc gggccttgta cacaccgccc gtcacaccac gagagtttgt aacacccgaa   1440
gtcggtgggg taac                                                     1454

<210> SEQ ID NO 13
<211> LENGTH: 1320
```

-continued

<212> TYPE: DNA
<213> ORGANISM: Clostridium bifermentans

<400> SEQUENCE: 13
gcttttgtat caaagctccg gcggtacagg atggacccgc gtctgattag ctagttggta 60
aggtaatggc ttaccaaggc aacgatcagt agccgacctg agagggtgat cggccacact 120
ggaactgaga cacggtccag actcctacgg gaggcagcag tggggaatat tgcacaatgg 180
gcgaaagcct gatgcagcaa cgccgcgtga gcgatgaagg ccttcgggtc gtaaagctct 240
gtcctcaagg aagataatga cggtacttga ggaggaagcc ccggctaact acgtgccagc 300
agccgcggta atacgtaggg ggctagcgtt atccggaatt actgggcgta aagggtgcgt 360
aggtggtttt ttaagtcaga agtgaaaggc tacggctcaa ccgtagtaag cttttgaaac 420
tagagaactt gagtgcagga gaggagagta gaattcctag tgtagcggtg aaatgcgtag 480
atattaggag gaataccagt agcgaaggcg gctctctgga ctgtaactga cactgaggca 540
cgaaagcgtg gggagcaaac aggattagat accctggtag tccacgccgt aaacgatgag 600
tactaggtgt cggggggttac ccccctcggt gccgcagcta acgcattaag tactccgcct 660
gggaagtacg ctcgcaagag tgaaactcaa aggaattgac ggggacccgc acaagtagcg 720
gagcatgtgg tttaattcga agcaacgcga agaaccttac ctaagcttga catcccactg 780
acctctccct aatcggagat ttcccttcgg ggacagtggt gacaggtggt gcatggttgt 840
cgtcagctcg tgtcgtgaga tgttgggtta agtcccgcaa cgagcgcaac ccttgccttt 900
agttgccagc attaagttgg gcactctaga gggactgccg aggataactc ggaggaaggt 960
ggggatgacg tcaaatcatc atgcccctta tgcttagggc tacacacgtg ctacaatggg 1020
tggtacagag ggttgccaag ccgcgaggtg gagctaatcc cttaaagcca ttctcagttc 1080
ggattgtagg ctgaaactcg cctacatgaa gctggagtta ctagtaatcg cagatcagaa 1140
tgctgcggtg aatgcgttcc cgggtcttgt acacaccgcc cgtcacacca tggaagttgg 1200
gggcgcccga agccggttag ctaacctttt aggaagcggc cgtcgaaggt gaaaccaatg 1260
actggggtga agtcgtaaca aggtagccgt atcggaaggt gcggctggat cacctccttt 1320

<210> SEQ ID NO 14
<211> LENGTH: 1510
<212> TYPE: DNA
<213> ORGANISM: Clostridium beijerinckii

<400> SEQUENCE: 14
tattgagagt ttgatcctgg ctcaggacga acgctggcgg cgtgcttaac acatgcaagt 60
cgagcgatga agttccttcg ggaatggatt agcggcggac gggtgagtaa cacgtgggta 120
acctgcctca tagaggggaa tagcctttcg aaaggaagat taataccgca taagattgta 180
gtgccgcatg gcatagcaat taaaggagta atccgctatg agatggaccc gcgtcgcatt 240
agctagttgg tgaggtaacg gctcaccaag gcgacgatgc gtagccgacc tgagagggtg 300
atcggccaca ttgggactga gacacggccc agactcctac gggaggcagc agtggggaat 360
attgcacaat gggggaaacc ctgatgcagc aacgccgcgt gagtgatgac ggtcttcgga 420
ttgtaaagct ctgtcttcag ggacgataat gacggtacct gaggaggaag ccacggctaa 480
ctacgtgcca gcagccgcgg taatacgtag gtggcaagcg ttgtccggat ttactgggcg 540
taaagggagc gtaggtggat atttaagtgg gatgtgaaat actcgggctt aacctgggtg 600
ctgcattcca aactggatat ctagagtgca ggagaggaaa gtagaattcc tagtgtagcg 660

```
gtgaaatgcg tagagattag aagaatacc  agtggcgaag gcgactttct ggactgtaac    720
tgacactgag gctcgaaagc gtggggagca aacaggatta gataccctgg tagtccacgc    780
cgtaaacgat gaatactagg tgtaggggtt gtcatgacct ctgtgccgcc gctaacgcat    840
taagtattcc gcctggggag tacggtcgca agattaaaac tcaaaggaat tgacggggc     900
ccgcacaagc agcggagcat gtggtttaat tcgaagcaac gcgaagaacc ttacctagac    960
ttgcacatctc ctgaattacc cttaatcggg gaagcccttc ggggcaggaa gacaggtggt   1020
gcatggttgt cgtcagctcg tgtcgtgaga tgttgggtta agtcccgcaa cgagcgcaac   1080
ccttattgtt agttgctacc atttagttga gcactctagc gagactgccc gggttaaccg   1140
ggaggaaggt ggggatgacg tcaaatcatc atgcccctta tgtctagggc tacacacgtg   1200
ctacaatggc tggtacagag agatgctaaa ccgtgaggtg gagccaaact ttaaaaccag   1260
tctcagttcg gattgtaggc tgaaactcgc ctacatgaag ctggagttgc tagtaatcgc   1320
gaatcagaat gtcgcggtga atacgttccc gggccttgta caccgcccc  gtcacaccat   1380
gagagttggc aatacccaaa gttcgtgagc taacgcgcaa gcggggcagc gacctaaggt   1440
agggtcagcg attggggtga agtcgtaaca aggtagccgt aggagaacct gcggctggat   1500
cacctccttt                                                          1510

<210> SEQ ID NO 15
<211> LENGTH: 1505
<212> TYPE: DNA
<213> ORGANISM: Clostridium pasteurianum

<400> SEQUENCE: 15
aattgagagt ttgatcctgg ctcaggacga acgctggcgg cgtgcttaac acatgcaagt    60
cgagcgagaa accttcgggt ttctagcggc ggacgggtga gtaacacgtg gtaacctgc   120
ctcaaagagg ggaatagcct cccgaaaggg agattaatac cgcataatat tacagcttcg   180
catgaagcag taattaaagg agtaatccgc tttgagatgg acccgcggcg cattagctag   240
ttggagaggt aacggctcac caaggcgacg atgcgtagcc gacctgagag ggtgatcggc   300
cacattggaa ctgagacacg gtccagactc ctacgggagg cagcagtggg gaatattgca   360
caatgggcga aagcctgatg cagcaacgcc gcgtgagtga tgacggtctt cggattgtaa   420
agctctgtct tttgggacga taatgacggt accaaaggag gaagccacgg ctaactacgt   480
gccagcagcc gcggtaatac gtaggtggca agcgttgtcc ggatttactg ggcgtaaagg   540
atgtgtaggc ggatacttaa gtgagatgtg aaagccccgg gcttaacttg gggactgcat   600
ttcaaactgg gtgtctagag tgcaggagag gaaagcggaa ttcctagtgt agcggtgaaa   660
tgcgtagaga ttaggaagaa catcagtggc gaaggcggct ttctggactg taactgacgc   720
tgaggcatga aagcgtgggg agcaaacagg attagatacc ctggtagtcc acgccgtaaa   780
cgatgagtac taggtgtagg aggtatcgac tccttctgtg ccgcagtaaa cacaataagt   840
actccgcctg ggaagtacgg tcgcaagatt aaaactcaaa ggaattgacg ggggcccgca   900
caagcagcgg agcatgtggt ttaattcgaa gcaacgcgaa gaaccttacc tagacttgac   960
atctcctgaa tagcgtagag atacgtgaag cccttcgggg caggaagaca ggtggtgcat  1020
ggttgtcgtc agctcgtgtc gtgagatgtt gggttaagtc ccgcaacgag cgcaaccctt  1080
atcattagtt gctaccatta agttgagcac tctagtgaga ctgcccgggt taaccgggag  1140
gaaggcgggg atgacgtcaa atcatcatgc cccttatgtc tagggctaca cacgtgctac  1200
aatggtgaga acaacgagat gcaataccgc gaggtggagc caaacttgaa aactcatccc  1260
```

-continued

```
agttcggatt gtaggctgaa attcgcctac atgaagttgg agttgctagt aatcgcgaat    1320
cagaatgtcg cggtgaatac gttcccgggc cttgtacaca ccgcccgtca caccatgaga    1380
gctggtaaca cccgaagtcc gtgaggtaac ctttatggag ccagcggccg aaggtgggat    1440
tagtgattgg ggtgaagtcg taacaaggta gccgtaggag aacctgcggc tggatcacct    1500
ccttt                                                                 1505
```

<210> SEQ ID NO 16
<211> LENGTH: 1567
<212> TYPE: DNA
<213> ORGANISM: Lactobacillus paracasei

<400> SEQUENCE: 16

```
tatgagagtt tgatcctggc tcaggatgaa cgctggcggc gtgcctaata catgcaagtc      60
gaacgagttc tcgttgatga tcggtgcttg caccgagatt caacatggaa cgagtggcgg     120
acgggtgagt aacacgtggg taacctgccc ttaagtgggg ataacatttt ggaaacagat     180
gctaataccg catagatcca agaaccgcat ggttcttggc tgaaagatgg cgtaagctat     240
cgcttttgga tggacccgcg gcgtattagc tagttggtga ggtaacggct caccaaggcg     300
atgatacgta gccgaactga gaggttgatc ggccacattg ggactgagac acggcccaaa     360
ctcctacggg aggcagcagt agggaatctt ccacaatgga cgcaagtctg atggagcaac     420
gccgcgtgag tgaagaaggc tttcgggtcg taaaactctg ttgttggaga agaatggtcg     480
gcagagtaac tgttgtcggc gtgacggtat ccaaccagaa agccacggct aactacgtgc     540
cagcagccgc ggtaatacgt aggtggcaag cgttatccgg atttattggg cgtaaagcga     600
gcgcaggcgg tttttttaagt ctgatgtgaa agccctcggc ttaaccgagg aagcgcatcg     660
gaaactggga aacttgagtg cagaagagga cagtggaact ccatgtgtag cggtgaaatg     720
cgtagatata tggaagaaca ccagtggcga aggcggctgt ctggtctgta actgacgctg     780
aggctcgaaa gcatgggtag cgaacaggat tagataccct ggtagtccat gccgtaaacg     840
atgaatgcta ggtgttggag ggtttccgcc cttcagtgcc gcagctaacg cattaagcat     900
tccgcctggg gagtacgacc gcaaggttga aactcaaagg aattgacggg ggcccgcaca     960
agcggtggag catgtggttt aattcgaagc aacgcgaaga accttaccag gtcttgacat    1020
cttttgatca cctgagagat caggtttccc cttcgggggc aaaatgacag gtggtgcatg    1080
gttgtcgtca gctcgtgtcg tgagatgttg ggttaagtcc cgcaacgagc gcaaccctta    1140
tgactagttg ccagcattta gttgggcact ctagtaagac tgccggtgac aaaccggagg    1200
aaggtgggga tgacgtcaaa tcatcatgcc ccttatgacc tgggctacac acgtgctaca    1260
atggatggta caacgagttg cgagaccgcg aggtcaagct aatctcttaa agccattctc    1320
agttcggact gtaggctgca actcgcctac acgaagtcgg aatcgctagt aatcgcggat    1380
cagcacgccg cggtgaatac gttcccgggc cttgtacaca ccgcccgtca caccatgaga    1440
gtttgtaaca cccgaagccg gtggcgtaac ccttttaggg agcgagccgt ctaaggtggg    1500
acaaatgatt agggtgaagt cgtaacaagg tagccgtagg agaacctgcg gctggatcac    1560
ctcctttt                                                              1567
```

<210> SEQ ID NO 17
<211> LENGTH: 512
<212> TYPE: DNA
<213> ORGANISM: Fontibacillus sp. (panacisegetis)

```
<400> SEQUENCE: 17
ttagcggcgg acgggtgagt aacacgtagg taacctgcct gtaagactgg gataactagc      60
ggaaacgtta gctaataccg gataatttat tttctcgcat ggggaagtaa tgaaagacgg     120
agcaatctgt cacttgcaga tggacctgcg gcgcattagc tagttggtgg ggtaacggct     180
caccaaggcg acgatgcgta gccgacctga gagggtgaac ggccacactg ggactgagac     240
acggcccaga ctcctacggg aggcagcagt agggaatctt ccgcaatgga cgaaagtctg     300
acggagcaac gccgcgtgag tgatgaaggt tttcggatcg taaagctctg ttgccaggga     360
agaacgttcg gtagagtaac tgctaccgga gtgacggtac ctgagaagaa gccccggct      420 aactacgtgc cagcagccgc ggtaatacgt aggggggcaag cgttgtccgg aattattggg     480
cgtaaagcgc gcgcaggcgg ctatttaagt ct                                   512

<210> SEQ ID NO 18
<211> LENGTH: 1561
<212> TYPE: DNA
<213> ORGANISM: Oceanobacillus oncorhynchi

<400> SEQUENCE: 18
ttatggagag tttgatcttg gctcaggacg aacgctggcg gcgtgcctaa tacatgcaag      60
tcgagcgcgg gaagcgaacg gaactcttcg gagggaagtt cgtggaacga gcggcggacg     120
ggtgagtaac acgtaggcaa cctgcctgta agactgggat aactcgcgga aacgcgagct     180
aataccggat aacactttct atcacctgat ggaaagttga aggcggcttt tgctgtcac      240 ttacagatgg gcctgcggcg cattagctag ttggtgaggt aacggctcac caaggcgacg     300
atgcgtagcc gacctgagag ggtgatcggc cacactggga ctgagacacg gcccagactc     360
ctacgggagg cagcagtagg gaatcttccg caatggacga agtctgacg gagcaacgcc     420 gcgtgagtga tgaaggtttt cggatcgtaa aactctgttg tcaggaaga acaagtacga     480 tagtaactga tcgtaccttg acggtacctg accagaaagc cacggctaac tacgtgccag     540
cagccgcggt aatacgtagg tggcaagcgt tgtccggaat tattgggcgt aaagcgctcg     600
caggcggttc tttaagtctg atgtgaaatc ttgcggctca accgcaaacg tgcattggaa     660
actggaggac ttgagtgcag aagaggagag tggaattcca cgtgtagcgg tgaaatgcgt     720
agagatgtgg aggaacacca gtggcgaagg cgactctctg gtctgtaact gacgctgagg     780
agcgaaagcg tggggagcga acaggattag ataccctggt agtccacgcc gtaaacgatg     840
agtgctaggt gttaggggggt ttccgccccct tagtgctgaa gttaacgcat taagcactcc     900
gcctggggag tacggccgca aggctgaaac tcaaaagaat tgacgggac ccgcacaagc     960 ggtggagcat gtggtttaat tcgaagcaac gcgaagaacc ttaccaggtc ttgacatcct    1020
ttgaccgctc tagagataga gttttccctt cggggacaaa gtgacaggtg gtgcatggtt    1080
gtcgtcagct cgtgtcgtga gatgttgggt taagtcccgc aacgagcgca accettaatc    1140 ttagttgcca gcatttagtt gggcactcta aggtgactgc cggtgacaaa ccggaggaag    1200 gtgggatga cgtcaaatca tcatgccccct tatgacctgg gctacacacg tgctacaatg    1260
gacggaacaa agggaagcga acccgcgagg tccagcaaat cccataaaac cgttctcagt    1320
tcggattgca ggctgcaact cgcctgcatg aagccggaat cgctagtaat cgcggatcag    1380
catgccgcgg tgaatacgtt cccgggtctt gtacacaccg cccgtcacac cacgagagtt    1440
cgtaacaccc gaagtcggtg aggtaacctt ttggagccag ccgccgaagg tgggacgaat    1500
gattggggtg aagtcgtaac aaggtagccg tatcggaagg tgcggctgga tcacctcctt    1560
```

| | |
|---|---|
| t | 1561 |

<210> SEQ ID NO 19
<211> LENGTH: 1553
<212> TYPE: DNA
<213> ORGANISM: Paenibacillus lautus

<400> SEQUENCE: 19

| | | | | | | |
|---|---|---|---|---|---|---|
| attggagagt | ttgatcctgg | ctcaggacga | acgctggcgg | cgtgcctaat | acatgcaagt | 60 |
| cgagcggact | tgatggagtg | cttgcactcc | tgaaggttag | cggcggacgg | gtgagtaaca | 120 |
| cgtaggcaac | ctgccctcaa | gactgggata | actaccggaa | acggtagcta | ataccggata | 180 |
| atttattttg | cagcattgtg | aaataatgaa | aggcggagca | atctgtcact | tgaggatggg | 240 |
| cctgcggcgc | attagctagt | tggtgggta | acggcccacc | aaggcgacga | tgcgtagccg | 300 |
| acctgagagg | gtgaacggcc | acactgggac | tgagacacgg | cccagactcc | tacgggaggc | 360 |
| agcagtaggg | aatcttccgc | aatgggcgaa | agcctgacgg | agcaacgccg | cgtgagtgat | 420 |
| gaaggttttc | ggatcgtaaa | gctctgttgc | caaggaagaa | cgtcttctag | agtaactgct | 480 |
| aggagagtga | cggtacttga | gaagaaagcc | ccggctaact | acgtgccagc | agccgcggta | 540 |
| atacgtaggg | ggcaagcgtt | gtccggaatt | attgggcgta | aagcgcgcgc | aggcggttct | 600 |
| ttaagtctgg | tgtttaaacc | cgaggctcaa | cttcgggtcg | cactgaaac | tggggaactt | 660 |
| gagtgcagaa | gaggagagtg | gaattccacg | tgtagcggtg | aaatgcgtag | atatgtggag | 720 |
| gaacaccagt | ggcgaaggcg | actctctggg | ctgtaactga | cgctgaggcg | cgaaagcgtg | 780 |
| gggagcaaac | aggattagat | accctggtag | tccacgccgt | aaacgatgaa | tgctaggtgt | 840 |
| taggggtttc | gataccttg | gtgccgaagt | taacacatta | agcattccgc | ctggggagta | 900 |
| cggtcgcaag | actgaaactc | aaaggaattg | acggggaccc | gcacaagcag | tggagtatgt | 960 |
| ggtttaattc | gaagcaacgc | gaagaacctt | accaagtctt | gacatccctc | tgaatcctct | 1020 |
| agagatagag | gcggccttcg | ggacagaggt | gacaggtggt | gcatggttgt | cgtcagctcg | 1080 |
| tgtcgtgaga | tgttgggtta | agtcccgcaa | cgagcgcaac | ccttgatttt | agttgccagc | 1140 |
| acttcgggtg | ggcactctag | aatgactgcc | ggtgacaaac | cggaggaagg | cggggatgac | 1200 |
| gtcaaatcat | catgcccctt | atgacttggg | ctacacacgt | actacaatgg | ctggtacaac | 1260 |
| gggaagcgaa | gccgcgaggt | ggagccaatc | ctataaaagc | cagtctcagt | tcggattgca | 1320 |
| ggctgcaact | cgcctgcatg | aagtcggaat | tgctagtaat | cgcggatcag | catgccgcgg | 1380 |
| tgaatacgtt | cccgggtctt | gtacacaccg | cccgtcacac | cacgagagtt | tacaacaccc | 1440 |
| gaagtcggtg | gggtaaccct | taggggagcc | agccgccgaa | ggtggggtag | atgattgggg | 1500 |
| tgaagtcgta | acaaggtagc | cgtatcggaa | ggtgcggctg | gatcacctcc | ttt | 1553 |

<210> SEQ ID NO 20
<211> LENGTH: 1553
<212> TYPE: DNA
<213> ORGANISM: Paenibacillus chibensis

<400> SEQUENCE: 20

| | | | | | | |
|---|---|---|---|---|---|---|
| cttggagagt | ttgatcctgg | ctcaggacga | acgctggcgg | cgtgcctaat | acatgcaagt | 60 |
| cgagcggagt | tgatgaggtg | cttgcacctc | tgatgcttag | cggcggacgg | gtgagtaaca | 120 |
| cgtaggtaac | ctgcctgtaa | gactgggata | actaccggaa | acggtagcta | ataccggata | 180 |
| atttattttc | tctcctgggg | agataatgaa | agacggagca | atctgtcact | tacagatggg | 240 |

```
cctgcggcgc attagctagt tggtgaggta acggctcacc aaggcgacga tgcgtagccg    300
acctgagagg gtgaacggcc acactgggac tgagacacgg cccagactcc tacgggaggc    360
agcagtaggg aatcttccgc aatggacgaa agtctgacgg agcaacgccg cgtgagtgat    420
gaaggttttc ggatcgtaaa gctctgttgc cagggaagaa cgtccggtag agtaactgct    480
accggagtga cggtacctga gaagaaagcc ccggctaact acgtgccagc agccgcggta    540
atacgtaggg ggcaagcgtt gtccggaatt attgggcgta aagcgcgcgc aggcggtcac    600
ttaagtctgg tgtttaaggc caaggctcaa ccttggttcg cactggaaac tgggtgactt    660
gagtgcagaa gaggagagtg gaattccacg tgtagcggtg aaatgcgtag atatgtggag    720
gaacaccagt ggcgaaggcg actctctggg ctgtaactga cgctgaggcg cgaaagcgtg    780
gggagcaaac aggattagat accctggtag tccacgccgt aaacgatgaa tgctaggtgt    840
tagggttttc gatacccttg gtgccgaagt taacacatta agcattccgc ctggggagta    900
cggtcgcaag actgaaactc aaaggaattg acggggaccc gcacaagcag tggagtatgt    960
ggtttaattc gaagcaacgc gaagaacctt accaagtctt gacatccctc tgaatcctct   1020
agagatagag gcggccttcg ggacagaggt gacaggtggt gcatggttgt cgtcagctcg   1080
tgtcgtgaga tgttgggtta agtcccgcaa cgagcgcaac ccttgatttt agttgccagc   1140
atttcggatg ggcactctag aatgactgcc ggtgacaaac cggaggaagg cggggatgac   1200
gtcaaatcat catgccccctt atgacttggg ctacacacgt actacaatgg ccagtacaac   1260
gggaagcgaa atcgcgagat ggagccaatc ctatcaaagc tggtctcagt tcggattgca   1320
ggctgcaacc cgcctgcatg aagtcggaat tgctagtaat cgcggatcag catgccgcgg   1380
tgaatacgtt cccgggtctt gtacacaccg cccgtcacac cacgagagtt tacaacaccc   1440
gaagtcggtg gggtaacccg caaggagcc agccgccgaa ggtggggtag atgattgggg    1500
tgaagtcgta acaaggtagc cgtatcggaa ggtgcggctg gatcacctcc ttt          1553
```

<210> SEQ ID NO 21
<211> LENGTH: 1552
<212> TYPE: DNA
<213> ORGANISM: Paenibacillus cookii

<400> SEQUENCE: 21

```
cttggagagt ttgatcctgg ctcaggacga acgctggcgg cgtgcctaat acatgcaagt     60
cgagcggagt tgatggggag cttgctctcc tgagacttag cggcggacgg gtgagtaaca    120
cgtaggcaac ctgcccgtaa gaccgggata actaccggaa acgqtagcta ataccggata    180 atttatcgct tcgcatggag cggtaatgaa agacggagca atctgtcact tacggatggg    240
cctgcggcgc attagctagt tggtgaggta acggctcacc aaggcgacga tgcgtagccg    300
acctgagagg gtgaacggcc acactgggac tgagacacgg cccagactcc tacgggaggc    360
agcagtaggg aatcttccgc aatgggcgaa agcctgacgg agcaacgccg cgtgagtgat    420
gaaggttttc ggatcgtaaa gctctgttgc cagggaagaa cgtcgggtag agtaactgct    480
atccgagtga cggtacctga gaagaaagcc ccggctaact acgtgccagc agccgcggta    540
atacgtaggg ggcaagcgtt gtccggaatt attgggcgta aagcgcgcgc aggcggtcac    600
ttaagtctgg tgtttaaggc tagggctcaa ctctagttcg cactggaaac tgggtgactt    660
gagtgcagaa gaggaaagtg gaattccacg tgtagcggtg aaatgcgtag atatgtggag    720
gaacaccagt ggcgaaggcg actttctggg ctgtaactga cgctgaggcg cgaaagcgtg    780
gggagcaaac aggattagat accctggtag tccacgccgt aaacgatgaa tgctaggtgt    840
```

```
tagggggtttc gatacccttg gtgccgaagt taacacatta agcattccgc ctggggagta      900
cggtcgcaag actgaaactc aaaggaattg acggggaccc gcacaagcag tggagtatgt      960
ggtttaattc gaagcaacgc gaagaacctt accaggtctt gacatccctc tgaatcctct     1020
agagatagag gcggccttcg ggacagagga gacaggtggt gcatggttgt cgtcagctcg     1080
tgtcgtgaga tgttgggtta agtcccgcaa cgagcgcaac ccttgatttt agttgccagc     1140
acattaaggt gggcactcta gaatgactgc cggtgacaaa ccggaggaag gcggggatga     1200
cgtcaaatca tcatgcccct tatgacctgg gctacacacg tactacaatg gccagtacaa     1260
cgggaagcga agtcgcgaga cggagccaat cctatcaaag ctggtctcag ttcggattgc     1320
aggctgcaac ccgcctgcat gaagtcggaa ttgctagtaa tcgcggatca gcatgccgcg     1380
gtgaatacgt tcccgggtct tgtacacacc gcccgtcaca ccacgagagt ttacaacacc     1440
cgaagtcggt ggggtaaccg caaggagcca gccgccgaag gtggggtaga tgattggggt     1500
gaagtcgtaa caaggtagcc gtatcggaag gtgcggctgg atcacctcct tt             1552
```

<210> SEQ ID NO 22
<211> LENGTH: 1330
<212> TYPE: DNA
<213> ORGANISM: Paenibacillus sp. (chitinolyticus)

<400> SEQUENCE: 22

```
ctgtggctta cggatgggcc tgcggcgcat tagctagttg gtgaggtaac ggctcaccaa       60
ggcgacgatg cgtagccgac ctgagagggt gaacggccac actgggactg agacacggcc      120
cagactccta cgggaggcag cagtagggaa tcttccgcaa tggacgcaag tctgacggag      180
caacgccgcg tgagtgatga aggttttcgg atcgtaaagc tctgttgcca gggaagaacg      240
ccaaggagag taactgctct ttgggtgacg gtacctgaga gaaagccccc ggctaactac      300
gtgccagcag ccgcggtaat acgtaggggg caagcgttgt ccggaattat tgggcgtaaa      360
gcgcgcgcag gcggtttttt aagtctggtg tttaatcccg aggctcaacc tcggttcgca      420
ccggaaactg ggagactgga gtgcaggaga ggaaagtgga attccacgtg tagcggtgaa      480
atgcgtagag atgtggagga acaccagtgg cgaaggcgac tttctggcct gtaactgacg      540
ctgaggcgcg aaagcgtggg gagcaaaacag gattagatac cctggtagtc cacgccgtaa      600
acgatgaatg ctaggtgtta gggtttcga tacccttggt gccgaagtta acacagtaag      660
cattccgcct ggggagtacg ctcgcaagag tgaaactcaa aggaattgac ggggacccgc      720
acaagcagtg gagtatgtgg tttaattcga agcaacgcga gaaccttac caggtcttga      780 catccctctg accggcttag agataagcct ttccttcggg acagaggtga caggtggtgc      840
atggttgtcg tcagctcgtg tcgtgagatg ttgggttaag tcccgcaacg agcgcaaccc      900
ttgaacttag ttgccagcag gtaaagctgg gcactctaag ttgactgccg gtgacaaacc      960
ggaggaaggc ggggatgacg tcaaatcatc atgcccctta tgacctgggc tacacacgta     1020
ctacaatggc cggtacaacg ggaagcgaag gagcgatccg gagccaatcc tagaaaagcc     1080
ggtctcagtt cggattgcag gctgcaactc gcctgcatga agtcggaatt gctagtaatc     1140
gcggatcagc atgccgcggt gaatacgttc ccggtcttg tacacaccgc ccgtcacacc     1200
acgagagttt acaacacccg aagtcggtga gtaaccgca aggagccagc cgccgaaggt     1260
ggggtagatg attggggtga agtcgtaaca aggtagccgt atcggaaggt gcggctggat     1320
cacctccttt                                                            1330
```

<210> SEQ ID NO 23
<211> LENGTH: 866
<212> TYPE: DNA
<213> ORGANISM: Paenibacillus sp. (P1PXP2)

<400> SEQUENCE: 23

| | | | | | |
|---|---|---|---|---|---|
| cagagggatg | tcaagacctg | gtaaggttct | tcgcgttgct | tcgaattaaa | ccacatactc | 60 |
| cactgcttgt | gcgggtcccc | gtcaattcct | ttgagtttca | gtcttgcgac | cgtactcccc | 120 |
| aggcggaatg | cttaatgtgt | taacttcggc | accaagggta | tcgaaacccc | taacacctag | 180 |
| cattcatcgt | ttacggcgtg | gactaccagg | gtatctaatc | ctgtttgctc | cccacgcttt | 240 |
| cgcgcctcag | cgtcagttac | agcccagaga | gtcgccttcg | ccactggtgt | tcctccacat | 300 |
| atctacgcat | ttcaccgcta | cacgtggaat | tccactctcc | tcttctgcac | tcaagtcacc | 360 |
| cagtttccag | tgcgaaccaa | ggttgagcct | tggccttaaa | caccagactt | aaatgaccgc | 420 |
| ctgcgcgcgc | tttacgccca | ataattccgg | acaacgcttg | cccctacgt | attaccgcgg | 480 |
| ctgctggcac | gtagttagcc | ggggctttct | tctcaggtac | cgtcactccg | atagcagtta | 540 |
| ctctaccgga | cgttcttccc | tggcaacaga | gctttacgat | ccgaaaacct | tcatcactca | 600 |
| cgcggcgttg | ctccgtcagg | cttcgccca | ttgcggaaga | ttccctactg | ctgcctcccg | 660 |
| taggagtctg | ggccgtgtct | cagtcccagt | gtggccgttc | accctctcag | gtcggctacg | 720 |
| catcgtcgcc | ttggtgagcc | gttacctcac | caactagcta | atgcgccgca | ggcccatccg | 780 |
| caagtgacag | attgctccgt | ctttcatcat | cccctcagga | gaggaaatga | gatatccggt | 840 |
| attagctcac | gtttccgtgg | gttatc | | | | 866 |

<210> SEQ ID NO 24
<211> LENGTH: 1533
<212> TYPE: DNA
<213> ORGANISM: Pseudomonas sp.

<400> SEQUENCE: 24

| | | | | | |
|---|---|---|---|---|---|
| ctgaagagtt | tgatcatggc | tcagattgaa | cgctggcggc | aggcctaaca | catgcaagtc | 60 |
| gagcggatga | cgggagcttg | ctccttgatt | cagcggcgga | cgggtgagta | atgcctagga | 120 |
| atctgcctgg | tagtggggga | caacgtttcg | aaaggaacgc | taataccgca | tacgtcctac | 180 |
| gggagaaagc | aggggaccttc | gggccttgc | gctatcagat | gagcctaggt | cggattagct | 240 |
| agtaggtgag | gtaatggctc | acctaggcga | cgatccgtaa | ctggtctgag | aggatgatca | 300 |
| gtcacactgg | aactgagaca | cggtccagac | tcctacggga | ggcagcagtg | gggaatattg | 360 |
| gacaatgggc | gaaagcctga | tccagccatg | ccgcgtgtgt | gaagaaggtc | ttcggattgt | 420 |
| aaagcacttt | aagttgggag | gaagggcagt | aagctaatac | cttgctgttt | tgacgttacc | 480 |
| gacagaataa | gcaccggcta | actctgtgcc | agcagccgcg | gtaatacaga | gggtgcaagc | 540 |
| gttaatcgga | attactgggc | gtaaagcgcg | cgtaggtggt | tcgttaagtt | ggatgtgaaa | 600 |
| gccccgggct | caacctggga | actgcatcca | aaactggcga | gctagagtat | ggtagagggt | 660 |
| ggtggaattt | cctgtgtagc | ggtgaaatgc | gtagatatag | gaaggaacac | cagtggcgaa | 720 |
| ggcgaccacc | tggactgata | ctgacactga | ggtgcgaaag | cgtggggagc | aaacaggatt | 780 |
| agataccctg | gtagtccacg | ccgtaaacga | tgtcaactag | ccgttggaat | ccttgagatt | 840 |
| ttagtggcgc | agctaacgca | ttaagttgac | cgcctgggga | gtacggccgc | aaggttaaaa | 900 |
| ctcaaatgaa | ttgacggggg | cccgcacaag | cggtggagca | tgtggtttaa | ttcgaagcaa | 960 |
| cgcgaagaac | cttaccaggc | cttgacatgc | agagaacttt | ccagagatgg | attggtgcct | 1020 |

| | |
|---|---:|
| tcgggaactc tgacacaggt gctgcatggc tgtcgtcagc tcgtgtcgtg agatgttggg | 1080 |
| ttaagtcccg taacgagcgc aacccttgtc cttagttacc agcacgttat ggtgggcact | 1140 |
| ctaaggagac tgccggtgac aaaccggagg aaggtgggga tgacgtcaag tcatcatggc | 1200 |
| ccttacggcc tgggctacac acgtgctaca atggtcggta cagaggggttg ccaagccgcg | 1260 |
| aggtggagct aatctcacaa aaccgatcgt agtccggatc gcagtctgca actcgactgc | 1320 |
| gtgaagtcgg aatcgctagt aatcgcaaat cagaatgttg cggtgaatac gttcccgggc | 1380 |
| cttgtacaca ccgcccgtca caccatggga gtgggttgca ccagaagtag ctagtctaac | 1440 |
| cttcggggg acgttacca cggtgtgatt catgactggg gtgaagtcgt aacaaggtag | 1500 |
| ccgtagggga acctgcggct ggatcacctc ctt | 1533 |

<210> SEQ ID NO 25
<211> LENGTH: 1523
<212> TYPE: DNA
<213> ORGANISM: Streptomyces griseus

<400> SEQUENCE: 25

| | |
|---|---:|
| acggagagtt tgatcctggc tcaggacgaa cgctggcggc gtgcttaaca catgcaagtc | 60 |
| gaacgatgaa gcctttcggg gtggattagt ggcgaacggg tgagtaacac gtgggcaatc | 120 |
| tgccccttcac tctgggacaa gccctggaaa cggggtctaa taccggataa cactctgtcc | 180 |
| cgcatgggac ggggttaaaa gctccggcgg tgaaggatga gcccgcggcc tatcagcttg | 240 |
| ttggtggggt aatggcctac caaggcgacg acgggtagcc ggcctgagag ggcgaccggc | 300 |
| cacactggga ctgagacacg gcccagactc ctacgggagg cagcagtggg gaatattgca | 360 |
| caatgggcga aagcctgatg cagcgacgcc gcgtgaggga tgacggcctt cgggttgtaa | 420 |
| acctctttca gcagggaaga agcgagagtg acggtacctg cagaagaagc gccggctaac | 480 |
| tacgtgccag cagccgcggt aatacgtagg gcgcaagcgt tgtccggaat tattgggcgt | 540 |
| aaagagctcg taggcggctt gtcacgtcgg atgtgaaagc ccggggctta accccgggtc | 600 |
| tgcattcgat acgggctagc tagagtgtgg taggggagat cggaattcct ggtgtagcgg | 660 |
| tgaaatgcgc agatatcagg aggaacaccg gtggcgaagg cggatctctg gccattact | 720 |
| gacgctgagg agcgaaagcg tggggagcga acaggattag ataccctggt agtccacgcc | 780 |
| gtaaacgttg ggaactaggt gttggcgaca ttccacgtcg tcggtgccgc agctaacgca | 840 |
| ttaagttccc cgcctgggga gtacggccgc aaggctaaaa ctcaaaggaa ttgacggggg | 900 |
| cccgcacaag cagcggagca tgtggcttaa ttcgacgcaa cgcgaagaac cttaccaagg | 960 |
| cttgacatat accggaaagc atcagagatg gtgccccccct tgtggtcggt atacaggtgg | 1020 |
| tgcatggctg tcgtcagctc gtgtcgtgag atgttgggtt aagtcccgca acgagcgcaa | 1080 |
| cccttgttct gtgttgccag catgcccttc ggggtgatgg ggactcacag gagactgccg | 1140 |
| gggtcaactc ggaggaaggt ggggacgacg tcaagtcatc atgcccctta tgtcttgggc | 1200 |
| tgcacacgtg ctacaatggc cggtacaatg agctgcgatg ccgcgaggcg gagcgaatct | 1260 |
| caaaaagccg gtctcagttc ggattggggt ctgcaactcg accccatgaa gtcggagttg | 1320 |
| ctagtaatcg cagatcagca ttgctgcggt gaatacgttc ccgggccttg tacacaccgc | 1380 |
| ccgtcacgtc acgaaagtcg gtaacacccg aagccgtgg cccaacccct tgtgggaggg | 1440 |
| agctgtcgaa ggtgggactg gcgattggga cgaagtcgta acaaggtagc cgtaccggaa | 1500 |
| ggtgcggctg gatcacctcc ttt | 1523 |

```
<210> SEQ ID NO 26
<211> LENGTH: 299
<212> TYPE: PRT
<213> ORGANISM: Bacillus megaterium

<400> SEQUENCE: 26

Met Leu Thr Asp Leu His Ile Ala Val Ile Gly Gly Asp Ala Arg Gln
1               5                   10                  15

Leu Glu Val Ile Arg Lys Leu Ile Gln Leu Asp Ala Lys Thr Ser Leu
            20                  25                  30

Ile Gly Phe Asp Gln Leu Asp His Gly Phe Thr Gly Ala Thr Lys Tyr
        35                  40                  45

Gln Ile Glu Glu Leu Asp Phe Ser Asp Val Asp Ala Ile Ile Leu Pro
    50                  55                  60

Val Pro Gly Thr Asn His Glu Gly Gln Val Asp Thr Ile Phe Ser Asn
65                  70                  75                  80

Glu Lys Val Val Leu Thr Glu Glu Ile Leu Lys Lys Thr Pro Glu His
                85                  90                  95

Cys Ile Ile Tyr Ser Gly Ile Ser Asn Gly Tyr Leu Asn Glu Leu Val
            100                 105                 110

Lys Thr Thr Asn Arg Lys Leu Val Gln Leu Phe Glu Arg Asp Asp Val
        115                 120                 125

Ala Ile Tyr Asn Ser Ile Pro Thr Val Glu Gly Thr Ile Met Leu Val
    130                 135                 140

Ile Gln His Thr Asp Phe Thr Ile His Gly Ser Asn Ile Ser Val Leu
145                 150                 155                 160

Gly Leu Gly Arg Val Gly Met Ser Val Ala Arg Ser Phe Ala Ala Leu
                165                 170                 175

Gly Ala Asn Val Lys Val Gly Ala Arg Lys Ser Glu His Leu Ala Arg
            180                 185                 190

Ile Ala Glu Met Gly Leu Gln Pro Phe Tyr Leu Ser Glu Leu Asp Lys
        195                 200                 205

Glu Ile Ala Asp Ser Asp Ile Cys Ile Asn Thr Ile Pro Tyr Pro Ile
    210                 215                 220

Leu Thr Ala Lys Thr Leu Ser Asn Val Pro Thr His Ala Leu Ile Ile
225                 230                 235                 240

Asp Leu Ala Ser Lys Pro Gly Gly Thr Asp Phe Arg Tyr Ala Glu Lys
                245                 250                 255

Arg Gly Ile Lys Ala Ile Leu Ala Pro Gly Leu Pro Gly Ile Val Ala
            260                 265                 270

Pro Lys Thr Ala Gly Gln Ile Val Ala Asn Val Leu Val Asn Leu Leu
        275                 280                 285

Lys Asp Ala Ala Asp Ala Arg Glu Glu Lys Lys
    290                 295

<210> SEQ ID NO 27
<211> LENGTH: 297
<212> TYPE: PRT
<213> ORGANISM: Bacillus subtilis

<400> SEQUENCE: 27

Met Leu Thr Gly Leu Lys Ile Ala Val Ile Gly Gly Asp Ala Arg Gln
1               5                   10                  15

Leu Glu Ile Ile Arg Lys Leu Thr Glu Gln Gln Ala Asp Ile Tyr Leu
            20                  25                  30
```

Val Gly Phe Asp Gln Leu Asp His Gly Phe Thr Gly Ala Val Lys Cys
          35                  40                  45

Asn Ile Asp Glu Ile Pro Phe Gln Gln Ile Asp Ser Ile Ile Leu Pro
 50                  55                  60

Val Ser Ala Thr Thr Gly Glu Gly Val Val Ser Thr Val Phe Ser Asn
 65                  70                  75                  80

Glu Glu Val Val Leu Lys Gln Asp His Leu Asp Arg Thr Pro Ala His
                 85                  90                  95

Cys Val Ile Phe Ser Gly Ile Ser Asn Ala Tyr Leu Glu Asn Ile Ala
                100                 105                 110

Ala Gln Ala Lys Arg Lys Leu Val Lys Leu Phe Glu Arg Asp Asp Ile
            115                 120                 125

Ala Ile Tyr Asn Ser Ile Pro Thr Val Glu Gly Thr Ile Met Leu Ala
            130                 135                 140

Ile Gln His Thr Asp Tyr Thr Ile His Gly Ser Gln Val Ala Val Leu
145                 150                 155                 160

Gly Leu Gly Arg Thr Gly Met Thr Ile Ala Arg Thr Phe Ala Ala Leu
                165                 170                 175

Gly Ala Asn Val Lys Val Gly Ala Arg Ser Ser Ala His Leu Ala Arg
            180                 185                 190

Ile Thr Glu Met Gly Leu Val Pro Phe His Thr Asp Glu Leu Lys Glu
            195                 200                 205

His Val Lys Asp Ile Asp Ile Cys Ile Asn Thr Ile Pro Ser Met Ile
            210                 215                 220

Leu Asn Gln Thr Val Leu Ser Ser Met Thr Pro Lys Thr Leu Ile Leu
225                 230                 235                 240

Asp Leu Ala Ser Arg Pro Gly Gly Thr Asp Phe Lys Tyr Ala Glu Lys
                245                 250                 255

Gln Gly Ile Lys Ala Leu Leu Ala Pro Gly Leu Pro Gly Ile Val Ala
            260                 265                 270

Pro Lys Thr Ala Gly Gln Ile Leu Ala Asn Val Leu Ser Lys Leu Leu
            275                 280                 285

Ala Glu Ile Gln Ala Glu Glu Gly Lys
        290                 295

<210> SEQ ID NO 28
<211> LENGTH: 296
<212> TYPE: PRT
<213> ORGANISM: Paenibacillus cookii

<400> SEQUENCE: 28

Met Leu Thr Gly Leu Thr Ile Ala Ile Ile Gly Gly Asp Ala Arg Gln
1                5                  10                  15

Leu Glu Ile Ile Arg Lys Leu Thr Glu Gln His Ala Asp Ile Tyr Leu
            20                  25                  30

Ala Gly Phe Asp Gln Leu Asp Asp Gly Phe Thr Gly Thr Val Lys Cys
            35                  40                  45

Lys Ile Asp Glu Ile Pro Phe Gln Lys Ile Asp Ser Ile Ile Leu Pro
 50                  55                  60

Val Ser Ala Thr Thr Gly Glu Gly Val Val Ser Thr Val Phe Ser Asn
 65                  70                  75                  80

Glu Glu Val Val Leu Lys Gln Ser Tyr Leu Glu Arg Thr Pro Glu His
                 85                  90                  95

Cys Val Ile Tyr Ser Gly Ile Ser Asn Ala Tyr Leu Glu Gly Ile Ala
                100                 105                 110

Ser Glu Ala Gly Arg Lys Leu Val Lys Leu Phe Glu Arg Asp Asp Ile
            115                 120                 125

Ala Ile Phe Asn Ser Ile Pro Thr Val Glu Gly Thr Ile Met Met Ala
        130                 135                 140

Ile Gln His Thr Asp Tyr Thr Ile His Gly Ser Asn Val Ala Val Leu
145                 150                 155                 160

Gly Met Gly Arg Thr Gly Met Thr Ile Ala Arg Thr Phe Ala Ala Leu
                165                 170                 175

Gly Ala Lys Val Lys Val Gly Ala Arg Ser Ser Ala His Leu Ala Arg
                180                 185                 190

Ile Thr Glu Met Gly Leu Ser Pro Phe Gln Leu Glu Glu Leu Thr Glu
                195                 200                 205

His Val Asn Asp Ile Asp Ile Cys Ile Asn Thr Val Pro Ser Leu Ile
                210                 215                 220

Leu Asn Gln Ser Val Leu Ser Arg Met Thr Pro Lys Thr Leu Ile Leu
225                 230                 235                 240

Asp Leu Ala Ser Arg Pro Gly Gly Thr Asp Phe Lys Tyr Ala Glu Lys
                245                 250                 255

Gln Gly Ile Lys Ala Leu Leu Ala Pro Gly Leu Pro Gly Ile Val Ala
                260                 265                 270

Pro Lys Thr Ala Gly Gln Ile Ile Ala Asn Val Leu Ser Lys Leu Leu
                275                 280                 285

Ala Asp Leu Lys Lys Glu Gly Lys
        290                 295

<210> SEQ ID NO 29
<211> LENGTH: 299
<212> TYPE: PRT
<213> ORGANISM: Bacillus licheniformis

<400> SEQUENCE: 29

Met Leu Thr Gly Leu Thr Ile Ala Ile Ile Gly Gly Asp Ala Arg Gln
1               5                   10                  15

Leu Glu Ile Ile Arg Lys Leu Thr Glu Gln Asp Ala Lys Val Phe Leu
                20                  25                  30

Ile Gly Phe Asp Gln Leu Asp His Gly Phe Thr Gly Ala Thr Lys Leu
            35                  40                  45

Lys Leu Asn Glu Leu Asp Phe Gly Thr Ile Asp Ser Ile Ile Leu Pro
        50                  55                  60

Val Ser Gly Thr Ser Met Glu Gly Thr Val Ala Thr Val Phe Ser Asn
65                  70                  75                  80

Glu Lys Val Val Leu Lys Gln Glu His Leu Glu Lys Thr Lys Pro His
                85                  90                  95

Cys Ala Ile Tyr Ser Gly Ile Ser Asn Gln Tyr Leu Asp Gly Met Ala
            100                 105                 110

Lys Gly Ala Asn Arg Arg Leu Ile Lys Leu Phe Glu Arg Asp Asp Ile
        115                 120                 125

Ala Ile Tyr Asn Ser Ile Pro Thr Val Glu Gly Ala Ile Met Met Ala
        130                 135                 140

Ile Gln His Thr Asp Phe Thr Ile His Gly Ser Asn Val Met Val Leu
145                 150                 155                 160

Gly Leu Gly Arg Thr Gly Met Ser Ile Ser Arg Thr Phe Ser Ala Leu
                165                 170                 175

Gly Ala Arg Val Lys Val Gly Ala Arg Asp Ser Ala His Leu Ala Arg

```
            180             185             190
Ile Met Glu Met Gly Leu Thr Pro Phe His Thr Asn Glu Leu Ala Glu
            195             200             205

His Val Glu Asn Ile Asp Ile Cys Ile Asn Thr Ile Pro Ser Leu Ile
            210             215             220

Leu Asp Lys His Val Leu Ser Arg Met Thr Pro Arg Thr Leu Ile Leu
225             230             235             240

Asp Leu Ala Thr Arg Pro Gly Gly Thr Asp Phe Asp Phe Ala Glu Lys
            245             250             255

Gln Gly Ile Lys Ala Leu Leu Ala Pro Gly Leu Pro Gly Ile Val Ala
            260             265             270

Pro Lys Thr Ala Gly Gln Ile Ile Ala Asn Val Leu Cys Asn Leu Leu
            275             280             285

Ser Glu Leu Thr Thr Asp Arg Lys Gly Leu Ser
            290             295

<210> SEQ ID NO 30
<211> LENGTH: 298
<212> TYPE: PRT
<213> ORGANISM: Paenibacillus lautus

<400> SEQUENCE: 30

Met Leu Thr Gly Val Arg Thr Val Phe Val Gly Gly Asp Ala Arg Gln
1               5                   10                  15

Ile Glu Val Ile Arg Lys Cys Ala Glu Met Asp Ala Ser Val Met Ile
                20                  25                  30

Ala Gly Phe Glu Lys Leu Gln Asp Ser Phe Gln Gly Val Thr Arg Glu
            35                  40                  45

Pro Leu Thr Pro Glu Leu Leu Ser Asp Ala Asp Ala Leu Ile Leu Pro
        50                  55                  60

Val Val Gly Cys Asp Asp Glu Gly Arg Val Ser Ala Leu Phe Ser Glu
65                  70                  75                  80

Gly Pro Leu Arg Leu Gln Glu Glu His Ile Ala Ala Met Pro Gly His
                85                  90                  95

Gly Val Ile Tyr Thr Gly Met Ala Lys Pro Tyr Leu Arg Ser Leu Cys
            100                 105                 110

Asp Lys Tyr Lys Ile Lys Leu Val Glu Ile Leu Glu Arg Asp Asp Val
        115                 120                 125

Ala Ile Tyr Asn Ser Ile Pro Thr Ala Glu Gly Ala Leu Met Met Ala
130                 135                 140

Ile Gln Asn Thr Asp Phe Thr Ile His Gly Ser Thr Ser Met Val Leu
145                 150                 155                 160

Gly Met Gly Arg Thr Gly Phe Thr Met Ala Arg Ser Leu Gln Gly Leu
                165                 170                 175

Gly Ala Lys Ile Arg Met Gly Val Arg Lys Ser Glu His Tyr Ala Arg
            180                 185                 190

Ala Glu Glu Met Gly Trp Lys Pro Phe Leu Val Arg Asp Leu Gly Ser
        195                 200                 205

Tyr Val Ser Asp Ile Asp Leu Leu Phe Asn Thr Ile Pro Thr Met Ile
        210                 215                 220

Val Thr Ala Gln Ile Ile Ser Lys Met Pro Arg Glu Ala Val Ile Ile
225                 230                 235                 240

Asp Leu Ala Ser Ala Pro Gly Gly Cys Asp Phe Arg Tyr Ala Glu Lys
            245                 250                 255
```

```
Arg Gly Ile Lys Ala Met Leu Ala Pro Gly Leu Pro Gly Ile Val Ala
            260                 265                 270

Pro Lys Thr Ala Gly Ile Ile Met Ala Asn Thr Leu Val Glu Leu Ile
        275                 280                 285

Ser Glu Glu Ile Lys Ile Arg Glu Asp Ala
        290                 295

<210> SEQ ID NO 31
<211> LENGTH: 294
<212> TYPE: PRT
<213> ORGANISM: Oceanobacillus oncorhynchi

<400> SEQUENCE: 31

Met Ser Arg Arg Ile Ala Val Ile Gly Gly Asp Ala Arg Tyr Leu Glu
1               5                   10                  15

Leu Ile Lys Ile Leu Lys Ser Asn His Asp Asn Glu Val Ile Leu Cys
            20                  25                  30

Gly Phe Asp Lys Leu Glu Gln Gly Phe Thr Gly Leu Asn Glu Ser Ala
        35                  40                  45

Leu Asp Glu Leu Asp Gln Ser Lys Leu Asp Val Val Val Leu Pro Ile
    50                  55                  60

Thr Gly Thr Asp Ser Lys Gly Asn Val Glu Thr Val Phe Thr Asp Lys
65                  70                  75                  80

Lys Ile His Leu Asp Glu Ala Trp Phe Gln Lys Leu His Ala Glu Cys
                85                  90                  95

Met Ile Phe Thr Gly Met Thr Asn Ala Tyr Leu Thr Ser Met Ala Glu
            100                 105                 110

Lys Ala Gly Val Thr Leu Val Pro Leu Leu Asp Arg Asp Asp Val Ala
        115                 120                 125

Ile Tyr Asn Ser Ile Pro Thr Ala Glu Gly Ala Ile Met Met Ala Phe
    130                 135                 140

Glu His Thr Asp Gln Thr Val His Ser Ser Arg Val Met Val Val Gly
145                 150                 155                 160

Phe Gly Arg Val Gly Asn Thr Val Ala Asn Lys Phe Ser Ala Leu Gly
                165                 170                 175

Ala Lys Val Ser Val Cys Ala Arg Ser Ile Arg Asp Leu Ala Arg Ile
            180                 185                 190

Thr Glu Met Gly Leu Gln Ala Val Pro Leu His Glu Leu Ser Asn His
        195                 200                 205

Thr Glu Asn Cys Asp Ile Leu Ile Asn Thr Ile Pro Ser Leu Val Val
    210                 215                 220

Thr Lys Glu Ala Ile Gln Asn Leu Pro Thr Asn Ala Val Ile Ile Asp
225                 230                 235                 240

Leu Ala Ser Lys Pro Gly Gly Thr Asp Phe Asp Phe Ala Lys Lys Arg
                245                 250                 255

Gly Ile Gln Ala Ile Leu Ala Arg Ser Leu Pro Gly Ile Val Ala Pro
            260                 265                 270

Arg Thr Ala Gly Lys Ile Leu Ala Asn Val Met Glu Gln Ile Leu Glu
        275                 280                 285

Glu Glu Arg Ala Ser Glu
        290

<210> SEQ ID NO 32
<211> LENGTH: 299
<212> TYPE: PRT
<213> ORGANISM: Bacillus amyloliquefaciens
```

<400> SEQUENCE: 32

```
Met Leu Thr Gly Val Gln Ile Val Phe Leu Gly Gly Asp Ala Arg Gln
1               5                   10                  15

Ile Glu Val Ile Arg Lys Cys Ser Glu Met Asp Ala Thr Val Ser Val
                20                  25                  30

Val Gly Phe Asp Asn Leu Lys Glu Lys Leu Gln Gly Val Thr Arg Asp
            35                  40                  45

His Leu Thr Ala Glu Leu Leu Ala Ala Ala Asp Val Leu Val Leu Pro
    50                  55                  60

Val Val Gly Cys Asp Asp Asn Gly Ile Ile His Thr Gln Phe Ser Asn
65                  70                  75                  80

Glu Ser Leu Lys Leu Gln Asp Glu His Met Ala Ala Leu Arg Arg Gly
                85                  90                  95

Cys Lys Val Tyr Thr Gly Met Ala Lys Pro Tyr Leu Arg Ser Leu Cys
            100                 105                 110

Ala His His Glu Ile Lys Leu Ile Glu Leu Leu Asp Arg Asp Glu Val
        115                 120                 125

Ala Ile Ser Asn Ser Ile Pro Thr Ser Glu Gly Ala Leu Val Met Ala
    130                 135                 140

Ile Gln Asn Thr Asp Phe Thr Ile His Gly Ser Asn Cys Met Val Leu
145                 150                 155                 160

Gly Leu Gly Arg Thr Gly Phe Thr Met Ala Lys Ser Leu Gln Gly Leu
                165                 170                 175

Gly Ala Lys Val Lys Val Gly Val Arg Ser Glu Lys Asp Val Ala Arg
            180                 185                 190

Ala Glu Val Met Gly Trp Glu Pro Phe Leu Thr Arg Asp Leu Ala Asp
        195                 200                 205

His Val Arg Asn Ile Asp Leu Ile Phe Asn Thr Ile Pro Thr Met Ile
    210                 215                 220

Val Thr Ala Gln Ile Leu Ser Arg Met Pro Gln Ser Ala Val Ile Ile
225                 230                 235                 240

Asp Leu Ala Ser Ala Pro Gly Gly Cys Asp Phe Arg Tyr Ala Glu Lys
                245                 250                 255

Arg Gly Ile Lys Ala Leu Leu Ala Pro Gly Leu Pro Gly Ile Val Ala
            260                 265                 270

Pro Lys Thr Ala Gly Ser Ile Ala Asn Thr Leu Val Gln Leu Ile
        275                 280                 285

Ser Asp Glu Phe Lys Thr Arg Gly Asp Gly Gln
    290                 295
```

<210> SEQ ID NO 33
<211> LENGTH: 300
<212> TYPE: PRT
<213> ORGANISM: Bacillus sp.

<400> SEQUENCE: 33

```
Met Leu Thr Gly Leu Gln Ile Ala Val Ile Gly Gly Asp Ala Arg Gln
1               5                   10                  15

Leu Glu Val Ile Arg Lys Leu Thr Glu Leu Asp Ala Lys Leu Tyr Leu
                20                  25                  30

Val Gly Phe Glu Gln Leu Asp His Ala Phe Ser Gly Ala Val Lys Glu
            35                  40                  45

Lys Leu Asp Glu Val Asp Phe Thr Cys Ile Asp Ala Ile Ile Leu Pro
    50                  55                  60
```

Val Pro Gly Ala Gly Val Asp Gly Gln Ile Asp Thr Ile Phe Ser Asn
65                  70                  75                  80

Glu Lys Ile Thr Ile Asn Glu Glu Ile Leu Lys Lys Thr Pro Gln His
            85                  90                  95

Cys Lys Ile Tyr Ser Gly Ile Asn Pro Pro Tyr Leu Gln Glu Ile Ser
            100                 105                 110

Thr Lys Ala Asp Arg Glu Val Val Gln Leu Phe Asn Arg Asp Asp Val
            115                 120                 125

Ala Ile Tyr Asn Ser Ile Pro Thr Val Glu Gly Ala Leu Met Met Ala
130                 135                 140

Ile Gln His Thr Asp Phe Thr Ile His Gly Ser Asn Val Thr Val Leu
145                 150                 155                 160

Gly Leu Gly Arg Thr Gly Met Ser Ile Ala Arg Ala Phe His Ala Leu
            165                 170                 175

Gly Ala Lys Val Lys Val Gly Ala Arg Lys Ser Glu His Ile Ala Arg
            180                 185                 190

Ile Thr Glu Met Gly Leu Thr Pro Phe His Leu Ser Asp Ile Glu Glu
            195                 200                 205

Ala Val Val Asp Thr Asp Ile Cys Ile Asn Thr Ile Pro Val Gln Val
210                 215                 220

Val Val Ala Ser Val Ile Ala Lys Met Pro Val His Thr Leu Ile Ile
225                 230                 235                 240

Asp Leu Ala Ser Lys Pro Gly Gly Thr Asp Phe Arg Tyr Ala Glu Lys
            245                 250                 255

Arg Gly Val Lys Ala Leu Leu Ala Pro Gly Leu Pro Gly Ile Val Ala
            260                 265                 270

Pro Lys Thr Ala Gly Arg Ile Leu Ala Asn Val Leu Ser Gln Leu Ile
            275                 280                 285

Leu Ala Asn Phe Asp Glu Arg Glu Asp Lys Gln Ser
            290                 295                 300

<210> SEQ ID NO 34
<211> LENGTH: 299
<212> TYPE: PRT
<213> ORGANISM: Paenibacillus chibensis

<400> SEQUENCE: 34

Met Leu Thr Gly Val Gln Ile Val Phe Leu Gly Gly Asp Ala Arg Gln
1               5                   10                  15

Val Glu Val Ile Arg Lys Cys Ser Glu Met Asp Ala Thr Val Ser Val
            20                  25                  30

Val Gly Phe Asp Asn Leu Lys Gln Lys Leu Gln Gly Val Thr Arg Asp
            35                  40                  45

His Leu Thr Ala Glu Leu Leu Ala Ala Ala Asp Val Leu Val Leu Pro
50                  55                  60

Val Val Gly Cys Asp Asp Asn Gly Asn Ile His Thr Gln Phe Ser Asn
65                  70                  75                  80

Glu Pro Leu Lys Leu Gln Asp Glu His Met Ala Ser Leu Arg Lys Gly
            85                  90                  95

Cys Lys Val Tyr Thr Gly Met Ala Lys Pro Tyr Leu Arg Ser Leu Cys
            100                 105                 110

Ala Gln His Glu Ile Lys Leu Val Glu Leu Leu Asp Arg Asp Glu Val
            115                 120                 125

Ala Ile Ser Asn Ser Ile Pro Thr Ala Glu Gly Ala Leu Val Met Ala

-continued

```
                130                 135                 140
Ile Gln Asn Thr Asp Phe Thr Ile His Gly Ser Arg Cys Met Val Leu
145                 150                 155                 160

Gly Leu Gly Arg Thr Gly Phe Thr Met Ala Lys Ser Leu Gln Gly Leu
                165                 170                 175

Gly Ala Lys Val Lys Val Gly Val Arg Ser Glu Lys Asp Val Ala Arg
                180                 185                 190

Ala Glu Val Met Gly Trp Glu Pro Phe Leu Thr Arg Asp Leu Gly Asp
                195                 200                 205

His Val Ser Asn Ile Asp Leu Ile Phe Asn Thr Ile Pro Thr Met Ile
                210                 215                 220

Val Thr Ala Gln Ile Leu Ser Lys Met Pro Leu Ser Ser Val Ile Ile
225                 230                 235                 240

Asp Leu Ala Ser Ala Pro Gly Gly Cys Asp Phe Arg Tyr Ala Glu Lys
                245                 250                 255

Arg Gly Ile Lys Ala Leu Leu Ala Pro Gly Leu Pro Gly Ile Val Ala
                260                 265                 270

Pro Lys Thr Ala Gly Leu Ile Ile Ala Gly Ser Leu Val Gln Leu Ile
                275                 280                 285

Ser Asp Glu Phe Lys Thr Arg Gly Asp Gly Glu
                290                 295

<210> SEQ ID NO 35
<211> LENGTH: 299
<212> TYPE: PRT
<213> ORGANISM: Bacillus flexus

<400> SEQUENCE: 35

Met Leu Thr Asp Leu His Ile Ala Val Ile Gly Gly Asp Ala Arg Gln
1               5                   10                  15

Leu Glu Val Ile Arg Lys Leu Ile Gln Leu Asp Ala Lys Thr Ser Leu
                20                  25                  30

Ile Gly Phe Asp Gln Leu Asp His Gly Phe Thr Gly Ala Thr Lys Tyr
                35                  40                  45

Gln Ile Asp Glu Leu Asn Phe Ser Asp Val Asp Ala Ile Ile Leu Pro
                50                  55                  60

Val Pro Gly Thr Asn His Glu Gly Gln Val Asp Thr Ile Phe Ser Asn
65                  70                  75                  80

Glu Lys Val Ile Leu Thr Glu Glu Ile Leu Ala Ser Thr Pro Ala His
                85                  90                  95

Cys Thr Ile Tyr Ser Gly Ile Ser Asn Asp Tyr Leu Asn Ser Leu Val
                100                 105                 110

Gln Lys Thr Asn Arg Thr Leu Ile Gln Leu Phe Glu Arg Asp Asp Val
                115                 120                 125

Ala Ile Tyr Asn Ser Ile Pro Thr Val Glu Gly Thr Ile Met Leu Val
                130                 135                 140

Ile Gln His Thr Asp Phe Thr Ile His Gly Ala Asn Ile Ser Val Leu
145                 150                 155                 160

Gly Leu Gly Arg Val Gly Met Ser Val Ala Arg Ser Phe Ala Ala Leu
                165                 170                 175

Gly Ala Asn Val Lys Val Gly Ala Arg Lys Ser Glu His Leu Ala Arg
                180                 185                 190

Ile Ser Glu Met Gly Leu Thr Pro Phe His Leu Asn Asp Leu Ala Gln
                195                 200                 205
```

-continued

```
Glu Ile Thr Asp Ser Asp Ile Cys Ile Asn Thr Ile Pro Tyr Pro Val
    210                 215                 220

Leu Thr Ser Ser Val Leu Ala Asn Ile Pro Thr His Ala Leu Val Val
225                 230                 235                 240

Asp Leu Ala Ser Lys Pro Gly Gly Thr Asp Phe Arg Tyr Ala Glu Lys
                245                 250                 255

Arg Gly Ile Lys Ala Ile Leu Ala Pro Gly Leu Pro Gly Ile Val Ala
            260                 265                 270

Pro Lys Thr Ala Gly Gln Ile Val Ala Asn Val Ile Val Thr Leu Leu
        275                 280                 285

Lys Glu Ala Ala Asp Gln Arg Glu Glu Lys Gln
    290                 295
```

<210> SEQ ID NO 36
<211> LENGTH: 300
<212> TYPE: PRT
<213> ORGANISM: Bacillus firmus

<400> SEQUENCE: 36

```
Met Leu Thr Gly Thr Gln Ile Ala Val Ile Gly Gly Asp Ala Arg Gln
1               5                   10                  15

Leu Glu Ile Ile Arg Lys Leu Thr Glu Leu Asp Ala Lys Leu Ser Leu
                20                  25                  30

Ile Gly Phe Glu Gln Leu Asp His Ala Phe Ser Gly Ala Val Lys Glu
            35                  40                  45

Lys Ile Asp Glu Val Asp Phe Ser His Ile Asp Ala Ile Ile Leu Pro
        50                  55                  60

Val Pro Gly Thr Gly Leu Gly Gln Ile Glu Thr Ile Phe Ser Asn
65                  70                  75                  80

Glu Lys Val Thr Leu Glu Glu Ile Leu Ser Gln Thr Pro Ala His
                85                  90                  95

Cys Thr Val Tyr Ser Gly Ile Thr Asn Ser Tyr Leu Thr Gly Val Thr
            100                 105                 110

Lys Ser Ala Asp Arg Arg Leu Val Gln Leu Phe Glu Arg Asp Asp Val
        115                 120                 125

Ala Ile Tyr Asn Ser Ile Pro Thr Val Glu Gly Thr Ile Met Met Ala
    130                 135                 140

Ile Gln His Thr Asp Phe Thr Ile His Gly Ser Asn Ile Ala Val Ile
145                 150                 155                 160

Gly Leu Gly Arg Val Gly Met Ser Val Ala Arg Thr Phe Arg Ala Leu
                165                 170                 175

Gly Ala Lys Val Lys Val Gly Ala Arg Lys Ser Glu His Ile Ala Arg
            180                 185                 190

Ile Thr Glu Met Gly Leu Thr Pro Phe Asn Leu Lys Glu Ile Glu Asp
        195                 200                 205

Ala Val Lys Asp Val Asp Ile Cys Ile Asn Thr Ala Pro His Leu Val
    210                 215                 220

Val Thr Ala Ser Val Ile Ser Lys Met Pro Thr His Thr Leu Ile Ile
225                 230                 235                 240

Asp Leu Ala Ser Lys Pro Gly Gly Thr Asp Phe Arg Tyr Ala Glu Lys
                245                 250                 255

Arg Gly Val Lys Ala Leu Leu Ala Pro Gly Leu Pro Gly Ile Val Ala
            260                 265                 270

Pro Lys Thr Ala Gly Gln Ile Leu Ala Asn Val Leu Ser Gln Leu Ile
        275                 280                 285
```

```
Met Glu Asp Leu Gln Lys Arg Lys Gly Asn Thr Lys
    290                 295                 300

<210> SEQ ID NO 37
<211> LENGTH: 291
<212> TYPE: PRT
<213> ORGANISM: Virgilia halophilus

<400> SEQUENCE: 37

Met Asn Leu Lys Asp Lys Lys Ile Leu Leu Ile Gly Gly Asp Glu Arg
1               5                   10                  15

Tyr Leu Glu Val Val Lys Lys Leu Asp Asp Leu Gly Ala Ser Val Val
            20                  25                  30

Leu Ala Gly Tyr Asp Lys Ala Gly Leu Ser Ser Gly Arg Val Gln Ile
        35                  40                  45

Ser Lys Leu Glu Asp Val Asn Phe Ser Asn Leu Tyr Ala Ile Leu Leu
    50                  55                  60

Pro Val Ser Gly Thr Asp Gly Glu Gly Asn Ile Thr Met Ser Ser Phe
65                  70                  75                  80

Thr Asp Gln Gln Leu Cys Leu Thr Glu Gln Met Ile Ser Gln Leu Pro
                85                  90                  95

Pro Ser Cys Lys Ile Tyr Thr Gly Val Ser Gly Ser Phe Leu Lys Arg
            100                 105                 110

Met Gly Ser Lys Phe Gln Lys Glu Ile Ile Ser Ile Leu Ala Arg Glu
        115                 120                 125

Asp Ile Ala Ile Tyr Asn Ser Ile Pro Thr Ala Glu Gly Ala Leu Gln
    130                 135                 140

Leu Ala Met Glu Gln Thr Asp Tyr Thr Met His Ser Ala Ser Val Met
145                 150                 155                 160

Val Leu Gly Phe Gly Lys Val Gly Met Thr Thr Ala Arg Leu Phe Ser
                165                 170                 175

Ala Val Gly Cys Asn Val Ser Val Ala Ile Arg Lys Asp Ser Ala Ala
            180                 185                 190

Ala Arg Val Arg Glu Met Gly Leu Lys Pro Leu Tyr Thr His His Leu
        195                 200                 205

Ser Glu Glu Ile Gly Gln Tyr Gln Ile Ile Asn Thr Val Pro Asp
    210                 215                 220

Leu Val Leu Asp Glu Ser Leu Leu Asn Ile Val Ser Ser Lys Ala Leu
225                 230                 235                 240

Ile Ile Asp Leu Ala Ser Ser Pro Gly Gly Val Asp Phe Ser Val Ala
                245                 250                 255

Asp Glu Leu Gly Ile Arg Thr Ile His Ala Leu Gly Leu Pro Gly Lys
            260                 265                 270

Val Ala Pro Lys Thr Ala Gly Ser Ile Ile Ala Asp Thr Phe Val Ser
        275                 280                 285

Leu Leu Ser
    290

<210> SEQ ID NO 38
<211> LENGTH: 269
<212> TYPE: PRT
<213> ORGANISM: Virgibacillus halophilus

<400> SEQUENCE: 38

Met Lys Thr Ile Val Thr Gly Phe Asn Lys Leu Asp Gln Gly Phe Thr
1               5                   10                  15
```

```
Gly Val Gln His Val Glu Phe Ala Glu Met Glu His Glu Asp Ile Asp
                20                  25                  30

Val Val Val Leu Pro Ile Thr Gly Thr Gln Lys Gly Gly Lys Val Glu
            35                  40                  45

Thr Val Phe Ser Asp Glu Glu Ile Val Leu Thr Lys Asp Trp Phe Glu
50                  55                  60

Lys Phe Gln Arg Pro Thr Pro Val Phe Thr Gly Ile Ser Asn Gln Asp
65                  70                  75                  80

Leu Asp Gly Met Val Lys Asn Ser Lys Ala Gln Ile Ile Pro Leu Leu
                85                  90                  95

Asp Arg Asp Asp Val Ala Ile Tyr Asn Ser Ile Pro Thr Ala Glu Gly
                100                 105                 110

Thr Ile Met Met Ala Met Glu His Thr Asp Tyr Thr Ile His Ser Ser
            115                 120                 125

Arg Val Ile Val Ala Gly Phe Gly Arg Val Gly His Thr Val Ala Asn
130                 135                 140

Lys Phe Ser Ala Leu Gly Ala Lys Val Ser Val Ala Ala Ser Ser Ile
145                 150                 155                 160

His Asp Ile Ala Arg Ile Asn Glu Met Gly Leu Phe Ala Ile Thr Met
                165                 170                 175

Lys Glu Leu Ala Lys Ala Ala Ala Asp Cys Asp Ile Leu Ile Asn Thr
            180                 185                 190

Ile Pro Ala Pro Val Ile Asn Lys Glu Ala Ile Ser Gln Leu Pro His
            195                 200                 205

His Ala Leu Ile Phe Asp Leu Ala Ser Lys Pro Gly Gly Thr Asp Phe
210                 215                 220

Asp Tyr Ala Lys Arg Arg Gly Ile Lys Ala Ile Leu Ser Glu Ser Leu
225                 230                 235                 240

Pro Gly Val Val Ala Pro Lys Thr Ala Gly Lys Ile Leu Ala Asp Val
                245                 250                 255

Ile Ile Gln Ile Leu Ser Gln Arg Lys Gly Phe Glu Gln
                260                 265

<210> SEQ ID NO 39
<211> LENGTH: 299
<212> TYPE: PRT
<213> ORGANISM: Paenibacillus azoreducens

<400> SEQUENCE: 39

Met Leu Thr Gly Val Gln Ile Val Phe Leu Gly Gly Asp Ala Arg Gln
1               5                   10                  15

Ile Glu Val Ile Arg Lys Cys Ser Glu Met Asp Ala Thr Val Ser Val
                20                  25                  30

Val Gly Phe Asp Asn Leu Lys Glu Lys Leu Gln Gly Val Thr Arg Asp
            35                  40                  45

Gln Leu Thr Gly Glu Leu Leu Ala Gly Ala Asp Val Leu Val Leu Pro
50                  55                  60

Val Val Gly Cys Asp Asp Asn Gly Ile Ile His Thr Gln Phe Ser Asn
65                  70                  75                  80

Glu Ser Leu Lys Leu Gln Asp Glu His Met Ala Ser Leu Arg Arg Gly
                85                  90                  95

Cys Lys Val Tyr Thr Gly Met Ala Lys Pro Tyr Leu Arg Ser Leu Cys
                100                 105                 110

Ala His His Glu Ile Arg Leu Val Glu Leu Leu Asp Arg Asp Glu Val
```

```
            115                 120                 125
Ala Ile Ser Asn Ser Ile Pro Thr Ala Glu Gly Ala Leu Val Met Ala
        130                 135                 140
Ile Gln Asn Thr Asp Phe Thr Ile His Gly Ser Asp Cys Met Val Leu
145                 150                 155                 160
Gly Leu Gly Arg Thr Gly Phe Thr Met Ala Lys Ser Leu Gln Gly Leu
                165                 170                 175
Gly Ala Arg Val Lys Val Gly Val Arg Ser Glu Arg Asp Phe Ala Arg
            180                 185                 190
Ala Glu Val Met Gly Trp Glu Pro Phe Leu Thr Arg Asp Leu Ala Asp
                195                 200                 205
Tyr Val Arg Ser Ile Asp Leu Ile Phe Asn Thr Ile Pro Thr Met Ile
210                 215                 220
Val Thr Ala Gln Ile Leu Ser Arg Met Pro Gln Asn Thr Val Ile Ile
225                 230                 235                 240
Asp Leu Ala Ser Ala Pro Gly Gly Cys Asp Phe Arg Tyr Ala Glu Lys
                245                 250                 255
Arg Gly Ile Lys Ala Leu Leu Ala Pro Gly Leu Pro Gly Ile Val Ala
            260                 265                 270
Pro Lys Thr Ala Gly Ser Ile Ile Ala Asn Ser Leu Val Gln Met Ile
                275                 280                 285
Ser Asp Glu Phe Lys Thr Arg Gly Asp Gly Glu
            290                 295
```

<210> SEQ ID NO 40
<211> LENGTH: 296
<212> TYPE: PRT
<213> ORGANISM: Artificial Sequence
<220> FEATURE:
<223> OTHER INFORMATION: Consensus DpaA sequence

<400> SEQUENCE: 40

```
Thr Gly Lys His Ile Ala Val Ile Gly Gly Asp Ala Arg Gln Leu Glu
1               5                   10                  15
Leu Ile Arg Lys Leu Val Glu Leu Gly Ala Lys Val Ser Leu Val Gly
            20                  25                  30
Phe Asp Gln Leu Asp His Gly Phe Thr Gly Ala Thr Lys Ser Ser Ser
        35                  40                  45
Leu Glu Glu Ala Leu Ser Asp Val Asp Val Ile Leu Pro Val Pro
    50                  55                  60
Gly Thr Asn Asp Glu Gly Asn Val Asp Thr Val Phe Ser Asn Glu Lys
65                  70                  75                  80
Leu Val Leu Thr Glu Glu Leu Leu Glu Leu Thr Pro Glu His Cys Thr
                85                  90                  95
Ile Phe Ser Gly Ile Ala Asn Pro Tyr Leu Lys Glu Leu Ala Lys Glu
            100                 105                 110
Thr Asn Arg Lys Leu Val Glu Leu Phe Glu Arg Asp Asp Val Ala Ile
        115                 120                 125
Leu Asn Ser Ile Pro Thr Ala Glu Gly Ala Ile Met Met Ala Ile Glu
    130                 135                 140
His Thr Pro Ile Thr Ile His Gly Ser Asn Val Leu Val Leu Gly Phe
145                 150                 155                 160
Gly Arg Thr Gly Met Thr Leu Ala Arg Thr Leu Lys Ala Leu Gly Ala
                165                 170                 175
Asn Val Thr Val Gly Ala Arg Lys Ser Ala His Leu Ala Arg Ile Thr
```

```
Glu Met Gly Leu Ser Pro Phe His Leu Ser Glu Leu Ala Glu Glu Val
            195                 200                 205

Gly Lys Ile Asp Ile Ile Phe Asn Thr Ile Pro Ala Leu Val Leu Thr
    210                 215                 220

Lys Glu Val Leu Ser Lys Met Pro Pro Glu Ala Leu Ile Ile Asp Leu
225                 230                 235                 240

Ala Ser Lys Pro Gly Gly Thr Asp Phe Glu Tyr Ala Glu Lys Arg Gly
                245                 250                 255

Ile Lys Ala Leu Leu Ala Pro Gly Leu Pro Gly Lys Val Ala Pro Lys
            260                 265                 270

Thr Ala Gly Gln Ile Leu Ala Asn Val Leu Ser Gln Leu Leu Ala Glu
            275                 280                 285

Asp Leu Ile Ala Arg Lys Glu Asn
            290                 295

<210> SEQ ID NO 41
<211> LENGTH: 296
<212> TYPE: PRT
<213> ORGANISM: Artificial Sequence
<220> FEATURE:
<223> OTHER INFORMATION: DpaA consensus sequence

<400> SEQUENCE: 41

Thr Gly Lys His Ile Ala Val Ile Gly Gly Asp Ala Arg Gln Leu Glu
1               5                   10                  15

Leu Ile Arg Lys Leu Val Glu Leu Gly Ala Lys Val Ser Leu Val Gly
            20                  25                  30

Phe Asp Gln Leu Asp His Gly Phe Thr Gly Ala Thr Lys Ser Ser Ser
        35                  40                  45

Leu Glu Glu Ala Leu Ser Asp Val Asp Val Ile Ile Leu Pro Val Pro
50                  55                  60

Gly Thr Asn Asp Glu Gly Asn Val Asp Thr Val Phe Ser Asn Glu Lys
65                  70                  75                  80

Leu Val Leu Thr Glu Glu Leu Leu Glu Leu Thr Pro Glu His Cys Thr
                85                  90                  95

Ile Phe Ser Gly Ile Ala Asn Pro Tyr Leu Lys Glu Leu Ala Lys Glu
            100                 105                 110

Thr Asn Arg Lys Leu Val Glu Leu Phe Glu Arg Asp Asp Val Ala Ile
            115                 120                 125

Leu Asn Ser Ile Pro Thr Ala Glu Gly Ala Ile Met Met Ala Ile Glu
130                 135                 140

His Thr Pro Ile Thr Ile His Gly Ser Asn Val Leu Val Leu Gly Phe
145                 150                 155                 160

Gly Arg Thr Gly Met Thr Leu Ala Arg Thr Leu Lys Ala Leu Gly Ala
                165                 170                 175

Asn Val Thr Val Gly Ala Arg Lys Ser Ala His Leu Ala Arg Ile Thr
            180                 185                 190

Glu Met Gly Leu Ser Pro Phe His Leu Ser Glu Leu Ala Glu Glu Val
            195                 200                 205

Gly Lys Ile Asp Ile Ile Phe Asn Thr Ile Pro Ala Leu Val Leu Thr
    210                 215                 220

Lys Glu Val Leu Ser Lys Met Pro Pro Glu Ala Leu Ile Ile Asp Leu
225                 230                 235                 240

Ala Ser Lys Pro Gly Gly Thr Asp Phe Glu Tyr Ala Glu Lys Arg Gly
```

```
                    245                 250                 255
Ile Lys Ala Leu Leu Ala Pro Gly Leu Pro Gly Lys Val Ala Pro Lys
            260                 265                 270

Thr Ala Gly Gln Ile Leu Ala Asn Val Leu Ser Gln Leu Leu Ala Glu
        275                 280                 285

Asp Leu Ile Ala Arg Lys Glu Asn
    290                 295

<210> SEQ ID NO 42
<211> LENGTH: 201
<212> TYPE: PRT
<213> ORGANISM: Bacillus megaterium

<400> SEQUENCE: 42

Met Ser Leu Lys Gly Lys Arg Ile Gly Phe Gly Leu Thr Gly Ser His
1               5                   10                  15

Cys Thr Tyr Asp Ala Val Met Pro Glu Ile Glu Lys Leu Val Asn Leu
            20                  25                  30

Gly Ala Glu Val Leu Pro Val Val Ser Tyr Thr Val Gln Ser Thr Asn
        35                  40                  45

Thr Arg Phe Gly Asp Gly Glu Asp Trp Val Lys Ile Glu Glu Leu
    50                  55                  60

Thr Gly His Ala Val Ile Asn Thr Ile Val Lys Ala Glu Pro Leu Gly
65                  70                  75                  80

Pro Lys Ile Pro Leu Asp Cys Met Val Val Ala Pro Ile Thr Gly Asn
                85                  90                  95

Thr Met Ser Lys Phe Ala Asn Ala Met Thr Glu Ser Pro Val Leu Met
            100                 105                 110

Ala Ala Lys Ala Thr Leu Arg Asn Asn Lys Pro Val Val Leu Gly Ile
        115                 120                 125

Ser Thr Asn Asp Ala Leu Gly Leu Asn Gly Val Asn Leu Met Arg Leu
    130                 135                 140

Met Ala Thr Lys Asn Ile Tyr Phe Ile Pro Phe Gly Gln Asp Asp Pro
145                 150                 155                 160

Val Leu Lys Pro Asn Ser Met Val Ala Arg Met Thr Met Leu Ser Asp
                165                 170                 175

Thr Val Tyr Ala Ala Leu Glu Asp Lys Gln Ile Gln Pro Val Ile Val
            180                 185                 190

Glu Arg Phe Arg Asp Gly Gln Glu Ser
        195                 200

<210> SEQ ID NO 43
<211> LENGTH: 200
<212> TYPE: PRT
<213> ORGANISM: Bacillus subtilis

<400> SEQUENCE: 43

Met Ser Ser Leu Lys Gly Lys Arg Ile Gly Phe Gly Leu Thr Gly Ser
1               5                   10                  15

His Cys Thr Tyr Glu Ala Val Phe Pro Gln Ile Glu Ala Leu Val Asn
            20                  25                  30

Glu Gly Ala Glu Val Arg Pro Val Val Thr Phe Asn Val Lys Ser Thr
        35                  40                  45

Asn Thr Arg Phe Gly Glu Gly Ala Glu Trp Val Lys Lys Ile Glu Glu
    50                  55                  60

Leu Thr Gly Tyr Glu Ala Ile Asp Ser Ile Val Lys Ala Glu Pro Leu
```

```
              65                  70                  75                  80
Gly Pro Lys Leu Pro Leu Asp Cys Met Val Ile Ala Pro Leu Thr Gly
                85                  90                  95
Asn Ser Met Ser Lys Leu Ala Asn Ala Met Thr Asp Ser Pro Val Leu
               100                 105                 110
Met Ala Ala Lys Ala Thr Ile Arg Asn Asn Arg Pro Val Val Leu Gly
               115                 120                 125
Ile Ser Thr Asn Asp Ala Leu Gly Leu Asn Gly Thr Asn Leu Met Arg
        130                 135                 140
Leu Met Ser Thr Lys Asn Ile Phe Phe Ile Pro Phe Gly Gln Asp Asp
145                 150                 155                 160
Pro Phe Lys Lys Pro Asn Ser Met Val Ala Lys Met Asp Leu Leu Pro
                165                 170                 175
Gln Thr Ile Glu Lys Ala Leu Leu His Gln Gln Leu Pro Ile Leu
                180                 185                 190
Val Glu Asn Tyr Gln Gly Asn Asp
        195                 200
```

<210> SEQ ID NO 44
<211> LENGTH: 196
<212> TYPE: PRT
<213> ORGANISM: Paenibacillus cookii

<400> SEQUENCE: 44

```
Met Ser Leu Lys Gly Lys Arg Ile Gly Phe Gly Leu Thr Gly Ser His
1               5                   10                  15
Cys Thr Tyr Glu Glu Val Phe Pro Gln Ile Glu Ala Leu Ile Ser Gln
                20                  25                  30
Gly Ala Glu Val Arg Pro Val Val Thr Ser Thr Val Gln Ser Thr Asp
            35                  40                  45
Thr Arg Phe Gly Glu Gly Gly Asp Trp Val Arg Lys Ile Glu Glu Ala
    50                  55                  60
Thr Gly Phe Glu Ala Ile Asp Ser Ile Val Lys Ala Glu Pro Leu Gly
65                  70                  75                  80
Pro Lys Leu Pro Leu Asp Cys Met Val Ile Ala Pro Leu Thr Gly Asn
                85                  90                  95
Ser Met Ser Lys Leu Ala Asn Ala Met Thr Asp Ser Pro Val Leu Met
               100                 105                 110
Ala Ala Lys Ala Thr Ile Arg Asn Gly Arg Pro Val Val Leu Gly Ile
               115                 120                 125
Ser Thr Asn Asp Gly Leu Gly Leu Asn Gly Thr Asn Leu Met Arg Leu
        130                 135                 140
Met Ser Ala Lys Asn Ile Tyr Phe Ile Pro Phe Gly Gln Asp His
145                 150                 155                 160
Val Lys Lys Pro Thr Ser Leu Val Ala Arg Met Asp Leu Leu Pro Ile
                165                 170                 175
Thr Val Glu Lys Ala Leu Leu His Gln Gln Val Gln Pro Val Leu Val
                180                 185                 190
His His His Glu
        195
```

<210> SEQ ID NO 45
<211> LENGTH: 196
<212> TYPE: PRT
<213> ORGANISM: Bacillus licheniformis

```
<400> SEQUENCE: 45

Met Ser Ile Lys Gly Lys Arg Ile Gly Phe Gly Leu Thr Gly Ser His
1               5                   10                  15

Cys Thr Tyr Asp Ala Val Phe Pro Gln Ile Glu Ala Leu Ile Asn Lys
            20                  25                  30

Gly Ala Glu Val Arg Pro Val Thr His Thr Val Lys Ser Thr Asp
        35                  40                  45

Thr Arg Phe Gly Glu Gly Glu Trp Val Arg Ile Glu Glu Leu
    50                  55                  60

Thr Gly Phe Glu Val Ile Asp Ser Ile Pro Lys Ala Glu Pro Leu Gly
65                  70                  75                  80

Pro Lys Thr Pro Leu Asp Cys Met Val Val Ala Pro Leu Thr Gly Asn
                85                  90                  95

Ser Met Ser Lys Leu Ala Asn Ala Gln Thr Asp Ser Pro Val Leu Met
                100                 105                 110

Ala Ala Lys Ala Thr Met Arg Asn Ser Arg Pro Val Val Leu Gly Ile
            115                 120                 125

Ser Thr Asn Asp Ala Leu Gly Leu Asn Gly Val Asn Leu Met Arg Leu
    130                 135                 140

Met Ala Ala Lys Asn Val Tyr Phe Ile Pro Phe Gly Gln Asp Asp Pro
145                 150                 155                 160

Tyr Lys Lys Pro Asn Ser Leu Val Ala Lys Met Asp Leu Leu Val Pro
                165                 170                 175

Ala Val Glu Glu Ala Leu Ser His Lys Gln Ile Gln Pro Ile Leu Val
            180                 185                 190

His Asn Asp Gln
            195

<210> SEQ ID NO 46
<211> LENGTH: 196
<212> TYPE: PRT
<213> ORGANISM: Paenibacillus lautus

<400> SEQUENCE: 46

Met Asn Trp Asn Gly Ile Thr Val Gly Tyr Ala Leu Thr Gly Ser His
1               5                   10                  15

Cys Thr Leu Glu Glu Val Met Pro Gln Ile Gln Arg Phe Lys Asp Gly
            20                  25                  30

Gly Ala Asn Val Val Pro Ile Val Ser Ser Thr Ile Met Thr Thr Asp
        35                  40                  45

Thr Arg Phe Gly Thr Ser Glu Asn Trp Gln Lys Gln Leu Lys Asp Ile
    50                  55                  60

Thr Gly Asn Asp Ile Ile Ser Thr Ile Val Glu Ala Glu Pro Leu Gly
65                  70                  75                  80

Pro Ser Lys Leu Leu Asp Val Leu Val Ile Ala Pro Cys Thr Gly Asn
                85                  90                  95

Thr Thr Ser Lys Leu Ala Asn Ala Met Thr Asp Ser Pro Val Leu Met
                100                 105                 110

Ala Ala Lys Ala Gln Met Arg Asn Cys Arg Pro Leu Val Leu Ala Ile
            115                 120                 125

Ser Thr Asn Asp Gly Leu Gly Leu Asn Ala Ala Asn Ile Ala Lys Leu
    130                 135                 140

Leu Val Thr Lys Asn Ile Tyr Phe Val Pro Tyr Gly Gln Asp Asn Pro
145                 150                 155                 160
```

```
Gln Gln Lys Pro Asn Ser Leu Val Ala Lys Met Asn Leu Ile Pro Glu
                165                 170                 175

Ala Cys Tyr Ala Ala Leu Glu Gly Lys Gln Leu Gln Pro Met Ile Val
            180                 185                 190

Glu Tyr Ser Arg
        195

<210> SEQ ID NO 47
<211> LENGTH: 201
<212> TYPE: PRT
<213> ORGANISM: Oceanobacillus oncorhynchi

<400> SEQUENCE: 47

Met Thr Phe Lys Asn Lys Arg Ile Gly Phe Gly Leu Thr Gly Ser His
1               5                   10                  15

His Thr Leu Pro His Ile Phe Pro Ile Ile Glu Glu Leu Ile Glu Gln
            20                  25                  30

Gly Ala Glu Val Ile Pro Phe Ile Thr Glu Met Val Gln Tyr Thr Asp
        35                  40                  45

Thr Lys His Gly Lys Ala Ala Asp Asn Val Lys Arg Leu Glu Lys Ala
    50                  55                  60

Ala Asn His Pro Ile Ile Thr Ser Ile Pro Asp Ala Glu Pro Tyr Gly
65                  70                  75                  80

Pro Asp Lys Pro Leu Asp Val Met Val Ile Ala Pro Leu Thr Gly Asn
                85                  90                  95

Ser Met Ser Lys Leu Ala Asn Ala His Thr Asp Asn Pro Val Leu Met
            100                 105                 110

Ala Ala Lys Ser Thr Leu Arg Asn Glu His Pro Leu Leu Leu Ala Leu
        115                 120                 125

Thr Thr Asn Asp Ala Leu Gly Leu Asn Ala Lys Asn Leu Ala Val Leu
    130                 135                 140

Leu Asn Ala Lys His Ile Tyr Phe Val Pro Phe Gly Gln Asp Asn Pro
145                 150                 155                 160

His Gln Lys Pro Ser Ser Leu Ser Ala Asn Leu Asp Gln Leu Ile Pro
                165                 170                 175

Ala Ala Glu Ala Ala Leu Lys Gly Lys Gln Ile Gln Pro Ile Ile Val
            180                 185                 190

Pro Tyr Ser Thr Lys Asn Val Leu Lys
        195                 200

<210> SEQ ID NO 48
<211> LENGTH: 198
<212> TYPE: PRT
<213> ORGANISM: Bacillus amyloliquefaciens

<400> SEQUENCE: 48

Met Asn Trp Gln Gly Lys Thr Val Gly Tyr Ala Val Thr Gly Ser His
1               5                   10                  15

Cys Thr Leu Glu Glu Ile Met Pro Gln Val Lys Arg Phe Val Glu Ala
            20                  25                  30

Gly Ala Asn Val Val Pro Ile Ala Ser Gly Ser Val Gln Val Thr Asp
        35                  40                  45

Thr Arg Phe Gly Thr Ala Gln Asn Trp Leu Gln Gln Leu Lys Asp Ile
    50                  55                  60

Thr Gly Asn Asp Ile Ile Thr Thr Ile Val Glu Ala Glu Pro Leu Gly
65                  70                  75                  80
```

```
Pro Ser Lys Leu Leu Asp Val Leu Val Ile Ala Pro Cys Thr Gly Asn
            85                  90                  95

Thr Thr Ser Lys Leu Ala Asn Ala Met Thr Asp Ser Pro Val Leu Met
            100                 105                 110

Ala Ala Lys Ala Gln Met Arg Asn Gln Arg Pro Leu Val Leu Ala Ile
            115                 120                 125

Ser Thr Asn Asp Gly Leu Gly Leu Asn Ala Ser Asn Ile Ala Lys Leu
            130                 135                 140

Leu Ile Thr Lys Asn Ile Tyr Phe Val Pro Phe Gly Gln Asp Asn Pro
145                 150                 155                 160

Phe Gln Lys Pro Asn Ser Leu Val Ala Gln Met Asp Leu Ile Pro Glu
            165                 170                 175

Ala Cys Tyr Ala Ala Leu Glu Gly Lys Gln Leu Gln Pro Met Ile Leu
            180                 185                 190

Gln Arg Val Phe Ser Ala
            195

<210> SEQ ID NO 49
<211> LENGTH: 199
<212> TYPE: PRT
<213> ORGANISM: Bacillus sp.

<400> SEQUENCE: 49

Met Asn Leu Lys Gly Lys Lys Ile Gly Phe Gly Leu Thr Gly Ser His
1               5                   10                  15

Cys Thr Tyr Asp Ala Val Phe Pro Glu Ile Glu Lys Leu Val Gly Ala
            20                  25                  30

Gly Ala Glu Val Ile Pro Val Val Thr Phe Thr Val Gln Asn Thr Val
            35                  40                  45

Thr Arg Phe Gly Asp Gly Glu Asp Trp Ile Lys Arg Ile Glu Glu Val
            50                  55                  60

Thr Gly Asn Lys Val Ile Asp Ser Ile Val Lys Ala Glu Pro Leu Gly
65                  70                  75                  80

Pro Lys Ile Pro Leu Asp Cys Met Val Val Ala Pro Leu Thr Gly Asn
            85                  90                  95

Ser Met Ser Lys Phe Ala Asn Ala Met Thr Asp Ser Pro Val Leu Met
            100                 105                 110

Ala Ala Lys Ala Thr Leu Arg Asn Glu Lys Pro Val Val Leu Gly Ile
            115                 120                 125

Ser Thr Asn Asp Ala Leu Gly Leu Asn Gly Thr Asn Leu Met Arg Leu
            130                 135                 140

Met Ser Thr Lys Asn Ile Tyr Phe Ile Pro Phe Gly Gln Asp Asp Pro
145                 150                 155                 160

Val Lys Lys Pro Asn Ser Met Val Ala Arg Met Thr Ala Leu Ser Asp
            165                 170                 175

Thr Ile Val Lys Ala Ile Asn Gly Glu Gln Ile Gln Pro Val Ile Val
            180                 185                 190

Glu Arg Tyr Lys Asp Gly Asn
            195

<210> SEQ ID NO 50
<211> LENGTH: 198
<212> TYPE: PRT
<213> ORGANISM: Paenibacillus chibensis

<400> SEQUENCE: 50
```

Met Asn Trp Gln Gly Lys Thr Val Gly Tyr Ala Ile Thr Gly Ser His
1               5                   10                  15

Cys Thr Leu Glu Glu Ile Met Pro Gln Val Lys Arg Phe Val Asp Glu
                20                  25                  30

Gly Ala Lys Val Val Pro Ile Val Ser Asn Ser Val Gln Val Thr Asp
                35                  40                  45

Thr Arg Phe Gly Thr Ala Gln Asn Trp Leu Gln Gln Leu Lys Asp Ile
        50                  55                  60

Thr Gly Asn Asp Ile Ile Ser Ser Ile Val Asp Ala Glu Pro Leu Gly
65                  70                  75                  80

Pro Ser Lys Leu Leu Asp Val Leu Val Ile Ala Pro Cys Thr Gly Asn
                85                  90                  95

Thr Thr Ser Lys Leu Ala Asn Ala Met Thr Asp Thr Pro Val Leu Met
                100                 105                 110

Ala Ala Lys Ala Gln Met Arg Asn Leu Arg Pro Leu Val Leu Ala Ile
                115                 120                 125

Ser Thr Asn Asp Gly Leu Gly Leu Asn Ala Ala Asn Ile Ala Lys Leu
        130                 135                 140

Leu Val Thr Lys Asn Ile Tyr Phe Val Pro Phe Gly Gln Asp Asn Pro
145                 150                 155                 160

Leu Gln Lys Pro Asn Ser Leu Val Ala Gln Met Asp Leu Ile Pro Glu
                165                 170                 175

Ala Cys Tyr Ala Ala Leu Glu Gly Arg Gln Leu Gln Pro Met Ile Leu
                180                 185                 190

Gln Arg Ile Phe Ser Ala
        195

<210> SEQ ID NO 51
<211> LENGTH: 197
<212> TYPE: PRT
<213> ORGANISM: Bacillus flexus

<400> SEQUENCE: 51

Met Ser Leu Lys Gly Lys Arg Ile Gly Phe Gly Leu Thr Gly Ser His
1               5                   10                  15

Cys Thr Tyr Asp Ala Val Met Pro Glu Ile Glu Lys Leu Val Asn Leu
                20                  25                  30

Gly Ala Glu Val Met Pro Val Val Ser Tyr Thr Val Gln Ser Thr Asn
                35                  40                  45

Thr Arg Phe Gly Asp Gly Glu Asp Trp Ile Arg Lys Ile Glu Glu Val
        50                  55                  60

Thr Gly Asn Ser Val Ile Asn Thr Ile Val Lys Ala Glu Pro Leu Gly
65                  70                  75                  80

Pro Lys Ile Pro Leu Asp Cys Met Val Val Ala Pro Ile Thr Gly Asn
                85                  90                  95

Thr Met Ser Lys Phe Ala Asn Ala Met Thr Glu Ser Pro Val Leu Met
                100                 105                 110

Ala Ala Lys Ala Thr Leu Arg Asn Asn Lys Pro Val Val Leu Gly Ile
                115                 120                 125

Ser Thr Asn Asp Ala Leu Gly Leu Asn Gly Val Asn Leu Met Arg Leu
        130                 135                 140

Met Ala Thr Lys Asn Ile Tyr Phe Ile Pro Phe Gly Gln Asp Asp Pro
145                 150                 155                 160

Val Ser Lys Pro Asn Ser Met Val Ala Arg Met Pro Met Leu Ser Asp
                165                 170                 175

```
Thr Val Tyr Ala Ala Leu Glu Gly Lys Gln Ile Gln Pro Val Val Val
            180                 185                 190

Glu Arg Phe Arg Asp
        195

<210> SEQ ID NO 52
<211> LENGTH: 199
<212> TYPE: PRT
<213> ORGANISM: Bacillus firmus

<400> SEQUENCE: 52

Met Ser Leu Lys Gly Lys Arg Ile Gly Phe Gly Leu Thr Gly Ser His
1               5                   10                  15

Cys Thr Tyr Asp Ala Val Phe Pro Glu Ile Glu Arg Leu Val Leu Ala
            20                  25                  30

Gly Ala Glu Val Leu Pro Val Val Thr Phe Thr Val Lys Ser Thr Glu
        35                  40                  45

Thr Arg Phe Gly Lys Gly Glu Asp Trp Val Gln Arg Ile Glu Asp Leu
    50                  55                  60

Thr Gly Asn Lys Val Ile Asp Ser Ile Val Lys Ala Glu Pro Leu Gly
65                  70                  75                  80

Pro Lys Ile Pro Leu Asp Cys Met Val Ile Ala Pro Leu Thr Gly Asn
                85                  90                  95

Thr Met Ser Lys Phe Ala Asn Ala Met Thr Asp Ser Pro Val Leu Met
            100                 105                 110

Ala Ala Lys Ala Thr Leu Arg Asn Gly Lys Pro Val Val Leu Gly Ile
        115                 120                 125

Ser Thr Asn Asp Ala Leu Gly Leu Asn Gly Val Asn Leu Met Arg Leu
    130                 135                 140

Met Ala Thr Lys Asn Ile Tyr Phe Ile Pro Tyr Gly Gln Asp Asp Pro
145                 150                 155                 160

Val Lys Lys Pro Asn Ser Met Val Ala Arg Met Thr Ala Leu Tyr Asp
                165                 170                 175

Thr Val Ile His Ala Met Glu Gly Lys Gln Leu Gln Pro Val Leu Val
            180                 185                 190

Glu Arg Tyr Lys Asp Glu Ser
        195

<210> SEQ ID NO 53
<211> LENGTH: 196
<212> TYPE: PRT
<213> ORGANISM: Virgibacillus halophilus

<400> SEQUENCE: 53

Met Ser Leu Asp Gly Lys Arg Ile Gly Phe Gly Leu Thr Ala Ser His
1               5                   10                  15

Cys Thr Tyr Glu Ala Val Phe Pro Glu Met Glu Arg Leu Ile Asn Met
            20                  25                  30

Gly Ala Glu Val Val Pro Val Val Thr Tyr Asn Val Lys Asn Val Asp
        35                  40                  45

Thr Lys Phe Gly Lys Ala Ser Asp His Ile Lys Arg Leu Glu Glu Ile
    50                  55                  60

Thr Asn Lys Glu Val Val Ala Thr Ile Pro Asp Ala Glu Pro Leu Gly
65                  70                  75                  80

Pro Ile Thr Pro Leu Asp Cys Met Val Ile Ala Pro Leu Thr Gly Asn
                85                  90                  95
```

```
Ser Met Ser Arg Leu Ala Asn Ala Ile Thr Asp Ser Pro Pro Leu Met
            100                 105                 110

Ala Ala Lys Ala Thr Met Arg Asn Gln Asn Pro Val Val Leu Gly Ile
        115                 120                 125

Ser Thr Asn Asp Ala Leu Gly Leu Asn Gly Val Asn Leu Met Lys Leu
    130                 135                 140

Met Ala Ser Lys Met Ile Tyr Phe Ile Pro Phe Gly Gln Asp Asp Pro
145                 150                 155                 160

Val Lys Lys Pro Asn Ser Leu Val Ser Asp Met Thr Leu Leu Pro Glu
                165                 170                 175

Thr Ile Glu Ser Ala Leu Asn Gly Asn Gln Leu Gln Pro Val Leu Ile
            180                 185                 190

Pro Phe Gln Ser
        195

<210> SEQ ID NO 54
<211> LENGTH: 198
<212> TYPE: PRT
<213> ORGANISM: Paenibacillus azoreducens

<400> SEQUENCE: 54

Met Asn Trp Gln Gly Lys Thr Val Gly Tyr Ala Ile Thr Gly Ser His
1               5                   10                  15

Cys Thr Leu Glu Glu Ile Met Pro Gln Val Lys Arg Phe Val Asp Glu
            20                  25                  30

Gly Ala Lys Val Val Pro Ile Val Ser Asn Thr Val Gln Val Thr Asp
        35                  40                  45

Thr Arg Phe Gly Thr Ala His Asn Trp Leu Gln Arg Leu Lys Asp Ile
    50                  55                  60

Thr Gly Ser Glu Leu Ile Ser Thr Ile Val Glu Ala Glu Pro Leu Gly
65                  70                  75                  80

Pro Ser Lys Leu Leu Asp Val Leu Val Ile Ala Pro Cys Thr Gly Asn
                85                  90                  95

Thr Thr Ser Lys Leu Ala Asn Ala Ile Thr Asp Ser Pro Val Leu Met
            100                 105                 110

Ala Ala Lys Ala Gln Met Arg Asn Leu Arg Pro Leu Val Leu Ala Ile
        115                 120                 125

Ser Thr Asn Asp Gly Leu Gly Leu Asn Ala Ala Asn Ile Ala Lys Leu
    130                 135                 140

Leu Val Ala Lys Asn Ile Tyr Phe Val Pro Phe Gly Gln Asp Asn Pro
145                 150                 155                 160

His Gln Lys Pro Asn Ser Leu Val Ala Gln Met Asp Leu Ile Pro Glu
                165                 170                 175

Ala Cys Tyr Ala Ala Leu Glu Gly Arg Gln Leu Gln Pro Met Leu Leu
            180                 185                 190

Gln Arg Ile Phe Ser Ala
        195

<210> SEQ ID NO 55
<211> LENGTH: 202
<212> TYPE: PRT
<213> ORGANISM: Artificial Sequence
<220> FEATURE:
<223> OTHER INFORMATION: DpaB consensus sequence
<220> FEATURE:
<221> NAME/KEY: MISC_FEATURE
<222> LOCATION: (3)..(4)
```

```
<223> OTHER INFORMATION: X is any amino acid
<220> FEATURE:
<221> NAME/KEY: MISC_FEATURE
<222> LOCATION: (21)..(22)
<223> OTHER INFORMATION: X is any amino acid
<220> FEATURE:
<221> NAME/KEY: MISC_FEATURE
<222> LOCATION: (24)..(24)
<223> OTHER INFORMATION: X is any amino acid
<220> FEATURE:
<221> NAME/KEY: MISC_FEATURE
<222> LOCATION: (26)..(26)
<223> OTHER INFORMATION: X is any amino acid
<220> FEATURE:
<221> NAME/KEY: MISC_FEATURE
<222> LOCATION: (29)..(29)
<223> OTHER INFORMATION: X is any amino acid
<220> FEATURE:
<221> NAME/KEY: MISC_FEATURE
<222> LOCATION: (32)..(33)
<223> OTHER INFORMATION: X is any amino acid
<220> FEATURE:
<221> NAME/KEY: MISC_FEATURE
<222> LOCATION: (38)..(38)
<223> OTHER INFORMATION: X is any amino acid
<220> FEATURE:
<221> NAME/KEY: MISC_FEATURE
<222> LOCATION: (40)..(40)
<223> OTHER INFORMATION: X is any amino acid
<220> FEATURE:
<221> NAME/KEY: MISC_FEATURE
<222> LOCATION: (42)..(43)
<223> OTHER INFORMATION: X is any amino acid
<220> FEATURE:
<221> NAME/KEY: MISC_FEATURE
<222> LOCATION: (47)..(47)
<223> OTHER INFORMATION: X is any amino acid
<220> FEATURE:
<221> NAME/KEY: MISC_FEATURE
<222> LOCATION: (54)..(57)
<223> OTHER INFORMATION: X is any amino acid
<220> FEATURE:
<221> NAME/KEY: MISC_FEATURE
<222> LOCATION: (59)..(62)
<223> OTHER INFORMATION: X is any amino acid
<220> FEATURE:
<221> NAME/KEY: MISC_FEATURE
<222> LOCATION: (64)..(65)
<223> OTHER INFORMATION: X is any amino acid
<220> FEATURE:
<221> NAME/KEY: MISC_FEATURE
<222> LOCATION: (68)..(70)
<223> OTHER INFORMATION: X is any amino acid
<220> FEATURE:
<221> NAME/KEY: MISC_FEATURE
<222> LOCATION: (72)..(73)
<223> OTHER INFORMATION: X is any amino acid
<220> FEATURE:
<221> NAME/KEY: MISC_FEATURE
<222> LOCATION: (76)..(76)
<223> OTHER INFORMATION: X is any amino acid
<220> FEATURE:
<221> NAME/KEY: MISC_FEATURE
<222> LOCATION: (83)..(84)
<223> OTHER INFORMATION: X is any amino acid
<220> FEATURE:
<221> NAME/KEY: MISC_FEATURE
<222> LOCATION: (94)..(94)
<223> OTHER INFORMATION: X is any amino acid
<220> FEATURE:
<221> NAME/KEY: MISC_FEATURE
<222> LOCATION: (98)..(98)
<223> OTHER INFORMATION: X is any amino acid
<220> FEATURE:
<221> NAME/KEY: MISC_FEATURE
<222> LOCATION: (119)..(119)
<223> OTHER INFORMATION: X is any amino acid
<220> FEATURE:
<221> NAME/KEY: MISC_FEATURE
```

-continued

```
<222> LOCATION: (122)..(123)
<223> OTHER INFORMATION: X is any amino acid
<220> FEATURE:
<221> NAME/KEY: MISC_FEATURE
<222> LOCATION: (128)..(128)
<223> OTHER INFORMATION: X is any amino acid
<220> FEATURE:
<221> NAME/KEY: MISC_FEATURE
<222> LOCATION: (139)..(140)
<223> OTHER INFORMATION: X is any amino acid
<220> FEATURE:
<221> NAME/KEY: MISC_FEATURE
<222> LOCATION: (143)..(144)
<223> OTHER INFORMATION: X is any amino acid
<220> FEATURE:
<221> NAME/KEY: misc_feature
<222> LOCATION: (146)..(147)
<223> OTHER INFORMATION: Xaa can be any naturally occurring amino acid
<220> FEATURE:
<221> NAME/KEY: MISC_FEATURE
<222> LOCATION: (154)..(154)
<223> OTHER INFORMATION: X is any amino acid
<220> FEATURE:
<221> NAME/KEY: MISC_FEATURE
<222> LOCATION: (162)..(163)
<223> OTHER INFORMATION: X is any amino acid
<220> FEATURE:
<221> NAME/KEY: MISC_FEATURE
<222> LOCATION: (171)..(171)
<223> OTHER INFORMATION: X is any amino acid
<220> FEATURE:
<221> NAME/KEY: MISC_FEATURE
<222> LOCATION: (173)..(173)
<223> OTHER INFORMATION: X is any amino acid
<220> FEATURE:
<221> NAME/KEY: MISC_FEATURE
<222> LOCATION: (176)..(181)
<223> OTHER INFORMATION: X is any amino acid
<220> FEATURE:
<221> NAME/KEY: MISC_FEATURE
<222> LOCATION: (184)..(184)
<223> OTHER INFORMATION: X is any amino acid
<220> FEATURE:
<221> NAME/KEY: MISC_FEATURE
<222> LOCATION: (186)..(186)
<223> OTHER INFORMATION: X is any amino acid
<220> FEATURE:
<221> NAME/KEY: MISC_FEATURE
<222> LOCATION: (188)..(188)
<223> OTHER INFORMATION: X is any amino acid
<220> FEATURE:
<221> NAME/KEY: MISC_FEATURE
<222> LOCATION: (191)..(192)
<223> OTHER INFORMATION: X is any amino acid
<220> FEATURE:
<221> NAME/KEY: MISC_FEATURE
<222> LOCATION: (194)..(202)
<223> OTHER INFORMATION: X is any amino acid

<400> SEQUENCE: 55

Met Met Xaa Xaa Lys Gly Lys Arg Ile Gly Phe Gly Leu Thr Gly Ser
1               5                   10                  15

His Cys Thr Tyr Xaa Xaa Val Xaa Pro Xaa Ile Glu Xaa Leu Val Xaa
            20                  25                  30

Xaa Gly Ala Glu Val Xaa Pro Xaa Val Xaa Thr Val Gln Xaa Thr
        35                  40                  45

Asp Thr Arg Phe Gly Xaa Xaa Xaa Xaa Trp Xaa Xaa Xaa Xaa Glu Xaa
    50                  55                  60

Xaa Thr Gly Xaa Xaa Xaa Ile Xaa Xaa Ile Val Xaa Ala Glu Pro Leu
65                  70                  75                  80

Gly Pro Xaa Xaa Pro Leu Asp Cys Met Val Ile Ala Pro Xaa Thr Gly
                85                  90                  95
```

```
Asn Xaa Met Ser Lys Leu Ala Asn Ala Met Thr Asp Ser Pro Val Leu
            100                 105                 110

Met Ala Ala Lys Ala Thr Xaa Arg Asn Xaa Xaa Pro Val Val Leu Xaa
            115                 120                 125

Ile Ser Thr Asn Asp Ala Leu Gly Leu Asn Xaa Xaa Asn Leu Xaa Xaa
            130                 135                 140

Leu Xaa Xaa Thr Lys Asn Ile Tyr Phe Xaa Pro Phe Gly Gln Asp Asp
145                 150                 155                 160

Pro Xaa Xaa Lys Pro Asn Ser Leu Val Ala Xaa Met Xaa Leu Leu Xaa
                165                 170                 175

Xaa Xaa Xaa Xaa Xaa Ala Leu Xaa Gly Xaa Gln Xaa Gln Pro Xaa Xaa
            180                 185                 190

Val Xaa Xaa Xaa Xaa Xaa Xaa Xaa Xaa
            195                 200

<210> SEQ ID NO 56
<211> LENGTH: 196
<212> TYPE: PRT
<213> ORGANISM: Artificial Sequence
<220> FEATURE:
<223> OTHER INFORMATION: DpaB consensus sequence

<400> SEQUENCE: 56

Met Ser Leu Lys Gly Lys Arg Ile Gly Phe Gly Leu Thr Gly Ser His
1               5                   10                  15

Cys Thr Tyr Asp Glu Val Met Pro Glu Ile Glu Lys Leu Val Asp Glu
            20                  25                  30

Gly Ala Glu Val Thr Pro Ile Val Ser Tyr Thr Val Gln Thr Thr Asp
            35                  40                  45

Thr Arg Phe Gly Lys Ala Glu Glu Trp Ile Lys Lys Ile Glu Glu Ile
        50                  55                  60

Thr Gly Asn Lys Val Ile Asn Thr Ile Val Glu Ala Glu Pro Leu Gly
65                  70                  75                  80

Pro Lys Lys Leu Leu Asp Cys Met Val Ile Ala Pro Cys Thr Gly Asn
                85                  90                  95

Thr Met Ala Lys Leu Ala Asn Ala Ile Thr Asp Ser Pro Val Leu Met
            100                 105                 110

Ala Ala Lys Ala Thr Leu Arg Asn Gln Arg Pro Val Val Leu Ala Ile
            115                 120                 125

Ser Thr Asn Asp Ala Leu Gly Leu Asn Ala Lys Asn Leu Gly Arg Leu
            130                 135                 140

Leu Asn Thr Lys Asn Ile Tyr Phe Val Pro Phe Gly Gln Asp Asp Pro
145                 150                 155                 160

Val Lys Lys Pro Asn Ser Leu Val Ala Arg Met Asp Leu Leu Ile Asp
                165                 170                 175

Thr Val Glu Glu Ala Leu Glu Gly Lys Gln Leu Gln Pro Val Leu Ile
            180                 185                 190

Glu Tyr Phe Arg
        195

<210> SEQ ID NO 57
<211> LENGTH: 218
<212> TYPE: PRT
<213> ORGANISM: Clostridium beijerinckii

<400> SEQUENCE: 57

Met Lys Ile Tyr Gly Ile Asn Gly Ser Pro Arg Lys Asn Lys Asn Thr
```

```
1               5                   10                  15

Ala Thr Leu Leu Gln Lys Ala Leu Asp Gly Val Lys Glu Ala Ala Lys
            20                  25                  30

Asp Lys Glu Ile Glu Thr Glu Ile Ile Asn Leu Tyr Asp Leu Asn Tyr
        35                  40                  45

Thr Gly Cys Ile Ser Cys Phe Ala Cys Lys Arg Leu Gly Ser Asn Ser
    50                  55                  60

Tyr Gly Lys Cys Ala Val Lys Asp Asp Leu Gln Glu Val Leu Glu Lys
65                  70                  75                  80

Val Ser Gln Ser Asp Gly Leu Ile Phe Ser Ser Pro Val Tyr Phe Ser
                85                  90                  95

Asn Val Thr Gly Lys Phe Leu Ser Phe Leu Glu Arg Leu Leu Phe Pro
            100                 105                 110

Tyr Leu Val Tyr Asp Asn Asn Gly Thr Ser Leu Ala Pro Lys Arg Met
        115                 120                 125

Pro Thr Ala Phe Ile Tyr Thr Met Asn Val Lys Glu Glu Val Met Lys
    130                 135                 140

Gln Ile Gly Tyr Leu Lys Thr Phe Glu Arg Met Glu Ser Asn Ile Gly
145                 150                 155                 160

His Ile Phe Thr Lys Pro Leu Val Met Tyr Ser Asn Asn Thr Tyr Gln
                165                 170                 175

Phe Asp Asp Tyr Ser Lys Tyr Lys Val Glu Ser Phe Ser Glu Glu Glu
            180                 185                 190

Lys Ala Ala His Arg Lys Ile Gln Phe Pro Leu Asp Cys Gln Lys Ala
        195                 200                 205

Phe Glu Leu Gly Ala Asn Leu Ile Lys His
    210                 215
```

<210> SEQ ID NO 58
<211> LENGTH: 193
<212> TYPE: PRT
<213> ORGANISM: Clostridium beijerinckii

<400> SEQUENCE: 58

```
Met Ser Lys Val Val Ile Phe Asn Gly Ser Pro Arg Lys Asn Gly Tyr
1               5                   10                  15

Thr Thr Lys Leu Leu Glu Gln Val Ala Lys Gly Ala Lys Ser Lys Gly
            20                  25                  30

Ala Glu Ile Ile Glu Phe Asp Leu Asn Asp Ser Gly Ile Arg Gly Cys
        35                  40                  45

Gln Gly Cys Phe Tyr Cys Arg Thr His Asp Gly Cys Ala Val Lys Asp
    50                  55                  60

Tyr Leu Gln Pro Met Tyr Lys Ala Ile Thr Glu Ala Asp Ala Ile Val
65                  70                  75                  80

Phe Gly Ser Pro Ile Tyr Tyr Tyr Gln Ile Thr Gly Gln Ala Lys Ile
                85                  90                  95

Trp Leu Asp Arg Thr Phe Pro Met Val Gly Asp Asn Phe Ala Pro Arg
            100                 105                 110

His Ser Gly Lys Lys Leu Ile Thr Ile Phe Thr Gln Gly Ser Gln Asn
        115                 120                 125

Pro Glu Met Gly Ala Glu Gly Ile Lys Phe Val Asn Asn Met Leu Ala
    130                 135                 140

Ala Tyr Gly Trp Lys Leu Glu Asp Ser Ile Leu Cys Cys Gly Thr Thr
145                 150                 155                 160
```

```
Asn Phe His Ser Glu Lys Leu Gly Arg Tyr Asp Ser Asn Leu Glu Gln
                165                 170                 175

Phe Glu Glu Leu Ser Leu Arg Ala Phe Lys Asp Gly Asn Leu Val
            180                 185                 190

Arg

<210> SEQ ID NO 59
<211> LENGTH: 183
<212> TYPE: PRT
<213> ORGANISM: Clostridium beijerinckii

<400> SEQUENCE: 59

Met Ser Lys Val Val Ile Phe Lys Gly Ser Pro Arg Lys Asn Gly Tyr
1               5                   10                  15

Thr Ala Arg Leu Leu Glu Gln Val Ala Lys Gly Ala Lys Ser Lys Gly
                20                  25                  30

Ala Glu Val Ile Glu Phe Asp Leu Asn Asp Ser Gly Ile Arg Gly Cys
            35                  40                  45

Gln Gly Cys Met Tyr Cys Arg Thr His Asp Gly Cys Ala Val Asn Asp
    50                  55                  60

Tyr Leu Gln Pro Met Tyr Ala Ala Ile Lys Glu Ala Asp Ala Ile Val
65                  70                  75                  80

Phe Gly Ser Pro Ile Tyr Tyr Tyr Thr Ile Thr Gly Gln Ser Lys Val
                85                  90                  95

Trp Phe Asp Arg Thr Phe Pro Met Ile Gly Asn Asp Tyr Lys Ala Lys
                100                 105                 110

Tyr Pro Gly Lys Lys Leu Ile Thr Ile Phe Thr Gln Gly Asn Pro Asp
            115                 120                 125

Pro Lys Ile Gly Ala Glu Gly Val Lys Phe Ala Asn Asn Met Leu Glu
    130                 135                 140

Glu Leu Gly Trp Lys Leu Glu Asp Ser Ile His Tyr Cys Gly Thr Ser
145                 150                 155                 160

His Asn Pro Asp Leu Ala Met Phe Asp Glu Leu Ser Leu Arg Ala Phe
                165                 170                 175

Lys Asp Gly Glu Asn Leu Ala
            180

<210> SEQ ID NO 60
<211> LENGTH: 182
<212> TYPE: PRT
<213> ORGANISM: Clostridium beijerinckii

<400> SEQUENCE: 60

Met Ser Lys Val Val Ile Phe Lys Gly Ser Pro Arg Lys Asn Gly Tyr
1               5                   10                  15

Thr Thr Lys Leu Leu Asp Gln Val Ala Lys Gly Ala Lys Ser Lys Gly
                20                  25                  30

Ala Glu Val Ile Glu Phe Asp Leu Asn Asp Thr Gly Ile Arg Gly Cys
            35                  40                  45

Gln Gly Cys Phe Tyr Cys Arg Thr His Asp Gly Cys Ala Val Asn Asp
    50                  55                  60

Tyr Leu Gln Pro Met Tyr Lys Ala Ile Ala Glu Ala Asp Ala Ile Val
65                  70                  75                  80

Phe Gly Ser Pro Ile Tyr Met Phe Gln Ile Thr Ser Gln Ala Lys Thr
                85                  90                  95

Cys Leu Asp Arg Thr Phe Pro Met Val Glu Glu Leu Pro Asn Lys Phe
```

```
                100                 105                 110
Ile Pro Arg His Pro Gly Lys Lys Leu Ile Thr Val Phe Ala Gln Gly
            115                 120                 125

Ser Leu Asp Pro Lys Lys Gly Ala Glu Ala Ile Lys Tyr Val Asn Asn
            130                 135                 140

Ile Phe Asp Val Phe Gly Trp Lys Leu Glu Asp Cys Ile His Tyr Cys
145                 150                 155                 160

Gly Thr Asp Asp Glu Val Phe Asn Glu Leu Ser Leu Arg Ala Phe Lys
                165                 170                 175

Asp Gly Glu Asn Leu Ala
            180

<210> SEQ ID NO 61
<211> LENGTH: 193
<212> TYPE: PRT
<213> ORGANISM: Clostridium beijerinckii

<400> SEQUENCE: 61

Met Asn Ile Ile Gly Ile Ser Ala Ser Ser Arg Lys Glu Gly Asn Thr
1               5                   10                  15

Ala Trp Ile Val Asn Lys Ile Leu Glu Gly Ala Lys Glu Gln Gly Ala
            20                  25                  30

Glu Thr Gln Tyr Phe Asp Phe Asn Asn Leu Asp Ile Lys Pro Cys Gln
        35                  40                  45

Gly Cys Trp Ala Cys His Lys Gly Asp Gln Gly Cys Val Ile Lys Asp
    50                  55                  60

Asp Met Gln Lys Leu Asn Asp Ala Ile Asp Arg Ala Asn Val Ile Val
65                  70                  75                  80

Phe Gly Ser Pro Ile Tyr Met Met Gln Met Ser Ala Gln Gly Lys Ile
                85                  90                  95

Ile Ile Asp Arg Met Phe Ala Arg Phe Ser Pro Arg Tyr Ser Pro Tyr
            100                 105                 110

Phe Lys Glu Glu Ser Ala Ala Glu Lys Arg Leu Val Leu Thr Phe Asn
        115                 120                 125

Gln Gly Asn Pro Asp Pro Glu Leu Phe Lys Ser Tyr Ile Asp Tyr Thr
    130                 135                 140

Lys His Met Phe Glu Leu Leu Glu Phe Asp Val Thr Glu Val Pro Val
145                 150                 155                 160

Val Thr Gly Leu Arg Asn Gly Pro Ala Asn Glu Arg Glu Asp Leu Asn
                165                 170                 175

Ile Met Leu Lys Asp Val Gly Lys Thr Ile Val Ser Gly Ile Ser
            180                 185                 190

Lys

<210> SEQ ID NO 62
<211> LENGTH: 208
<212> TYPE: PRT
<213> ORGANISM: Clostridium beijerinckii

<400> SEQUENCE: 62

Met Lys Val Leu Leu Ile Asn Gly Ser Pro Lys Ala Lys Gly Cys Thr
1               5                   10                  15

Tyr Thr Thr Leu Cys Glu Val Ala Asp Glu Leu Glu Lys Glu Asn Ile
            20                  25                  30

Glu Thr Glu Ile Phe Gln Ile Gly Asn Lys Pro Ile Ser Gly Cys Ile
        35                  40                  45
```

```
Asp Cys Gly Cys Tyr Lys Ser Gly Glu Gly Lys Cys Val Phe Ser
 50                  55                  60

Asp Asp Ile Val Asn Ile Ala Leu Glu Lys Ala Lys Glu Ala Asp Gly
65                  70                  75                  80

Phe Ile Phe Gly Ser Pro Val His Tyr Ala Ala Pro Ser Gly Ser Ile
                 85                  90                  95

Thr Ser Phe Leu Asp Arg Phe Phe Tyr Ala Gly Asn Cys Phe Ala His
                100                 105                 110

Lys Pro Gly Ala Ala Val Val Ser Cys Arg Arg Gly Gly Ala Ala Ser
                115                 120                 125

Ala Phe Asp Gln Leu Asn Lys Tyr Phe Thr Ile Ser Asn Met Pro Val
    130                 135                 140

Val Ser Ser Gln Tyr Trp Asn Met Val His Gly Asn Thr Pro Glu Glu
145                 150                 155                 160

Val Lys Gln Asp Leu Glu Gly Met Gln Thr Met Arg Met Leu Gly Lys
                165                 170                 175

Asn Met Ala Trp Leu Leu Lys Ser Ile Asp Ala Gly Lys Lys Ala Gly
                180                 185                 190

Ile Ser Leu Pro Glu Ser Glu Pro Arg Val Ala Thr Asn Phe Ile Arg
        195                 200                 205
```

<210> SEQ ID NO 63
<211> LENGTH: 201
<212> TYPE: PRT
<213> ORGANISM: Archaeoglobus fulgidus

<400> SEQUENCE: 63

```
Met Lys Leu Leu Ala Ile Asn Gly Ser Pro Asn Lys Arg Asn Thr Leu
1               5                   10                  15

Phe Leu Leu Glu Val Ile Ala Glu Glu Val Lys Lys Leu Gly His Glu
                20                  25                  30

Ala Glu Ile Ile His Leu Lys Asp Tyr Glu Ile Lys Glu Cys Lys Gly
            35                  40                  45

Cys Asp Ala Cys Leu Lys Gly Asp Cys Ser Gln Lys Asp Asp Ile Tyr
 50                 55                  60

Lys Val Leu Glu Lys Met Gln Glu Ala Asp Ala Ile Val Ile Gly Thr
65                  70                  75                  80

Pro Thr Tyr Phe Gly Asn Val Thr Gly Ile Val Lys Asn Leu Ile Asp
                85                  90                  95

Arg Ser Arg Met Ala Arg Met Gly Asn Tyr Arg Leu Arg Asn Arg Val
                100                 105                 110

Phe Ala Pro Val Val Thr Ser Gly Leu Arg Asn Gly Gly Ala Glu Tyr
            115                 120                 125

Ala Ala Met Ser Leu Ile Val Tyr Ala Leu Gly Gln Ala Met Leu Pro
    130                 135                 140

Val Ser Ile Val Glu Asn Pro Ile Thr Thr Gly Thr Phe Pro Val Gly
145                 150                 155                 160

Val Ile Gln Gly Asp Ala Gly Trp Arg Ser Val Lys Lys Asp Glu Ile
                165                 170                 175

Ala Ile Asn Ser Ala Lys Ala Leu Ala Lys Arg Ile Val Glu Val Ala
                180                 185                 190

Glu Ala Thr Lys Asn Leu Arg Glu Ser
        195                 200
```

-continued

```
<210> SEQ ID NO 64
<211> LENGTH: 193
<212> TYPE: PRT
<213> ORGANISM: Methanocaldococcus jannaschii,

<400> SEQUENCE: 64
```

| Met | Lys | Val | Ile | Gly | Ile | Ser | Gly | Ser | Pro | Arg | Pro | Glu | Gly | Asn | Thr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Thr | Leu | Val | Arg | Glu | Ala | Leu | Asn | Ala | Ile | Ala | Glu | Glu | Gly | Ile |
|-----|-----|-----|-----|-----|-----|-----|-----|-----|-----|-----|-----|-----|-----|-----|
|     |     | 20  |     |     |     |     | 25  |     |     |     |     | 30  |     |     |

| Glu | Thr | Glu | Phe | Ile | Ser | Leu | Ala | Asp | Lys | Glu | Leu | Asn | Pro | Cys | Ile |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Gly | Cys | Asn | Met | Cys | Lys | Glu | Glu | Gly | Lys | Cys | Pro | Ile | Ile | Asp | Asp |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Val | Asp | Glu | Ile | Leu | Lys | Lys | Met | Lys | Glu | Ala | Asp | Gly | Ile | Ile | Leu |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Gly | Ser | Pro | Val | Tyr | Phe | Gly | Gly | Val | Ser | Ala | Gln | Leu | Lys | Met | Leu |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Met | Asp | Arg | Ser | Arg | Pro | Leu | Arg | Ile | Gly | Phe | Gln | Leu | Arg | Asn | Lys |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Val | Gly | Gly | Ala | Val | Ala | Val | Gly | Ala | Ser | Arg | Asn | Gly | Gly | Gln | Glu |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Thr | Thr | Ile | Gln | Gln | Ile | His | Asn | Phe | Phe | Leu | Ile | His | Ser | Met | Ile |
|-----|-----|-----|-----|-----|-----|-----|-----|-----|-----|-----|-----|-----|-----|-----|-----|
| 130 |     |     |     |     | 135 |     |     |     |     | 140 |     |     |     |     |     |

| Val | Val | Gly | Asp | Asn | Asp | Pro | Thr | Ala | His | Tyr | Gly | Gly | Thr | Gly | Val |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Gly | Lys | Ala | Pro | Gly | Asp | Cys | Lys | Asn | Asp | Asp | Ile | Gly | Leu | Glu | Thr |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Ala | Arg | Asn | Leu | Gly | Lys | Lys | Val | Ala | Glu | Val | Val | Lys | Leu | Ile | Lys |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

Lys

```
<210> SEQ ID NO 65
<211> LENGTH: 225
<212> TYPE: PRT
<213> ORGANISM: Peptoclostridium difficile

<400> SEQUENCE: 65
```

| Met | Ile | Ile | Thr | Val | Ile | Asn | Gly | Ser | Pro | Arg | Lys | Asn | Gly | Ala | Thr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Lys | Val | Leu | Thr | Tyr | Leu | Tyr | Lys | Asp | Ile | Glu | Arg | Leu | Ile | Pro |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Asp | Val | Lys | Ile | Asn | Tyr | Phe | Asp | Leu | Ser | Glu | Val | Asn | Pro | Ser | Tyr |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Cys | Ile | Gly | Cys | Leu | Asn | Cys | Tyr | Lys | Met | Gly | Lys | Cys | Ile | Asn | Gln |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Asn | Asp | Lys | Val | Glu | Tyr | Ile | His | Asp | Ile | Ile | Thr | Lys | Ser | Asp | Gly |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Val | Ile | Phe | Gly | Ser | Pro | Thr | Tyr | Gly | Ser | Ser | Val | Thr | Gly | Leu | Phe |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Lys | Val | Phe | Thr | Asp | Arg | Ala | His | Met | Met | Leu | Glu | Arg | Leu | Leu | Tyr |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Arg | Lys | Pro | Cys | Ile | Ala | Val | Thr | Thr | Tyr | Glu | Asn | Ala | Arg | Gly | Ser |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Lys | Ala | Ile | Ser | Phe | Ile | Lys | Ser | Met | Val | Leu | Asp | Ser | Gly | Gly | Tyr |
|-----|-----|-----|-----|-----|-----|-----|-----|-----|-----|-----|-----|-----|-----|-----|-----|
| 130 |     |     |     |     | 135 |     |     |     |     | 140 |     |     |     |     |     |

```
Val Cys Gly Ser Leu Ser Ile Lys Thr Gly Phe Asn Gln Asn Pro Ile
145                 150                 155                 160

Thr Glu Lys Val Glu Ser Lys Ile Gln Lys Val Ser Lys Lys Phe Ile
                165                 170                 175

Tyr Cys Ile Glu Glu Lys Lys Asn Pro Pro Val Leu Ser Gln Ile Tyr
            180                 185                 190

Asn Phe Ile Ala Ile Asn Ala Val Leu Lys Pro Met Ala Phe Lys Asp
        195                 200                 205

Ile Glu Gln Tyr Lys Gly Ile Ile Asp Arg Trp Glu Gln Gly Ile
    210                 215                 220

Ile
225

<210> SEQ ID NO 66
<211> LENGTH: 191
<212> TYPE: PRT
<213> ORGANISM: Methanosarcina thermophila

<400> SEQUENCE: 66

Met Lys Ile Thr Gly Ile Ser Gly Ser Pro Arg Lys Gly Gln Asn Cys
1               5                   10                  15

Glu Lys Ile Ile Gly Ala Ala Leu Glu Val Ala Lys Glu Arg Gly Phe
                20                  25                  30

Glu Thr Asp Thr Val Phe Ile Ser Asn Glu Glu Val Ala Pro Cys Lys
            35                  40                  45

Ala Cys Gly Ala Cys Arg Asp Gln Asp Phe Cys Val Ile Asp Asp Asp
        50                  55                  60

Met Asp Glu Ile Tyr Glu Lys Met Arg Ala Ala Asp Gly Ile Ile Val
65                  70                  75                  80

Ala Ala Pro Val Tyr Met Gly Asn Tyr Pro Ala Gln Leu Lys Ala Leu
                85                  90                  95

Phe Asp Arg Ser Val Leu Leu Arg Lys Asn Phe Ala Leu Lys Asn
            100                 105                 110

Lys Val Gly Ala Ala Leu Ser Val Gly Gly Ser Arg Asn Gly Gly Gln
        115                 120                 125

Glu Lys Thr Ile Gln Ser Ile His Asp Trp Met His Ile His Gly Met
    130                 135                 140

Ile Val Val Gly Asp Asn Ser His Phe Gly Gly Ile Thr Trp Asn Pro
145                 150                 155                 160

Ala Glu Glu Asp Thr Val Gly Met Gln Thr Val Ser Glu Thr Ala Lys
                165                 170                 175

Lys Leu Cys Asp Val Leu Glu Leu Ile Gln Lys Asn Arg Asp Lys
            180                 185                 190

<210> SEQ ID NO 67
<211> LENGTH: 289
<212> TYPE: PRT
<213> ORGANISM: Artificial Sequence
<220> FEATURE:
<223> OTHER INFORMATION: Consensus Isf sequence
<220> FEATURE:
<221> NAME/KEY: MISC_FEATURE
<222> LOCATION: (4)..(6)
<223> OTHER INFORMATION: X is any amino acid
<220> FEATURE:
<221> NAME/KEY: MISC_FEATURE
<222> LOCATION: (8)..(8)
<223> OTHER INFORMATION: X is any amino acid
<220> FEATURE:
```

```
<221> NAME/KEY: MISC_FEATURE
<222> LOCATION: (14)..(14)
<223> OTHER INFORMATION: X is any amino acid
<220> FEATURE:
<221> NAME/KEY: MISC_FEATURE
<222> LOCATION: (16)..(16)
<223> OTHER INFORMATION: X is any amino acid
<220> FEATURE:
<221> NAME/KEY: MISC_FEATURE
<222> LOCATION: (18)..(19)
<223> OTHER INFORMATION: X is any amino acid
<220> FEATURE:
<221> NAME/KEY: MISC_FEATURE
<222> LOCATION: (22)..(28)
<223> OTHER INFORMATION: X is any amino acid
<220> FEATURE:
<221> NAME/KEY: MISC_FEATURE
<222> LOCATION: (34)..(34)
<223> OTHER INFORMATION: X is any amino acid
<220> FEATURE:
<221> NAME/KEY: MISC_FEATURE
<222> LOCATION: (37)..(37)
<223> OTHER INFORMATION: X is any amino acid
<220> FEATURE:
<221> NAME/KEY: MISC_FEATURE
<222> LOCATION: (39)..(39)
<223> OTHER INFORMATION: X is any amino acid
<220> FEATURE:
<221> NAME/KEY: MISC_FEATURE
<222> LOCATION: (41)..(43)
<223> OTHER INFORMATION: X is any amino acid
<220> FEATURE:
<221> NAME/KEY: MISC_FEATURE
<222> LOCATION: (45)..(45)
<223> OTHER INFORMATION: X is any amino acid
<220> FEATURE:
<221> NAME/KEY: MISC_FEATURE
<222> LOCATION: (47)..(47)
<223> OTHER INFORMATION: X is any amino acid
<220> FEATURE:
<221> NAME/KEY: MISC_FEATURE
<222> LOCATION: (49)..(50)
<223> OTHER INFORMATION: X is any amino acid
<220> FEATURE:
<221> NAME/KEY: MISC_FEATURE
<222> LOCATION: (52)..(53)
<223> OTHER INFORMATION: X is any amino acid
<220> FEATURE:
<221> NAME/KEY: MISC_FEATURE
<222> LOCATION: (55)..(55)
<223> OTHER INFORMATION: X is any amino acid
<220> FEATURE:
<221> NAME/KEY: MISC_FEATURE
<222> LOCATION: (58)..(59)
<223> OTHER INFORMATION: X is any amino acid
<220> FEATURE:
<221> NAME/KEY: MISC_FEATURE
<222> LOCATION: (61)..(64)
<223> OTHER INFORMATION: X is any amino acid
<220> FEATURE:
<221> NAME/KEY: MISC_FEATURE
<222> LOCATION: (68)..(70)
<223> OTHER INFORMATION: X is any amino acid
<220> FEATURE:
<221> NAME/KEY: MISC_FEATURE
<222> LOCATION: (72)..(74)
<223> OTHER INFORMATION: X is any amino acid
<220> FEATURE:
<221> NAME/KEY: MISC_FEATURE
<222> LOCATION: (77)..(79)
<223> OTHER INFORMATION: X is any amino acid
<220> FEATURE:
<221> NAME/KEY: MISC_FEATURE
<222> LOCATION: (81)..(86)
<223> OTHER INFORMATION: X is any amino acid
<220> FEATURE:
<221> NAME/KEY: MISC_FEATURE
<222> LOCATION: (90)..(90)
<223> OTHER INFORMATION: X is any amino acid
```

```
<220> FEATURE:
<221> NAME/KEY: MISC_FEATURE
<222> LOCATION: (92)..(92)
<223> OTHER INFORMATION: X is any amino acid
<220> FEATURE:
<221> NAME/KEY: MISC_FEATURE
<222> LOCATION: (97)..(97)
<223> OTHER INFORMATION: X is any amino acid
<220> FEATURE:
<221> NAME/KEY: MISC_FEATURE
<222> LOCATION: (99)..(102)
<223> OTHER INFORMATION: X is any amino acid
<220> FEATURE:
<221> NAME/KEY: MISC_FEATURE
<222> LOCATION: (106)..(106)
<223> OTHER INFORMATION: X is any amino acid
<220> FEATURE:
<221> NAME/KEY: MISC_FEATURE
<222> LOCATION: (108)..(110)
<223> OTHER INFORMATION: X is any amino acid
<220> FEATURE:
<221> NAME/KEY: MISC_FEATURE
<222> LOCATION: (113)..(136)
<223> OTHER INFORMATION: X is any amino acid
<220> FEATURE:
<221> NAME/KEY: MISC_FEATURE
<222> LOCATION: (140)..(140)
<223> OTHER INFORMATION: X is any amino acid
<220> FEATURE:
<221> NAME/KEY: MISC_FEATURE
<222> LOCATION: (152)..(154)
<223> OTHER INFORMATION: X is any amino acid
<220> FEATURE:
<221> NAME/KEY: MISC_FEATURE
<222> LOCATION: (156)..(166)
<223> OTHER INFORMATION: X is any amino acid
<220> FEATURE:
<221> NAME/KEY: MISC_FEATURE
<222> LOCATION: (168)..(175)
<223> OTHER INFORMATION: X is any amino acid
<220> FEATURE:
<221> NAME/KEY: MISC_FEATURE
<222> LOCATION: (177)..(181)
<223> OTHER INFORMATION: X is any amino acid
<220> FEATURE:
<221> NAME/KEY: MISC_FEATURE
<222> LOCATION: (183)..(185)
<223> OTHER INFORMATION: X is any amino acid
<220> FEATURE:
<221> NAME/KEY: MISC_FEATURE
<222> LOCATION: (188)..(200)
<223> OTHER INFORMATION: X is any amino acid
<220> FEATURE:
<221> NAME/KEY: MISC_FEATURE
<222> LOCATION: (202)..(205)
<223> OTHER INFORMATION: X is any amino acid
<220> FEATURE:
<221> NAME/KEY: MISC_FEATURE
<222> LOCATION: (207)..(209)
<223> OTHER INFORMATION: X is any amino acid
<220> FEATURE:
<221> NAME/KEY: MISC_FEATURE
<222> LOCATION: (211)..(211)
<223> OTHER INFORMATION: X is any amino acid
<220> FEATURE:
<221> NAME/KEY: MISC_FEATURE
<222> LOCATION: (213)..(216)
<223> OTHER INFORMATION: X is any amino acid
<220> FEATURE:
<221> NAME/KEY: MISC_FEATURE
<222> LOCATION: (236)..(241)
<223> OTHER INFORMATION: X is any amino acid
<220> FEATURE:
<221> NAME/KEY: MISC_FEATURE
<222> LOCATION: (243)..(244)
<223> OTHER INFORMATION: X is any amino acid
<220> FEATURE:
<221> NAME/KEY: MISC_FEATURE
<222> LOCATION: (246)..(251)
```

```
<223> OTHER INFORMATION: X is any amino acid
<220> FEATURE:
<221> NAME/KEY: MISC_FEATURE
<222> LOCATION: (253)..(255)
<223> OTHER INFORMATION: X is any amino acid
<220> FEATURE:
<221> NAME/KEY: MISC_FEATURE
<222> LOCATION: (257)..(261)
<223> OTHER INFORMATION: X is any amino acid
<220> FEATURE:
<221> NAME/KEY: MISC_FEATURE
<222> LOCATION: (263)..(265)
<223> OTHER INFORMATION: X is any amino acid
<220> FEATURE:
<221> NAME/KEY: MISC_FEATURE
<222> LOCATION: (267)..(272)
<223> OTHER INFORMATION: X is any amino acid
<220> FEATURE:
<221> NAME/KEY: MISC_FEATURE
<222> LOCATION: (276)..(276)
<223> OTHER INFORMATION: X is any amino acid

<400> SEQUENCE: 67

Met Met Lys Xaa Xaa Xaa Ile Xaa Gly Ser Pro Arg Lys Xaa Gly Xaa
1               5                   10                  15

Thr Xaa Xaa Leu Leu Xaa Xaa Xaa Xaa Xaa Xaa Lys Glu Ala Ala
            20                  25                  30

Lys Xaa Leu Ile Xaa Gly Xaa Glu Xaa Xaa Xaa Phe Xaa Leu Xaa Asp
        35                  40                  45

Xaa Xaa Ile Xaa Xaa Cys Xaa Gly Cys Xaa Xaa Cys Xaa Xaa Xaa Xaa
50                  55                  60

Ser Asn Ser Xaa Xaa Xaa Cys Xaa Xaa Xaa Asp Asp Xaa Xaa Xaa Ile
65                  70                  75                  80

Xaa Xaa Xaa Xaa Xaa Xaa Glu Ala Asp Xaa Ile Xaa Phe Gly Ser Pro
                85                  90                  95

Xaa Tyr Xaa Xaa Xaa Xaa Thr Gly Gln Xaa Lys Xaa Xaa Xaa Asp Arg
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Leu Ile Thr Xaa Phe Ile Tyr Thr
        130                 135                 140

Met Asn Val Lys Glu Glu Val Xaa Xaa Xaa Gly Xaa Xaa Xaa Xaa Xaa
145                 150                 155                 160

Xaa Xaa Xaa Xaa Xaa Xaa Asn Xaa Xaa Xaa Xaa Xaa Xaa Xaa Xaa Met
                165                 170                 175

Xaa Xaa Xaa Xaa Xaa Asn Xaa Xaa Xaa Ile Thr Xaa Xaa Xaa Xaa Xaa
        180                 185                 190

Xaa Xaa Xaa Xaa Xaa Xaa Xaa Xaa Gly Xaa Xaa Xaa Xaa Pro Xaa Xaa
        195                 200                 205

Xaa Lys Xaa Asp Xaa Xaa Xaa Lys Val Ser Lys Lys Phe Ile Tyr
    210                 215                 220

Cys Ile Glu Glu Lys Lys Asn Pro Pro Val Leu Xaa Xaa Xaa Xaa Xaa
225                 230                 235                 240

Xaa Leu Xaa Xaa Phe Xaa Xaa Xaa Xaa Xaa Ala Xaa Xaa Xaa Gly
        245                 250                 255
```

-continued

```
Xaa Xaa Xaa Xaa Xaa Val Xaa Xaa Ile Xaa Xaa Xaa Xaa Xaa Xaa
            260                 265             270

Gly Ile Ser Xaa Pro Glu Ser Glu Pro Arg Val Ala Thr Asn Phe Ile
        275             280                 285

Arg
```